US009290773B2

(12) United States Patent
Edgerton

(10) Patent No.: US 9,290,773 B2
(45) Date of Patent: Mar. 22, 2016

(54) TRANSGENIC PLANTS WITH ENHANCED AGRONOMIC TRAITS

(75) Inventor: Michael D. Edgerton, St. Louis, MO (US)

(73) Assignee: Monsanto Technology LLC, St. Louis, MO (US)

(*) Notice: Subject to any disclaimer, the term of this patent is extended or adjusted under 35 U.S.C. 154(b) by 855 days.

(21) Appl. No.: 13/199,773

(22) Filed: Sep. 8, 2011

(65) Prior Publication Data

US 2012/0227131 A1  Sep. 6, 2012

Related U.S. Application Data

(63) Continuation of application No. 11/982,680, filed on Nov. 2, 2007, now abandoned, which is a continuation-in-part of application No. 10/678,588, filed on Oct. 2, 2003, now abandoned, and a continuation-in-part of application No. 10/679,063, filed on Oct. 2, 2003, now abandoned.

(60) Provisional application No. 60/415,758, filed on Oct. 2, 2002, provisional application No. 60/425,157, filed on Nov. 8, 2002, provisional application No. 60/463,787, filed on Apr. 18, 2003, provisional application No. 60/415,758, filed on Oct. 2, 2002.

(51) Int. Cl.
    C12N 15/82    (2006.01)
    A01H 5/10     (2006.01)
    C07K 14/47    (2006.01)

(52) U.S. Cl.
    CPC .............. *C12N 15/8273* (2013.01); *A01H 5/10* (2013.01); *C07K 14/4702* (2013.01)

(58) Field of Classification Search
    None
    See application file for complete search history.

(56) References Cited

U.S. PATENT DOCUMENTS

| | | | |
|---|---|---|---|
| 5,322,938 A | 6/1994 | McPherson et al. | |
| 5,641,876 A | 6/1997 | McElroy et al. | |
| 6,084,089 A | 7/2000 | Mine et al. | |
| 6,140,078 A | 10/2000 | Sanders et al. | |
| 6,162,965 A * | 12/2000 | Hansen | 800/278 |
| 6,194,636 B1 | 2/2001 | McElroy et al. | |
| 6,232,526 B1 | 5/2001 | McElroy et al. | |
| 6,235,975 B1 | 5/2001 | Harada et al. | |
| 6,677,504 B2 | 1/2004 | da Costa e Silva et al. | |
| 6,717,034 B2 | 4/2004 | Jiang | |
| 7,151,204 B2 | 12/2006 | Houmard et al. | |
| 7,482,511 B2 | 1/2009 | da Costa e Silva et al. | |
| 7,511,130 B2 | 3/2009 | Heck et al. | |
| 7,511,190 B2 | 3/2009 | Creelman et al. | |
| 7,868,149 B2 | 1/2011 | Boukharov et al. | |
| 2002/0102695 A1 | 8/2002 | Silva et al. | |
| 2003/0093837 A1 | 5/2003 | Keddie et al. | |
| 2003/0233670 A1 | 12/2003 | Edgerton et al. | |
| 2004/0019927 A1 | 1/2004 | Sherman et al. | |
| 2004/0031072 A1 | 2/2004 | La Rosa et al. | |
| 2004/0034888 A1 | 2/2004 | Liu et al. | |
| 2004/0123347 A1 | 6/2004 | Hinchey et al. | |
| 2005/0022266 A1 | 1/2005 | Wu et al. | |
| 2005/0048556 A1 | 3/2005 | Heck et al. | |
| 2005/0086718 A1 | 4/2005 | Heard et al. | |
| 2005/0172361 A1 | 8/2005 | Heard | |
| 2006/0021087 A1 | 1/2006 | Baum et al. | |
| 2007/0039076 A1 | 2/2007 | Boukharov et al. | |
| 2007/0192889 A1 | 8/2007 | La Rosa et al. | |
| 2008/0040973 A1 | 2/2008 | Nelson et al. | |
| 2008/0104730 A1 | 5/2008 | Wu et al. | |
| 2008/0163397 A1 | 7/2008 | Ratcliffe et al. | |
| 2008/0313756 A1 | 12/2008 | Zhang et al. | |
| 2009/0044297 A1 * | 2/2009 | Andersen et al. | 800/289 |
| 2009/0049566 A1 | 2/2009 | Zhang et al. | |
| 2009/0049573 A1 | 2/2009 | Dotson et al. | |
| 2009/0093620 A1 | 4/2009 | Kovalic et al. | |
| 2009/0138981 A1 | 5/2009 | Repetti et al. | |
| 2009/0183270 A1 | 7/2009 | Adams et al. | |
| 2009/0217414 A1 * | 8/2009 | La Rosa et al. | 800/278 |
| 2009/0241217 A9 | 9/2009 | Wu et al. | |
| 2010/0293663 A2 | 11/2010 | La Rosa et al. | |

FOREIGN PATENT DOCUMENTS

| | | |
|---|---|---|
| EP | 03008540 A2 | 1/2003 |
| EP | 1230345 B1 | 6/2008 |
| WO | WO-02057439 A2 | 7/2002 |
| WO | WO-2005033319 A2 | 1/2005 |

OTHER PUBLICATIONS

Wells, Biochemistry 29:8509-8517, 1990.*
Ngo et al., (The Protein Folding Problem and Tertiary Structure Prediction, K. Merz., and S. Le Grand (eds.) pp. 492-495,1994).*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000).*
Doerks et al., (TIG, 14:248-250, 1998).*
Smith et al. (Nature Biotechnology, 15:1222-1223, 1997).*
Bork et al. (TIG, 12:425-427, 1996).*
Sims et al., Plant Mol. Biol., 47:771-781, 2001.*

(Continued)

*Primary Examiner* — Vinod Kumar
(74) *Attorney, Agent, or Firm* — Schwegman Lundberg & Woessner, P.A.

(57) ABSTRACT

This invention provides transgenic plant cells with recombinant DNA for expression of proteins that are useful for imparting enhanced agronomic trait(s) to transgenic crop plants. This invention also provides transgenic plants and progeny seed comprising the transgenic plant cells where the plants are selected for having an enhanced trait selected from the group of traits consisting of enhanced water use efficiency, enhanced cold tolerance, increased yield, enhanced nitrogen use efficiency, enhanced seed protein and enhanced seed oil. Also disclosed are methods for manufacturing transgenic seed and plants with enhanced traits.

11 Claims, 5 Drawing Sheets

(56) References Cited

OTHER PUBLICATIONS

Kim et al. (The Plant Journal, 25:247-259, 2001).*
"U.S. Appl. No. 11/982,010, Office Action mailed Jan. 6, 2011".
"U.S. Appl. No. 11/982,010, Response filed Jul. 6, 2011".
"U.S. Appl. No. 11/982,274, Final Office Action mailed Aug. 1, 2011".
"U.S. Appl. No. 11/982,274, Office Action mailed Oct. 31, 2007".
"U.S. Appl. No. 11/982,274, Response filed Apr. 27, 2011 to Office Action".
"U.S. Appl. No. 11/982,680, Non Final Office Action mailed Mar. 11, 2011", 22 pgs.
"U.S. Appl. No. 11/982,680, Response filed Dec. 21, 2010 to Restriction Requirement mailed Aug. 27, 2010", 2 pgs.
"U.S. Appl. No. 11/982,680, Restriction Requirement mailed Aug. 27, 2008", 7 pgs.
"GeneBank Accession No. X59714, dated Nov. 15, 1992".
"Sequence alignment between the sequence encoded by SEQ ID No. 29", U.S. Appl. No. 11/821,176 vs. SEQ ID No. 617 in U.S. Appl. No. 11/982,680,dated May 17, 2010.
"Sequence alignment between the sequence encoded by SEQ ID No. 30", U.S. Appl. No. 11/821,176 vs. SEQ ID No. 617 in U.S. Appl. No. 11/982,680,dated May 17, 2010.
"Sequence alignment between the sequence encoded by SEQ ID No. 31", U.S. Appl. No. 11/821,176 vs. SEQ ID No. 617 in U.S. Appl. No. 11/982,680,dated May 17, 2010.
"Sequence alignment between the sequence encoded by SEQ ID No. 32", U.S. Appl. No. 11/821,176 vs. SEQ ID No. 617 in U.S. Appl. No. 11/982,680, dated May 17, 2010.
"Summary of drought tolerance data for NF-YB variants", (undated).
"Summary of SEQ ID No. 29 data for yield under stress (SEQ ID No. 29 is NFYB2-S83A modified NF-YB2 protein of U.S. Appl. No. 11/821,176)", (undated).
Bork, Peer, "Go hunting in sequence databases but watch out for the traps", Trends in Genetics, 12(10), (Oct. 1996), 425-427.
Doerks, Tobias, et al., "Protein Annotation: detective work for function prediction", Trends in Genetics, vol. 14, No. 6, (1998), 248-250.
Edwards, et al., "Multiple genes encoding the conserved CCAAT-Box transcription factor complex are expressed in arabidopsis", Plant Physiol., 117, (1998), 1015-1022.
Gordon, et al., "RNAi for insect-proof plants", Nature Biotechnology, 25(11), (2007), 1231-1232.
Guo, H. H, et al., "Protein tolerance to random amino acid change", Proc Natl Acad Sci U S A., 101(25), (2004), 9205-9210.
Keskin, O., et al., "A new, structurally nonredundant, diverse data set of protein-protein interfaces and its implications.", Protein Sci.,13(4), (Apr. 2004), 1043-55.
Lee, et al., "Arabidopsis Leafy COTYLEDON1 represents a functionally specialized subunit of the CCAAT binding transcription factor", Proc. Natl. Acad. Sci. USA, 100(4), (2003), 2152-2156.
Li, et al., "Evolutionary variation of the CCAAT-binding transcription factor NF-Y", Nucleic Acids Research, 20(5), (1992), 1087-1091.
Lotan, et al., "Arabidopsis Leafy COTYLEDON1 is sufficient to induce embryo development in vegetative cells", Cell, 93, (1998), 1195-1205.
Mantovani, "The molecular biology of the CCAAT-binding factor NF-Y", Gene, 239, (1999), 15-27.
Miyoshi, et al., "OsHAP3 genes regulate chloroplast biogenesis in rice", Plant J., 36, (2003), 532-540.
Nelson, et al., "Plant nuclear factor Y (NF-7) B subunits confer drought tolerance and lead to improved corn yields on water-limited areas", Proc. Natl. Acad. Sci.. USA, 104(42), (2007), 16450-16455.
Ngo, et al., "Computational complexity, protein structure prediction, and the leventhal paradox", In: The protein folding problem and tertiary structure prediction, Mertz, et al.. (Eds.), (1994), 1-80.
Smith, Temple F, et al., "The Challenges of Genome Sequence Annotation or "The Devil is in the Details"", Nature Biotechnology, 15(12), (Nov. 1997), 1222-1223.
Stephenson, et al., "Genome-wide identification and expression analysis of the NF-Y family of transcription factors in triticum aestivum", Plant. Mol. Biol., 65, (2007), 77-92.
Thornton, J. M., et al., "From structure to function: Approaches and limitations.", Nat Struct Biol., 7(Suppl), (Nov. 2000), 991-994.
Vilardell, "Regulation of the maize rab17 gene promoter in transgenic heterologous systems", Plant Mol. Biol., 17, (1991), 985-993.
Wells, J. A., "Additivity of Mutational Effects in Proteins", Biochemistry 29(37), (1990), 8509-8517.
Cao, Yongwei, et al., "cDNA Sequences and Uses for Plant Improvement", U.S. Appl. No. 10/219,999, filed Aug. 15, 2002, 189 pgs.
Cao, Yongwei, et al., "cDNA Sequences and Uses for Plant Improvement", U.S. Appl. No. 60/324,109, filed Sep. 21, 2001, 108 pgs.

* cited by examiner

FIG. 1A

```
SEQ ID NO
932         AIVLIPGPFISQRCRSRV------LPPLSFPLERKIGLLGLIG----------------C
9332        TALLVPIALINCACRRSQSTTSTPAQAMSCRLLFKLFLCAFLGSAGLTLQALTKFVKKSC
4683        TLVMLPFALFFEKGTR--------PKMTLRIFIKILGLALLE---------------P
3207        LALLIPFAYFLEKKNR--------PPLTFSLLAQLFFLAFCG---------------I
7313        LALLAPFAYFLEKKDR--------PPLTFSLLVEFFLLALCG---------------I
3221        LALLAPFAYFLEKKDR--------PPLTFSLLVEFFLLALCG---------------I
6752        LALLAPFAYFLEKKDR--------PPLTFSLLVEFFLLALCG---------------I
consensus   xallxPfaxfxekxxr--------ppltfxllxxxfllalxg---------------x -ASQIV-------------------GYTGISFSSPTLSSAISNLVPAFTFLLAIIFRME
QEVGGFTSLLSSSLLQGKAEHLHPQVYHASLKQTSATVASAATNSMPVVTFLLALVLRME
VLDQNL-------------------YYVGNARASASFSSALVNILPAVTFIMAIVLRME
TCNQGF-------------------YLLGLHYLSPTYASAIQNTVPAITFALAASLRLE
TANQGF-------------------YLLGLYHLSPTYASAIQNTVPAITFAMAAVLRLE
TANQGF-------------------YLLGLYHLSPTYASAIQNTVPAITFAMAAVLRLE
TANQGF-------------------YLLGLYHLSPTYASAIQNTVPAITFAMAAVLRLE
xxxqgf-------------------yxxglxxxSptxaSAixNxvPaxTFxxAxvlRxE KVIVRNTTCQAKVLGTIVSITGAFVVTFYKGPPIIIVHTPSLSLHQPIN---TLNSVDRS
TIKLRRRSGLGKLAGVALCLAGVLVIAFYVGPSI------RPLAHHPVFAHKTQSVGNGA
KLRLRSSHSQAKVAGTICTVIGAVLMIMYHG-PVVQFPWARGAHHVDQAASAAAAQSSAT
QVNINKRYGMAKVIGTVVSVGGATVITLYKGTPLMNF--NILGANT------VSQNVVLN
QVDLGKRHGVAKVVGTVVSIGGATVITLYKGLPLFNHNLNIKSL--------SSSSLILN
QVDLGKRHGVAKVVGTVVSIGGATVITLYKGLPLFNHNLNIKSL--------SSSSLILN
QVDLSRRHGLAKVVGTVVSIGGATVITLYKGLPLLHHSDDLHVKSSPVTLSSSSGSPILN
xvxlxxrxgxaKvxGtxvsxxGaxvitxYkGxpxxxxxxxxxxxxxxxxxxxxxxxxxx WAIGGLLLTAEYILVPLWYIVQVQIMKVYPNELTVIFFYNLCVSIMAAIVAIFTET-NAG
WIRGTFLLILSCTTWSLWITLQVPLLIEYPNKLMATAMQCLFSALQSFVVAVVVEK-DFT
WLKGTIAIITSCVAWAGFFVLQSNTLNSYPAALTLTTLICAMGTGINGSMALVAERHDMS
WSVGCLFLLGNCIAWSGWMVLQTPVLKKYPARLSMLALTLAFGLVQFLAIAAFWEN-DIG
WTLGCVFILGHCLSWSGWMVLQVPVLKRYPARLSVLSLTCIFGLLQFLVIAAFTEE-DLS
WTLGCVFILGHCLSWSGWMVLQVPVLKRYPARLSVLSLTCIFGLLQFLVIAAFTEE-DLS
WTLGCVFILGHCLSWSGWMVLQVPVLKRYPARLSVLSLTCIFGLLQFLAIAAFTEE-DLS
WxxGxxxxxxxcxxwsgwxvlQvpxlkxYPaxLxxxxlxcxfgxxqxxxxAxfxEx-dxx AWKIGLDTALASIVCSGIFGSFVNNAVHTWVLRIKGPVYVAMFKPLSIAIAVALGVMFLG
KWKLGLDIGLL----AAFLGTGALMYLQAWCAEMSGPVFVVMWSPLAFIFTIFSSSFFLG
AWVIGLDTRLFTVVYSGVVCSGVAFFVQGIVTETRGPVFVTAFQPLCMIITAVLGSVILK
KWRLHSGEELFTILYAGLVASGVALSLQIWCIDRGGALFTAIFQPVQTVMVAIMAAVILG
RWKVNSGSELFTILYAGLVASGVAFALQIWCIDRGGPLFTAVFQPVQTVAVAVMAAIILG
RWKVNSGSELFTILYAGLVASGVAFALQIWCIDRGGPLFTAVFQPVQTVAVAVMAAIILG
RWKVRSGGELFTILYAGLVASGVAFALQIWCIDRGGPLFTAVFQPVQTVAVAVMASAILG
xWkxxxxxxLftixyagxvxsgvaxxlqxwcxxxxGpxfxaxfqPxxxxxxaxxxxxiLg DTLHLGSLVGATVISIGFYTVMWGKATE---------------------------ENVDE
EVVHLGSILGGILLVGGLYSVLWGKSNE---------------------------RKNMIL
```

FIG. 1B

```
EETTLGSVIGAAIIVLGLYSLIWGKSNDIIDKPVHSVAEKLALAHLRQRQRQRHQRHQRD
DLLYTGGIIGAVLIVIGLYLVLWGKNEE------------------------KKSNSN
DQLYSGGIIGAVLIVIGLYFVLWGKSEE------------------------KKSKNN
DQLYSGGIIGAVLIVIGLYFVLWGKSEE------------------------KKSKNN
DQLYTGGIIGAVLIVIGLYFVLWGKSAE------------------------KKGARN
dxlxxGxiiGaxliviGlYxvlWGKsxe------------------------xkxxxx DVPGQQSPPTTENVPLLQSYKT-----DTAEKKMHGSV--------------------
PVMPEKSQGQGD-------GDGA----TTQEKHGETNLTSQV----------------
QRRQARQRRPGRPRRRDAGGEGRDLPLATTRRHLARAPTYVLRAFLRSRVWSRNLLYV
QXX---------DLSRHLLSE------ESSRPTTVTSD--------------------
NLQDQPVQGGGDDIRRHLLGQE-----DASRKDEEAAVTDELA---------------
NLQDQPVQGGGDDIRRHLLGQE-----DASRKDEEAAVTDELA---------------
LLQDQLAQGA--DVTRHLLGG------EASAKDEEAAPAMLA---------------
xxxxxxxxxxxxxxrxxxgxx------xxxxkxxxxxxxxxx---------------
```

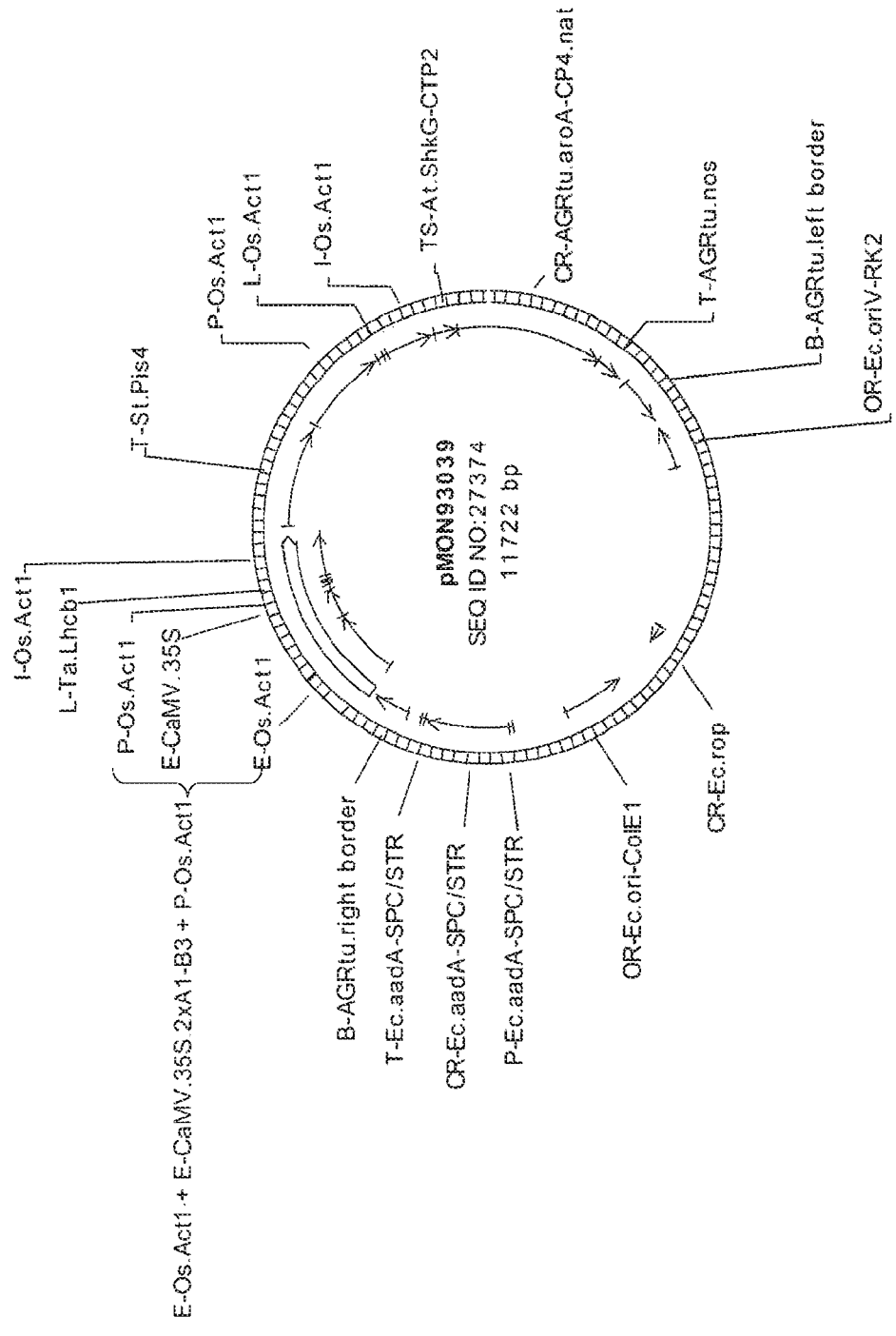
FIG. 2 Plasmid map of pMON93039

FIG. 3 Plasmid map of pMON82053
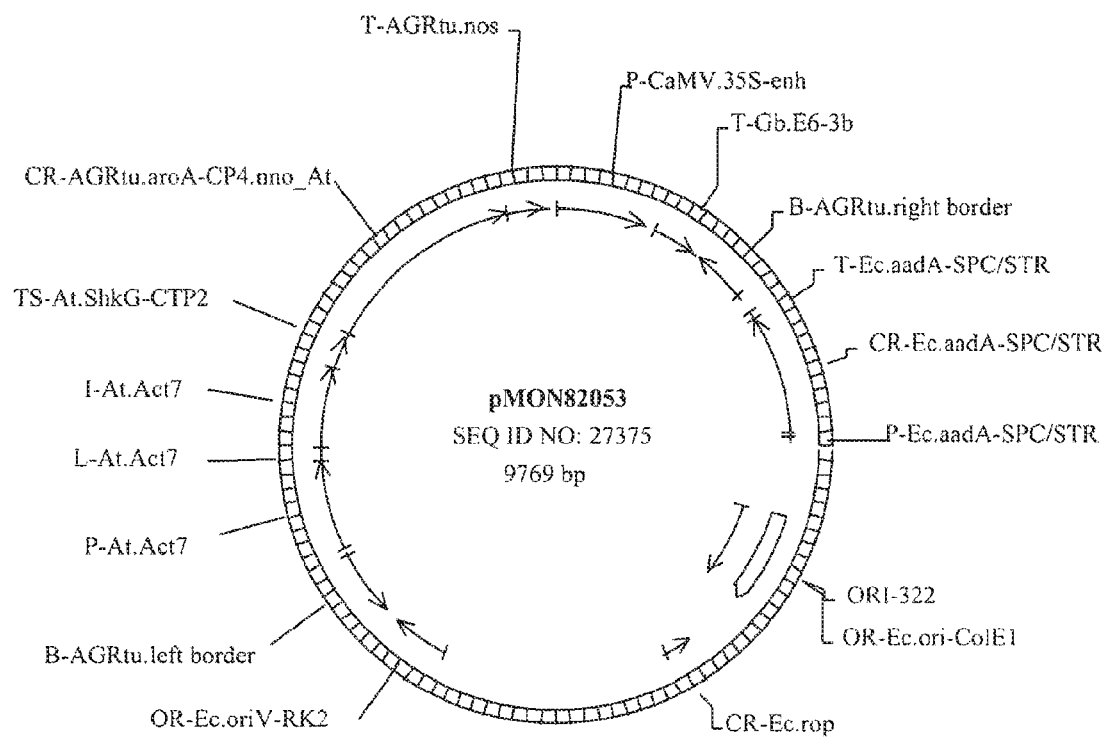

FIG. 4 Plasmid map of pMON99053
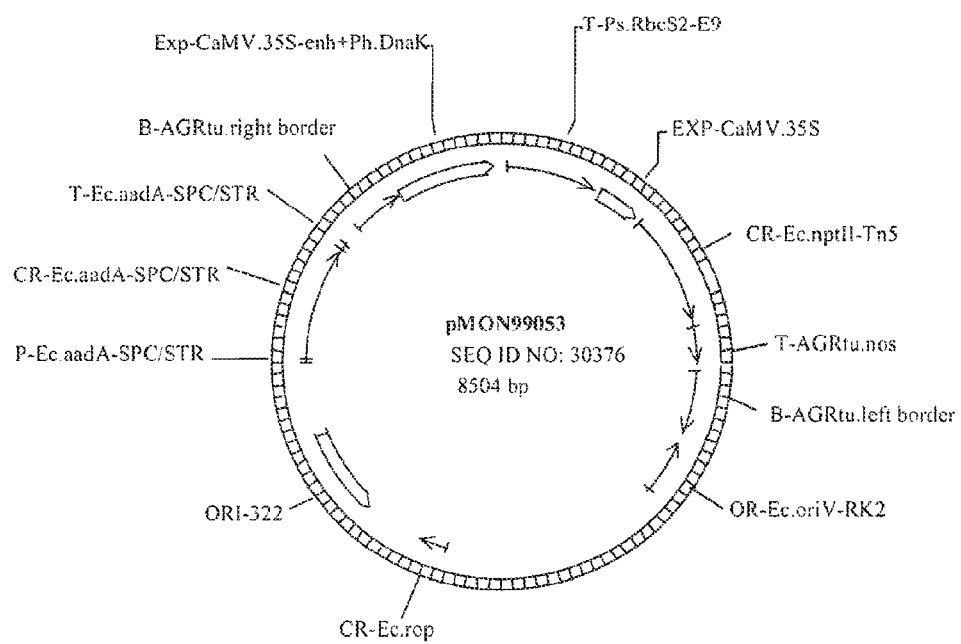

TRANSGENIC PLANTS WITH ENHANCED AGRONOMIC TRAITS

RELATED APPLICATIONS

This application is a continuation application of Ser. No. 11/982,680, filed Nov. 2, 2007 (pending). Application Ser. No. 11/982,680 is a continuation in part of application Ser. No. 10/678,588 (abandoned), filed Oct. 2, 2003, which claims the benefit under 35 U.S.C. 119(e) of provisional application Ser. Nos. 60/415,758, filed Oct. 2, 2002, 60/425,157, filed Nov. 8, 2002 and 60/463,787, filed Apr. 18, 2003, the disclosures of which are incorporated herein by reference in their entirety.

Application Ser. No. 11/982,680 (pending) is also a continuation in part of application Ser. No. 10/679,063 (abandoned), filed Oct. 2, 2003, which claims the benefit under 35 U.S.C. 119(e) of provisional application 60/415,758, filed Oct. 2, 2002, the disclosures of which are incorporated herein by reference in their entirety.

INCORPORATION OF SEQUENCE LISTING

Three copies of the a sequence listing (Copy 1 and Copy 2 and a computer readable form), in a text file named "38-21 (52054)A_seqList.txt" which is 100.3 MB (measured in MS-WINDOWS) are provided on separate CD-ROMs which were created on Oct. 30, 2007 and are herein incorpated by reference.

INCORPORATION OF COMPUTER PROGRAM LISTING

Two copies of Computer Program Listing (Copy 1 and Copy 2) containing folders "hmmer-2.3.2" and "241pfam" are provided on separate CD-ROMs that were created on Oct. 30, 2007, and have a total file size of 20.3 MB (measured in MS-WINDOWS). The "hmmer-2.3.2" folder contains the source code and other associated ASCII files for implementing the HMMer software for Pfam analysis; the "241 pfam" folder contains ASCII files of 241 Pfam Hidden. Markov Models; as well as the material on replacement CDs (Copy 1 and Copy 2) containing folders "hmmer-2.3.2" and "241pfamDir" are provided on separate CD-ROMs that were created on Dec. 12, 2011, and have a total file size of 20,480, 616 bytes, created on Dec. 12, 2011, all of which are incorporated herein by reference in their entirety.

INCORPORATION OF TABLES

Two copies of Table 7 (Copy 1 and Copy 2) are provided on CDROMs that were created on Sep. 6, 2011 and contain the file named "38-21(52054)D_table7.txt" which is 369 KB (measured in MS-WINDOWS) which comprises 71 pages when viewed in MS Word®, are herein incorporated by reference.

FIELD OF THE INVENTION

Disclosed herein are inventions in the field of plant genetics and developmental biology. More specifically, the present inventions provide plant cells with recombinant DNA for providing an enhanced trait in a transgenic plant, plants comprising such cells, seed and pollen derived from such plants, methods of making and using such cells, plants, seeds and pollen.

SUMMARY OF THE INVENTION

This invention provides plant cell nuclei with recombinant DNA that imparts enhanced agronomic traits in transgenic plants having the nuclei in their cells, e.g. enhanced water use efficiency, enhanced cold tolerance, increased yield, enhanced nitrogen use efficiency, enhanced seed protein or enhanced seed oil. Such recombinant DNA in a plant cell nucleus of this invention is provided in as a construct comprising a promoter that is functional in plant cells and that is operably linked to DNA that encodes a protein or to DNA that results in gene suppression. Such DNA in the construct is sometimes defined by protein domains of an encoded protein targeted for production or suppression, e.g. a "Pfam domain module" (as defined herein below) from the group of Pfam domain modules identified in Table 21 (page 94). Alternatively, e.g. where a Pfam domain module is not available, such DNA in the construct is defined a consensus amino acid sequence of an encoded protein that is targeted for production e.g. a protein having amino acid sequence with at least 90% identity to a consensus amino acid sequence in the group of SEQ ID NO: 27377 through SEQ ID NO: 27426. Alternatively, in other cases where neither a Pfam domain module nor a consensus amino acid sequence is available, such DNA in the construct is defined by the sequence of a specific encoded and or its homologue proteins.

Other aspects of the invention are specifically directed to transgenic plant cells comprising the recombinant DNA of the invention, transgenic plants comprising a plurality of such plant cells, progeny transgenic seed, embryo and transgenic pollen from such plants. Such transgenic plants are selected from a population of transgenic plants regenerated from plant cells transformed with recombinant DNA and expressed the protein by screening transgenic plants in the population for an enhanced trait as compared to control plants that do not have said recombinant DNA, where the enhanced trait is selected from group of enhanced traits consisting of enhanced water use efficiency, enhanced cold tolerance, increased yield, enhanced nitrogen use efficiency, enhanced seed protein and enhanced seed oil.

In yet another aspect of the invention the plant cells, plants, seeds, embryo and pollen further comprise DNA expressing a protein that provides tolerance from exposure to an herbicide applied at levels that are lethal to a wild type plant cell. Such tolerance is especially useful not only as an advantageous trait

---

LENGTHY TABLES

The patent contains a lengthy table section. A copy of the table is available in electronic form from the USPTO web site (http://seqdata.uspto.gov/?pageRequest=docDetail&DocID=US09290773B2). An electronic copy of the table will also be available from the USPTO upon request and payment of the fee set forth in 37 CFR 1.19(b)(3).

in such plants but is also useful in a selection step in the methods of the invention. In aspects of the invention the agent of such herbicide is a glyphosate, dicamba, or glufosinate compound.

Yet other aspects of the invention provide transgenic plants which are homozygous for the recombinant DNA and transgenic seed of the invention from corn, soybean, cotton, canola, alfalfa, wheat or rice plants.

This invention also provides methods for manufacturing non-natural, transgenic seed that can be used to produce a crop of transgenic plants with an enhanced trait resulting from expression of stably-integrated, recombinant DNA in the nucleus of the plant cells. More specifically the method comprises (a) screening a population of plants for an enhanced trait and recombinant DNA, where individual plants in the population can exhibit the trait at a level less than, essentially the same as or greater than the level that the trait is exhibited in control plants which do not express the recombinant DNA; (b) selecting from the population one or more plants that exhibit the trait at a level greater than the level that said trait is exhibited in control plants and (c) collecting seed from a selected plant. Such method further comprises steps (a) verifying that the recombinant DNA is stably integrated in said selected plants; and (b) analyzing tissue of a selected plant to determine the production of a protein having the function of a protein encoded by a recombinant DNA with a sequence of one of SEQ ID NO: 1-614; In one aspect of the invention the plants in the population further comprise DNA expressing a protein that provides tolerance to exposure to an herbicide applied at levels that are lethal to wild type plant cells and where the selecting is effected by treating the population with the herbicide, e.g. a glyphosate, dicamba, or glufosinate compound. In another aspect of the invention the plants are selected by identifying plants with the enhanced trait. The methods are especially useful for manufacturing corn, soybean, cotton, alfalfa, wheat or rice seed selected as having one of the enhanced traits described above.

Another aspect of the invention provides a method of producing hybrid corn seed comprising acquiring hybrid corn seed from a herbicide tolerant corn plant which also has stably-integrated, recombinant DNA comprising a promoter that is (a) functional in plant cells and (b) is operably linked to DNA that encodes a protein having at least one domain of amino acids in a sequence that exceeds the Pfam gathering cutoff for amino acid sequence alignment with a protein domain family identified by a Pfam name in the group of Pfam names identified in Table 22. The methods further comprise producing corn plants from said hybrid corn seed, wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA; selecting corn plants which are homozygous and hemizygous for said recombinant DNA by treating with an herbicide; collecting seed from herbicide-treated-surviving corn plants and planting said seed to produce further progeny corn plants; repeating the selecting and collecting steps at least once to produce an inbred corn line; and crossing the inbred corn line with a second corn line to produce hybrid seed.

Another aspect of the invention provides a method of selecting a plant comprising plant cells of the invention by using an immunoreactive antibody to detect the presence of protein expressed by recombinant DNA in seed or plant tissue. Yet another aspect of the invention provides anti-counterfeit milled seed having, as an indication of origin, a plant cell of this invention.

Still other aspects of this invention relate to transgenic plants with enhanced water use efficiency or enhanced nitrogen use efficiency. For instance, this invention provides methods of growing a corn, cotton or soybean crop without irrigation water comprising planting seed having plant cells of the invention which are selected for enhanced water use efficiency. Alternatively methods comprise applying reduced irrigation water, e.g. providing up to 300 millimeters of ground water during the production of a corn crop. This invention also provides methods of growing a corn, cotton or soybean crop without added nitrogen fertilizer comprising planting seed having plant cells of the invention which are selected for enhanced nitrogen use efficiency.

BRIEF DESCRIPTION OF THE DRAWINGS

FIGS. 1A and 1B are a consensus amino acid sequence of SEQ ID NO: 932 and its homologs.

FIGS. 2-4 are plasmid maps.

DETAILED DESCRIPTION OF THE INVENTION

In the attached sequence listing:

SEQ ID NO:1-614 are nucleotide sequences of the coding strand of DNA for "genes" used in the recombinant DNA imparting an enhanced trait in plant cells, i.e. each represents a coding sequence for a protein;

SEQ ID NO: 615-1228 are amino acid sequences of the cognate protein of the "genes" with nucleotide coding sequences 1-614;

SEQ ID NO: 1229-27373 are amino acid sequences of homologous proteins;

SEQ ID NO: 27374 is a nucleotide sequence of a base plasmid vector useful for corn transformation;

SEQ ID NO: 27375 is a nucleotide sequence of a base plasmid vector useful for soybean and canola transformation;

SEQ ID NO: 27376 is a nucleotide sequence of a base plasmid vector useful for cotton transformation;

SEQ ID NO: 27377-27426 are consensus sequences.

TABLE 1

| PEP SEQ ID NO | Gene ID | Consensus SEQ ID |
|---|---|---|
| 684 | PHE0000499 | 27377 |
| 704 | PHE0000520 | 27378 |
| 705 | PHE0000521 | 27379 |
| 706 | PHE0000523 | 27380 |
| 710 | PHE0000528 | 27381 |
| 719 | PHE0000537 | 27382 |
| 734 | PHE0000552 | 27383 |
| 735 | PHE0000553 | 27384 |
| 738 | PHE0000556 | 27385 |
| 743 | PHE0000561 | 27386 |
| 744 | PHE0000562 | 27387 |
| 745 | PHE0000563 | 27388 |
| 746 | PHE0000564 | 27389 |
| 761 | PHE0000579 | 27390 |
| 777 | PHE0000601 | 27391 |
| 779 | PHE0000604 | 27392 |
| 793 | PHE0000618 | 27393 |
| 804 | PHE0000629 | 27394 |
| 824 | PHE0000649 | 27395 |
| 891 | PHE0000798 | 27396 |
| 896 | PHE0000803 | 27397 |
| 900 | PHE0000807 | 27398 |
| 918 | PHE0000826 | 27399 |

TABLE 1-continued

| PEP SEQ ID NO | Gene ID | Consensus SEQ ID |
|---|---|---|
| 924 | PHE0000832 | 27400 |
| 932 | PHE0000840 | 27401 |
| 957 | PHE0000865 | 27402 |
| 961 | PHE0000869 | 27403 |
| 1001 | PHE0000913 | 27404 |
| 1015 | PHE0000927 | 27405 |
| 1016 | PHE0000928 | 27406 |
| 1026 | PHE0000938 | 27407 |
| 1027 | PHE0000939 | 27408 |
| 1032 | PHE0000944 | 27409 |
| 1033 | PHE0000945 | 27410 |
| 1036 | PHE0000948 | 27411 |
| 1043 | PHE0000955 | 27412 |
| 1044 | PH E0000956 | 27413 |
| 1045 | PHE0000957 | 27414 |
| 1051 | PHE0000963 | 27415 |
| 1054 | PHE0000966 | 27416 |
| 1059 | PHE0000972 | 27417 |
| 1087 | PHE0001006 | 27418 |
| 1119 | PHE0001039 | 27419 |
| 1123 | PHE0001043 | 27420 |
| 1135 | PHE0001162 | 27421 |
| 1136 | PHE0001163 | 27422 |
| 1137 | PHE0001164 | 27423 |
| 1138 | PHE0001165 | 27424 |
| 1139 | PHE0001166 | 27425 |
| 1165 | PHE0001435 | 27426 |

DETAILED DESCRIPTION OF THE INVENTION

As used herein a "plant cell" means a plant cell that is transformed with stably-integrated, non-natural, recombinant DNA, e.g. by *Agrobacterium*-mediated transformation or by bombardment using microparticles coated with recombinant DNA or other means. A plant cell of this invention can be an originally-transformed plant cell that exists as a microorganism or as a progeny plant cell that is regenerated into differentiated tissue, e.g. into a transgenic plant with stably-integrated, non-natural recombinant DNA, or seed or pollen derived from a progeny transgenic plant.

As used herein a "transgenic plant" means a plant whose genome has been altered by the stable integration of recombinant DNA. A transgenic plant includes a plant regenerated from an originally-transformed plant cell and progeny transgenic plants from later generations or crosses of a transformed plant.

As used herein "recombinant DNA" means DNA which has been a genetically engineered and constructed outside of a cell including DNA containing naturally occurring DNA or cDNA or synthetic DNA.

As used herein "consensus sequence" means an artificial sequence of amino acids in a conserved region of an alignment of amino acid sequences of homologous proteins, e.g. as determined by a CLUSTALW alignment of amino acid sequence of homolog proteins.

As used herein a "homolog" means a protein in a group of proteins that perform the same biological function, e.g. proteins that belong to the same Pfam protein family and that provide a common enhanced trait in transgenic plants of this invention. Homologs are expressed by homologous genes. Homologous genes include naturally occurring alleles and artificially-created variants. Degeneracy of the genetic code provides the possibility to substitute at least one base of the protein encoding sequence of a gene with a different base without causing the amino acid sequence of the polypeptide produced from the gene to be changed. Hence, a useful polynucleotide may have base sequence changes from SEQ ID NO:1 through SEQ ID NO: 614 in accordance with degeneracy of the genetic code. Homologs are proteins that, when optimally aligned, have at least 60% identity, more preferably about 70% or higher, more preferably at least 80% and even more preferably at least 90% identity, e.g. 95 to 98% identity, over the full length of a protein identified as being associated with imparting an enhanced trait when expressed in plant cells. Homologs include proteins with an amino acid sequence that have at least 90% identity, e.g. at least 95 to 98% identity, to a consensus amino acid sequence of proteins and homologs disclosed herein.

Homologs are identified by comparison of amino acid sequence, e.g. manually or by use of a computer-based tool using known homology-based search algorithms such as those commonly known and referred to as BLAST, FASTA, and Smith-Waterman. A local sequence alignment program, e.g. BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit is a likely ortholog, when the reciprocal query's best hit is the query protein itself or a protein encoded by a duplicated gene after speciation. A further aspect of the invention comprises functional homolog proteins that differ in one or more amino acids from those of disclosed protein as the result of conservative amino acid substitutions, for example substitutions are among: acidic (negatively charged) amino acids such as aspartic acid and glutamic acid; basic (positively charged) amino acids such as arginine, histidine, and lysine; neutral polar amino acids such as glycine, serine, threonine, cysteine, tyrosine, asparagine, and glutamine; neutral nonpolar (hydrophobic) amino acids such as alanine, leucine, isoleucine, valine, proline, phenylalanine, tryptophan, and methionine; amino acids having aliphatic side chains such as glycine, alanine, valine, leucine, and isoleucine; amino acids having aliphatic-hydroxyl side chains such as serine and threonine; amino acids having amide-containing side chains such as asparagine and glutamine; amino acids having aromatic side chains such as phenylalanine, tyrosine, and tryptophan; amino acids having basic side chains such as lysine, arginine, and histidine; amino acids having sulfur-containing side chains such as cysteine and methionine; naturally conservative amino acids such as valine-leucine, valine-isoleucine, phenylalanine-tyrosine, lysine-arginine, alanine-valine, aspartic acid-glutamic acid, and asparagine-glutamine. A further aspect of the homologs encoded by DNA useful in the transgenic plants of the invention are those proteins that differ from a disclosed protein as the result of deletion or insertion of one or more amino acids in a native sequence.

As used herein, "percent identity" means the extent to which two optimally aligned DNA or protein segments are invariant throughout one or more windows of alignment of components, for example nucleotide sequence or amino acid sequence, allowing for gaps to account to insertions and deletions. An "identity fraction" for aligned segments of a test sequence and a reference sequence is the number of identical components that are shared by sequences of the two aligned segments divided by the total number of sequence components in the aligned parts of the reference segment over window(s) of alignment which is the smaller of the full test sequence or the full reference sequence. "Percent identity" ("% identity") is the identity fraction times 100.

The "Pfam" database is a large collection of multiple sequence alignments and hidden Markov models covering many common protein families, e.g. Pfam version 19.0 (December 2005) contains alignments and models for 8183 protein families and is based on the Swissprot 47.0 and SP-TrEMBL 30.0 protein sequence databases. See S. R. Eddy, "Profile Hidden Markov Models", *Bioinformatics* 14:755-763, 1998. The Pfam database is currently maintained and updated by the Pfam Consortium. The alignments represent some evolutionary conserved structure that has implications for the protein's function. Profile hidden Markov models (profile HMMs) built from the protein family alignments are useful for automatically recognizing that a new protein belongs to an existing protein family even if the homology by alignment appears to be low.

A "Pfam domain module" is a representation of Pfam domains in a protein, in order from N terminus to C terminus. In a Pfam domain module individual Pfam domains are separated by double colons "::". The order and copy number of the Pfam domains from N to C terminus are attributes of a Pfam domain module. Although the copy number of repetitive domains is important, varying copy number often enables a similar function. Thus, a Pfam domain module with multiple copies of a domain should define an equivalent Pfam domain module with variance in the number of multiple copies. A Pfam domain module is not specific for distance between adjacent domains, but contemplates natural distances and variations in distance that provide equivalent function. The Pfam database contains both narrowly- and broadly-defined domains, leading to identification of overlapping domains on some proteins. A Pfam domain module is characterized by non-overlapping domains. Where there is overlap, the domain having a function that is more closely associated with the function of the protein (based on the E value of the Pfam match) is selected.

Once one DNA is identified as encoding a protein which imparts an enhanced trait when expressed in transgenic plants, other DNA encoding proteins with the same Pfam domain module are identified by querying the amino acid sequence of protein encoded by candidate DNA against the Hidden Markov Models which characterizes the Pfam domains using HMMER software, a current version of which is provided in the appended computer listing. Candidate proteins meeting the same Pfam domain module are in the protein family and have cognate DNA that is useful in constructing recombinant DNA for the use in the plant cells of this invention. Hidden Markov Model databases for use with HMMER software in identifying DNA expressing protein with a common Pfam domain module for recombinant DNA in the plant cells of this invention are also included in the appended computer listing. Version 19.0 of the HMMER software and Pfam databases were used to identify known domains in the proteins corresponding to amino acid sequence of SEQ ID NO: 615 through SEQ ID NO: 1228. All DNA encoding proteins that have scores higher than the gathering cutoff disclosed in Table 23 by Pfam analysis disclosed herein can be used in recombinant DNA of the plant cells of this invention, e.g. for selecting transgenic plants having enhanced agronomic traits. The relevant Pfams modules for use in this invention, as more specifically disclosed below, are DUF6::DUF6, Sterol_desat, HMG_box, GAF::HisKA::HATPase_c, Sugar_tr, Mito_carr::Mito_carr::Mito_carr, RRM_1, 14-3-3, Globin, F-box::Kelch_1::Kelch_2::Kelch_1::Kelch_2::Kelch_2, Pkinase, zf-CHY::zf-C3HC4, AUX_IAA, Cu-oxidase_3::Cu-oxidase::Cu-oxidase_2, Sigma70_r2::Sigma70_r3::Sigma70_r4, AT_hook:: DUF296, Exo_endo_phos, H_PPase, Aldo_ket_red, CHASE::HisKA::HATPase_c::Response_reg, Myb_DNA-binding, AP2::AP2, Flavodoxin_2, P-II, zf-CCCH::zf-CCCH::KH_1::zf-CCCH, PSK, adh_short, Myb_DNA-binding::Myb_DNA-binding, FLO_LFY, LRR_1::LRR_1:: LRR_1::LRR_1::LRR_1::LRR_1::LRR_1::LRR_1:: LRR_1::LRR_1::LRR_1::LRR_1::LRR_1::LRR_1:: LRR_1::LRR_1::Pkinase, Zein, Response_reg::Myb_DNA-binding, LEA_4, DAD, DUF6::DUF6, F-box::LRR_2, LEA_2, zf-C3HC4, 2OG-FeII_Oxy, WD40::WD40, DUF231, Cullin, CBFD_NFYB_HMF, Histone, U-box, HSF_DNA-bind, GH3, LIM::LIM, RPE65, GST_N:: GST_C, IMPDH, Mlo, Copine, Rieske::PaO, ADH_N:: ADH_zinc_N, PBP, F-box, Prp19::WD40::WD40::WD40, Glycos_transf_1::S6PP, PfkB, ABA_WDS, AP2, Asp, Hydrolase, OPT, TFIIS::TFIIS_M::TFTIIS_C, Peptidase_C14, TPT, NAM, SRF-TF::K-box, G-alpha, Lactamase_B, LRR_2::LRR_2, PTR2, PB1, Pkinase::Pkinase_C, S-methyl_trans, Phytochrome::HisKA::HATPase_c, Ank:: Ank::Ank::Ank::Ank::zf-C3HC4, F-box::Kelch_2:: Kelch_2::Kelch_1::Kelch_2, Cyclin_N, Dor1, F-box:: LRR_1, BCCT, B_lectin::S_locus_glycop::PAN_2::Pkinase, SAC3_GANP, F-box::Kelch_1::Kelch_1::Kelch_1, DUF6, MFMR::bZIP_1, Skp1_POZ::Skp1, U-box::Arm::Arm:: Arm, NAF1, Ribosomal_L18p, SET, F-box::LysM, Pyridoxal_deC, PPDK_N::PEP-utilizers::PEP-utilizers_C, Transket_pyr::Transketolase_C, IPP-2, zf-B_box::zf-B_box:: CCT, MFS_1, zf-D of, RRM_1::zf-CCHC, F-box::Tub, SATase_N::Hexapep::Hexapep::Hexapep, PEMT, B_lectin:: PAN_2::Pkinase, Peptidase_S10, SOH1, Methyltransf_11, bZIP_1, DXP_reductoisom::DXP_redisom_C, Flavoprotein, MatE::MatE, Homeobox::HALZ, U-box::Arm::Arm:: Arm::Arm::Arm, zf-B_box::zf-B_box, Glycos_transf_1, zf-LSD1::zf-LSD1::zf-LSD1, Aldedh, Melibiase, HEAT:: HEAT::HEAT::FAT::Rapamycin_bind::PI3_PI4_kinase:: FATC, MtN3_slv::MtN3_slv, DUF1313, S6PP, HD-ZIP_N:: Homeobox::HALZ, WRKY, FBPase_glpX, MIF4G:: MIF4G_like::MIF4G_like_2, zf-B_box::CCT, FAD_binding_4, Hpt, TLC, CK_II_beta, TPR_1::TPR_1:: TPR_2::U-box, Response_reg, AdoHcyase_NAD, P1-PLC-X::PI-PLC-Y::C2, Pkinase::Ribonuc_2-5A, Globin:: FAD_binding_6::NAD_binding_1, PMEI, Myb_DNA-binding::Linker_histone, LRRNT_2::LRR_1::LRR_1::LRR_1:: LRR_1::LRR_1::LRR_1::LRR_1::LRR_1::LRR_1:: LRR_1::LRR_1::LRR_1::LRR_1::LRR_1::LRR_1:: LRR_1::LRR_1::LRR_1::LRR_1::LRR_1::LRR_1:: Pkinase, Pkinase::efhand::efhand::efhand::efhand, Pescadillo_N::BRCT, SPX::zf-C3HC4, AdoHcyase, zf-CCCH::zf-CCCH::zf-CCCH::zf-CCCH::zf-CCCH, SBP56, DUF850, NAS, UPF0005, Alpha-amylase::Alpha-amyl_C2, Na_H_Exchanger, PAN_1::Pkinase, F-box:: Kelch_1::Kelch_1, Remorin_C, Skp1, DUF580, zf-C2H2, zf-LSD1::Peptidase_C14, Ribosomal_L10:: Ribosomal_60s, Frigida, Methyltransf_11::Methyltransf_11, dCMP_cyt_deam_1, DUF914, Enolase_N::Enolase_C, p450, Cellulose_synt, Cu_bind_like, S6PP:: S6PP_C, BRAP2::zf-C3HC4::zf-UBP, BIR::BIR, C1_1:: DAGK_cat::DAGK_acc, PA::zf-C3HC4, DPBB_1:: Pollen_allerg_1, LRRNT_2::LRR_1::LRR_1::LRR_1:: LRR_1::LRR_1::LRR_1::LRR_1::LRR_1::LRR_1:: LRR_1::LRR_1::LRR_11::LRR_1::LRR_11::LRR_1:: LRR_1::LRR_1::Pkinase, WD40::WD40::WD40::WD40:: WD40::WD40, bZIP_2, FBPase, HLH, GRAS, SBP, Sina, Remorin_N::Remorin_C, BTB::NPH3, Glutaredoxin, AA_permease, Cyclin_N::Cyclin_C, DUF810, LRR_2, B_ectin::S_locus_glycop::PAN_2::PAN_1::Pkinase, Put_Phosphatase, DUF221, Response_reg::CCT, EMP24_GP25L, VDE, Orn_Arg_deC_N::Orn_DAP_Arg_deC, HEAT::HEAT::HEAT::HEAT::HEAT::HEAT::HEAT, PHD, UPF0041, Bromodomain, Bap31, UDPGP, Pkinase::NAF, Pirin::Pirin_C, MED7.

As used herein "promoter" means regulatory DNA for initializing transcription. A "plant promoter" is a promoter capable of initiating transcription in plant cells whether or not its origin is a plant cell, e.g. is it well known that *Agrobacterium* promoters are functional in plant cells. Thus, plant promoters include promoter DNA obtained from plants, plant viruses and bacteria such as *Agrobacterium* and *Bradyrhizobium* bacteria. Examples of promoters under developmental control include promoters that preferentially initiate transcription in certain tissues, such as leaves, roots, or seeds. Such promoters are referred to as "tissue preferred". Promoters that initiate transcription only in certain tissues are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions, or certain chemicals, or the presence of light. Tissue specific, tissue preferred, cell type specific, and inducible promoters constitute the class of "non-constitutive" promoters. A "constitutive" promoter is a promoter which is active under most conditions.

As used herein "operably linked" means the association of two or more DNA fragments in a DNA construct so that the function of one, e.g. protein-encoding DNA, is controlled by the other, e.g. a promoter.

As used herein "expressed" means produced, e.g. a protein is expressed in a plant cell when its cognate DNA is transcribed to mRNA that is translated to the protein.

As used herein a "control plant" means a plant that does not contain the recombinant DNA that expressed a protein that impart an enhanced trait. A control plant is to identify and select a transgenic plant that has an enhance trait. A suitable control plant can be a non-transgenic plant of the parental line used to generate a transgenic plant, i.e. devoid of recombinant DNA. A suitable control plant may in some cases be a progeny of a hemizygous transgenic plant line that is does not contain the recombinant DNA, known as a negative segregant.

As used herein an "enhanced trait" means a characteristic of a transgenic plant that includes, but is not limited to, an enhance agronomic trait characterized by enhanced plant morphology, physiology, growth and development, yield, nutritional enhancement, disease or pest resistance, or environmental or chemical tolerance. In more specific aspects of this invention enhanced trait is selected from group of enhanced traits consisting of enhanced water use efficiency, enhanced cold tolerance, increased yield, enhanced nitrogen use efficiency, enhanced seed protein and enhanced seed oil. In an important aspect of the invention the enhanced trait is enhanced yield including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. "Yield" can be affected by many properties including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Yield can also be affected by efficiency of germination (including germination in stressed conditions), growth rate (including growth rate in stressed conditions), ear number, seed number per ear, seed size, composition of seed (starch, oil, protein) and characteristics of seed fill.

Increased yield of a transgenic plant of the present invention can be measured in a number of ways, including test weight, seed number per plant, seed weight, seed number per unit area (i.e. seeds, or weight of seeds, per acre), bushels per acre, tons per acre, kilo per hectare. For example, maize yield may be measured as production of shelled corn kernels per unit of production area, for example in bushels per acre or metric tons per hectare, often reported on a moisture adjusted basis, for example at 15.5 percent moisture. Increased yield may result from improved utilization of key biochemical compounds, such as nitrogen, phosphorous and carbohydrate, or from improved responses to environmental stresses, such as cold, heat, drought, salt, and attack by pests or pathogens. Recombinant DNA used in this invention can also be used to provide plants having improved growth and development, and ultimately increased yield, as the result of modified expression of plant growth regulators or modification of cell cycle or photosynthesis pathways. Also of interest is the generation of transgenic plants that demonstrate enhanced yield with respect to a seed component that may or may not correspond to an increase in overall plant yield. Such properties include enhancements in seed oil, seed molecules such as tocopherol, protein and starch, or oil particular oil components as may be manifest by an alteration in the ratios of seed components.

A subset of the nucleic molecules of this invention includes fragments of the disclosed recombinant DNA consisting of oligonucleotides of at least 15, preferably at least 16 or 17, more preferably at least 18 or 19, and even more preferably at least 20 or more, consecutive nucleotides. Such oligonucleotides are fragments of the larger molecules having a sequence selected from the group consisting of SEQ ID NO:1 through SEQ ID NO: 614, and find use, for example as probes and primers for detection of the polynucleotides of the present invention.

DNA constructs are assembled using methods well known to persons of ordinary skill in the art and typically comprise a promoter operably linked to DNA, the expression of which provides the enhanced agronomic trait. Other construct components may include additional regulatory elements, such as 5' leaders and introns for enhancing transcription, 3' untranslated regions (such as polyadenylation signals and sites), DNA for transit or signal peptides.

Numerous promoters that are functional in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens*, caulimovirus promoters from the cauliflower mosaic virus. For instance, see U.S. Pat. Nos. 5,858,742 and 5,322,938, which disclose versions of the constitutive promoter derived from cauliflower mosaic virus (CaMV35S), U.S. Pat. No. 5,641,876, which discloses a rice actin promoter, U.S. Patent Application Publication 2002/0192813A1, which discloses 5', 3' and intron elements useful in the design of effective plant expression vectors, U.S. patent application Ser. No. 09/757,089, which discloses a maize chloroplast aldolase promoter, U.S.

patent application Ser. No. 08/706,946, which discloses a rice glutelin promoter, U.S. patent application Ser. No. 09/757,089, which discloses a maize aldolase (FDA) promoter, and U.S. Patent Application Ser. No. 60/310,370, which discloses a maize nicotianamine synthase promoter, all of which are incorporated herein by reference. These and numerous other promoters that function in plant cells are known to those skilled in the art and available for use in recombinant polynucleotides of the present invention to provide for expression of desired genes in transgenic plant cells.

In other aspects of the invention, preferential expression in plant green tissues is desired. Promoters for such use include those from genes such as *Arabidopsis thaliana* ribulose-1,5-bisphosphate carboxylase (Rubisco) small subunit (Fischhoff et al. (1992) *Plant Mol. Biol.* 20:81-93), aldolase and pyruvate orthophosphate dikinase (PPDK) (Taniguchi et al. (2000) *Plant Cell Physiol.* 41(1):42-48).

A promoter may be altered to contain multiple "enhancer sequences" to assist in elevating gene expression. Such enhancers are known in the art. By including an enhancer sequence with a promoter, expression may be enhanced. These enhancers often are found 5' to the start of transcription in a promoter that functions in eukaryotic cells, but can often be inserted upstream (5') or downstream (3') to the coding sequence. In some instances, these 5' enhancing elements are introns. Particularly useful as enhancers are the 5' introns of the rice actin 1 (see U.S. Pat. No. 5,641,876) and rice actin 2 genes, the maize alcohol dehydrogenase gene intron, the maize heat shock protein 70 gene intron (U.S. Pat. No. 5,593,874) and the maize shrunken 1 gene.

In other aspects of the invention, sufficient expression in plant seed tissues is desired to affect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell et al. (1997) *Transgenic Res.* 6(2): 157-166), globulin 1 (Belanger et al (1991) *Genetics* 129:863-872), glutelin 1 (Russell supra), and peroxiredoxin antioxidant (Per1) (Stacy et al. (1996) *Plant Mol Biol.* 31(6):1205-1216).

Recombinant DNA constructs prepared in accordance with the invention will also generally include a 3' element that typically contains a polyadenylation signal and site. Well-known 3' elements include those from *Agrobacterium tumefaciens* genes such as nos 3', tml 3', tmr 3', tms 3', ocs 3', tr7 3', for example disclosed in U.S. Pat. No. 6,090,627, incorporated herein by reference; 3' elements from plant genes such as wheat (*Triticum aesevitum*) heat shock protein 17 (Hsp17 3'), a wheat ubiquitin gene, a wheat fructose=1,6-biphosphatase gene, a rice glutelin gene, a rice lactate dehydrogenase gene and a rice beta-tubulin gene, all of which are disclosed in U.S. published patent application 2002/0192813 A1, incorporated herein by reference; and the pea (*Pisum sativum*) ribulose biphosphate carboxylase gene (rbs 3'), and 3' elements from the genes within the host plant.

Constructs and vectors may also include a transit peptide for targeting of a gene to a plant organelle, particularly to a chloroplast, leucoplast or other plastid organelle. For descriptions of the use of chloroplast transit peptides see U.S. Pat. No. 5,188,642 and U.S. Pat. No. 5,728,925, incorporated herein by reference.

Transgenic plants comprising or derived from plant cells of this invention transformed with recombinant DNA can be further enhanced by incorporating DNA providing other traits, e.g. herbicide and/or pest resistance traits. DNA for insect resistance can be derived from *Bacillus thuringensis* to provide resistance against lepidopteran, coliopteran, homopteran, hemiopteran, and other insects. DNA for herbicide resistance can provide resistance to glyphosate, dicamba, glufosinate, sulfonylurea, bromoxynil or norflurazon herbicides. For example, DNA encoding 5-enolpyruvylshikimate-3-phosphate synthase (EPSPS) disclosed in U.S. Pat. Nos. 5,094,945; 5,627,061; 5,633,435 and 6,040,497 can impart glyphosate tolerance; DNA encoding a glyphosate oxidoreductase (GOX) disclosed in U.S. Pat. No. 5,463,175 and a glyphosate-N-acetyl transferase (GAT) disclosed in U.S. Patent Application publication 2003/0083480 A1 can also impart glyphosate tolerance; DNA encoding a dicamba monooxygenase disclosed in U.S. Patent Application publication 2003/0135879 A1 can impart dicamba tolerance; DNA encoding bromoxynil nitrilase (Bxn) disclosed in U.S. Pat. No. 4,810,648 can impart bromoxynil tolerance; DNA encoding phytoene desaturase (crtI) described in Misawa et al, (1993) *Plant J.* 4:833-840 can impart norflurazon tolerance; DNA encoding acetohydroxyacid synthase described in Sathasiivan et al. (1990) *Nucl. Acids Res.* 18:2188-2193 can impart sulfonylurea herbicide tolerance; DNA encoding a BAR protein as disclosed in DeBlock, et al. (1987) *EMBO J.* 6:2513-2519 can impart glufosinate and bialaphos tolerance; DNA disclosed in U.S. Patent Application Publication 2003/010609 A1 can impart N-amino methyl phosphonic acid tolerance; DNA disclosed in U.S. Pat. No. 6,107,549 can impart pyridine herbicide resistance; DNA molecules and methods for imparting tolerance to multiple herbicides such as glyphosate, atrazine, ALS inhibitors, isoxoflutole and glufosinate herbicides are disclosed in U.S. Pat. No. 6,376,754 and U.S. Patent Application Publication 2002/0112260, all of said U.S. patents and Patent Application Publications are incorporated herein by reference. Molecules and methods for imparting insect/nematode/virus resistance are disclosed in U.S. Pat. Nos. 5,250,515; 5,880,275; 6,506,599; 5,986,175 and U.S. Patent Application Publication 2003/0150017 A1, all of which are incorporated herein by reference.

Plant Cell Transformation Methods

Numerous methods for transforming plant cells with recombinant DNA are known in the art and may be used to make the transgenic plants, cells and nuclei of this invention. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 6,384,301 (soybean), U.S. Pat. No. 7,026,528 (wheat) and U.S. Pat. No. 6,329,571 (rice), all of which are incorporated herein by reference. For *Agrobacterium tumefaciens* based plant transformation systems, additional elements present on transformation constructs will include T-DNA left and right border sequences to facilitate incorporation of the recombinant polynucleotide into the plant genome.

In general it is useful to introduce recombinant DNA randomly, i.e. at a non-specific location, in the genome of a target plant line. In special cases it may be useful to target recombinant DNA insertion in order to achieve site-specific integration, for example, to replace an existing gene in the genome, to use an existing promoter in the plant genome, or to insert a recombinant polynucleotide at a predetermined site known to be active for gene expression. Several site specific recombination systems exist which are known to function in plants including cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" refers to the numerous nutrient mixtures that are used to grow cells in vitro, that is, outside of the intact living organism. Recipient cell targets include, but are not limited to, meristem cells, hypocotyls, calli, immature embryos and gametic cells such as microspores, pollen, sperm and egg cells. It is contemplated that any cell from which a fertile plant may be regenerated is useful as a recipient cell. Callus may be initiated from tissue sources including, but not limited to, immature embryos, hypocotyls, seedling apical meristems, microspores and the like. Cells capable of proliferating as callus are also recipient cells for genetic transformation. Practical transformation methods and materials for making transgenic plants of this invention, for example various media and recipient target cells, transformation of immature embryo cells and subsequent regeneration of fertile transgenic plants are disclosed in U.S. Pat. Nos. 6,194,636 and 6,232,526, which are incorporated herein by reference.

The seeds of transgenic plants can be harvested from fertile transgenic plants and be used to grow progeny generations of transformed plants of this invention including hybrid plants line for selection of plants having an enhanced trait. In addition to direct transformation of a plant with a recombinant DNA, transgenic plants can be prepared by crossing a first plant having a recombinant DNA with a second plant lacking the DNA. For example, recombinant DNA can be introduced into a first plant line that is amenable to transformation to produce a transgenic plant which can be crossed with a second plant line to introgress the recombinant DNA into the second plant line. A transgenic plant with recombinant-DNA providing an enhanced trait, e.g. enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g. marker identification by analysis for recombinant DNA or, in the case where a selectable marker is linked to the recombinant, by application of the selecting agent such as a herbicide for use with a herbicide tolerance marker, or by selection for the enhanced trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line.

In the practice of transformation DNA is typically introduced into chromosomes in the nuclei of only a small percentage of target plant cells in any one transformation experiment. Marker genes are used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this invention may be resistant are useful agents for selective markers. Plant cells containing potentially transformed nuclei are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV); spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318; 5,633,435; 5,780,708 and 6,118,047, all of which are incorporated herein by reference. Selectable markers which provide an ability to visually identify transformants can also be employed, for example, a gene expressing a colored or fluorescent protein such as a luciferase or green fluorescent protein (GFP) or a gene expressing a beta-glucuronidase or uidA gene (GUS) for which various chromogenic substrates are known.

Plant cells that survive exposure to the selective agent, or plant cells that have been scored positive in a screening assay, may be cultured in regeneration media and allowed to mature into plants having the transformed nuclei. Developing plantlets regenerated from transformed plant cells can be transferred to plant growth mix, and hardened off, for example, in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are regenerated from about 6 weeks to 10 months after a transformant is identified, depending on the initial tissue, and the plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of enhanced agronomic trait.

Transgenic Plants and Seeds

Transgenic plants derived from the plant cells of this invention are grown to generate transgenic plants having an enhanced trait as compared to a control plant and produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased yield or other trait that provides increased plant value, including, for example, improved seed quality. Of particular interest are plants having enhanced water use efficiency, enhanced cold tolerance, increased yield, enhanced nitrogen use efficiency, enhanced seed protein and enhanced seed oil.

Table 2 provides a list of proteins SEQ ID NO: 615 through SEQ ID NO: 1228 encoding DNA ("genes") that are useful as recombinant DNA for production of transgenic plants with enhanced agronomic trait.

Column headings in Table 2 refer to the following information: "PEP SEQ ID" refers to a particular number of amino acid sequence in the Sequence Listing. "PHE ID" refers to an arbitrary number used to identify a particular recombinant polynucleotide corresponding to the translated protein encoded by the polynucleotide. "NUC SEQ ID" refers to a particular number of a nucleic acid sequence in the Sequence Listing which defines a polynucleotide used in a recombinant polynucleotide of this invention. "GENE NAME" refers to a common name for the recombinant polynucleotide. "GENE EFFECT" refers to the effect of the expressed polypeptide in providing yield improvement or other enhanced property. "CODING SEQUENCE" refers to peptide coding segments of the polynucleotide. "SPECIES" refers to the organism from which the polynucleotide DNA was derived.

TABLE 2

| PEP SEQ ID | PHE ID | NUC SEQ ID | Gene Name | Gene Effect | Coding Sequence | Species |
|---|---|---|---|---|---|---|
| 615 | PHE0000002 | 1 | *Arabidopsis* AtHAP3a | Stress tolerance | 103-525 | *Arabidopsis thaliana* |
| 616 | PHE0000003 | 2 | corn AtHAP3a-like1 | Stress tolerance | 149-817 | *Zea mays* |
| 617 | PHE0000004 | 3 | corn AtHAP3a-like2 | Stress tolerance | 196-750 | *Zea mays* |
| 618 | PHE0000005 | 4 | corn AtHAP3a-like3 | Stress tolerance | 91-588 | *Zea mays* |
| 619 | PHE0000021 | 5 | *Arabidopsis* CCA1 | Stress tolerance | 238-2061 | *Arabidopsis thaliana* |
| 620 | PHE0000041 | 6 | corn hemoglobin 2 | Stress tolerance | 67-639 | *Zea mays* |
| 621 | PHE0000066 | 7 | At TOR1-like | Stress tolerance | 1462-1626, 1850-2188, 2267-2341, 2519-2691, 3060-3158, 3442-3634, 3703-3846, 3984-4153, 4233-4437, 4511-4699, 4907-5059, 5528-5649, 5735-5837, 5912-6007, 6309-6439, 7148-7250, 7326-7508, 7583-7675, 7914-8012, 8096-8194, 8247-8451, 8764-8888, 8999-9051, 9493-9616, 9734-9904, 10380-10532, 10599-10751, 11235-11306, 11414-11548, 11625-11686, 11819-11916, 12172-12281, 12358-12531, 12647-12712, 13059-13127, 13235-13345, 13685-13825, 13917-14045, 14168-14333, 14421-14629, 14795-15001, 15165-15278, 15383-15613, 15896-15976, 16081-16155, 16234-16300, 16400-16560, 16707-16880, 16967-17095, 17187-17270, 17379-17440, 17521-17593, 17678-18001, 18086-18385 | *Arabidopsis thaliana* |
| 622 | PHE0000078 | 8 | *E. coli* glnB | Carbon and/or nitrogen metabolism | 35-373 | *Escherichia coli* |
| 623 | PHE0000080 | 9 | G28/BAA32418 | Stress tolerance | 3-803 | *Arabidopsis thaliana* |
| 624 | PHE0000081 | 10 | G378 | Stress tolerance | 1-723 | *Arabidopsis thaliana* |
| 625 | PHE0000094 | 11 | G464 | Stress tolerance | 41-661 | *Arabidopsis thaliana* |
| 626 | PHE0000112 | 12 | Curly Leaf-variant 1 | Apomixis | 108-901, 1084-1177, 1251-3055 | *Zea mays* |
| 627 | PHE0000113 | 13 | Curly Leaf-variant 2 | Apomixis | 113-912, 1083-1191, 1257-2806 | *Zea mays* |
| 628 | PHE0000140 | 14 | casein kinase II alpha subunit | Flower development | 202-1200 | *Zea mays* |
| 629 | PHE0000151 | 15 | Adenosylhomo cysteinase | Stress tolerance | 71-1525 | *Zea mays* |
| 630 | PHE0000199 | 16 | ethylene response sensor | Ethylene signaling | 79-1986 | *Zea mays* |
| 631 | PHE0000214 | 17 | maize glycine rich protein | Stress tolerance | 70-540 | *Zea mays* |
| 632 | PHE0000364 | 18 | wilt-like 1 | Stress tolerance | 316-1644 | *Zea mays* |
| 633 | PHE0000365 | 19 | wilt-like 2 | Stress tolerance | 334-1512 | *Zea mays* |
| 634 | PHE0000366 | 20 | wilt-like 3 | Stress tolerance | 263-1552 | *Zea mays* |
| 635 | PHE0000367 | 21 | wilt-like 4 | Stress tolerance | 202-1419 | *Zea mays* |
| 636 | PHE0000373 | 23 | G1411 | Plant growth and development | 1-747 | *Arabidopsis thaliana* |
| 637 | PHE0000374 | 24 | G1449 | Plant growth and development | 1-474 | *Arabidopsis thaliana* |
| 638 | PHE0000375 | 25 | G1635 | Plant growth and development | 1-1161 | *Arabidopsis thaliana* |
| 639 | PHE0000376 | 26 | G188 | Stress tolerance | 1-1044 | *Arabidopsis thaliana* |
| 640 | PHE0000377 | 27 | G19 | Stress tolerance | 1-747 | *Arabidopsis thaliana* |

TABLE 2-continued

| PEP SEQ ID | PHE ID | NUC SEQ ID | Gene Name | Gene Effect | Coding Sequence | Species |
|---|---|---|---|---|---|---|
| 641 | PHE0000378 | 28 | G559 | Plant growth and development | 1-1194 | Arabidopsis thaliana |
| 642 | PHE0000379 | 29 | G865 | Plant growth and development | 1-636 | Arabidopsis thaliana |
| 643 | PHE0000381 | 30 | corn G214 | Stress tolerance | 1-2160 | Zea mays |
| 644 | PHE0000383 | 31 | 700151210_FLI-corn L5 a | Plant growth and development | 61-966 | Zea mays |
| 645 | PHE0000384 | 32 | LIB3957-023-C10_FLI-corn C-type cyclin | Plant growth and development | 134-904 | Zea mays |
| 646 | PHE0000405 | 33 | ASH2-F17I14_190 (Suppressor of hog1) | Stress tolerance | 370-1965 | Arabidopsis thaliana |
| 647 | PHE0000406 | 34 | soy ASH2-like 1 | Stress tolerance | 67-1329 | Glycine max |
| 648 | PHE0000407 | 35 | soy ASH2-like 3 | Stress tolerance | 37-1464 | Glycine max |
| 649 | PHE0000408 | 36 | soy ASH2-like 4 | Stress tolerance | 49-1971 | Glycine max |
| 650 | PHE0000409 | 37 | corn pescadillo-like 1 | Plant growth and development | 55-1911 | Zea mays |
| 651 | PHE0000410 | 38 | yeast pescadillo homologue-Z72888 | Plant growth and development | 657-2474 | Saccharomyces cerevisiae |
| 652 | PHE0000424 | 39 | soy GA2-oxidase | Plant growth and development | 38-1036 | Glycine max |
| 653 | PHE0000447 | 40 | corn phospholipase C 1 | Stress tolerance | 228-1985 | Zea mays |
| 654 | PHE0000448 | 41 | corn diacylglycerol kinase 2 | Stress tolerance | 141-2282 | Zea mays |
| 655 | PHE0000449 | 42 | corn Ins(1,4,5)P(3) 5-phosphatase 1 | Stress tolerance | 116-1849 | Zea mays |
| 656 | PHE0000459 | 43 | Anabaena SPP | Carbon and/or nitrogen metabolism | 1-747 | Nostoc PCC7120 |
| 657 | PHE0000460 | 44 | Corn SPP | Carbon and/or nitrogen metabolism | 1-1269 | Zea mays |
| 658 | PHE0000461 | 45 | UDPgpp | Carbon and/or nitrogen metabolism | 1-1419 | Zea mays |
| 659 | PHE0000464 | 46 | soy U-box protein 1 | Plant growth and development | 137-2119 | Glycine max |
| 660 | PHE0000465 | 47 | soy U-box protein 2 | Plant growth and development | 63-1355 | Glycine max |
| 661 | PHE0000466 | 48 | soy U-box protein 3 | Plant growth and development | 26-2053 | Glycine max |
| 662 | PHE0000467 | 49 | corn U-box protein 3 | Plant growth and development | 197-1774 | Zea mays |
| 663 | PHE0000468 | 50 | corn U-box protein 4 | Plant growth and development | 104-1183 | Zea mays |
| 664 | PHE0000474 | 51 | yeast ado1 | Stress tolerance | 567-1589 | Saccharomyces cerevisiae |
| 665 | PHE0000475 | 52 | corn adenosine kinase 1 | Stress tolerance | 264-1289 | Zea mays |
| 666 | PHE0000476 | 53 | soy adenosine kinase 2 | Stress tolerance | 90-1112 | Glycine max |
| 667 | PHE0000477 | 54 | Synechocystis hypothetical sugar kinase-BAA10827 | Stress tolerance | 86-1087 | Synechocystis sp. PCC 6803 |
| 668 | PHE0000478 | 55 | corn adenosylhomocysteinase 1 | Stress tolerance | 38-1492 | Zea mays |
| 669 | PHE0000479 | 56 | yeast S-adenosyl-L-homocysteine hydrolase-NP_010961 | Stress tolerance | 142-1491 | Saccharomyces cerevisiae |
| 670 | PHE0000480 | 57 | Synechocystis S-adenosylhomocysteine hydrolase-BAA18079 | Stress tolerance | 305-1582 | Synechocystis sp. PCC 6803 |
| 671 | PHE0000481 | 58 | soy RING finger protein 1 [BCRA1] | Plant growth and development | 64-1494 | Glycine max |
| 672 | PHE0000482 | 59 | Aspergillus yA (laccase 1)-X52552 | Stress tolerance | 913-1107, 1162-1217, 1289-1459, 1535-1705, 1759-1884, 1949-3059 | Emericella nidulans |
| 673 | PHE0000483 | 60 | Synechocystis Sucrose phosphate synthase | Carbon and/or nitrogen metabolism | 1-2160 | Synechocystis sp. PCC 6803 |
| 674 | PHE0000487 | 61 | yeast HAL3-Z28297 | Plant growth and development | 64-1752 | Saccharomyces cerevisiae |
| 675 | PHE0000488 | 62 | yeast GLC8-P41818 | Plant growth and development | 2556-3245 | Saccharomyces cerevisiae |
| 676 | PHE0000489 | 63 | corn HAL3-like 1-LIB3060-046-G12_FLI | Plant growth and development | 24-659 | Zea mays |

TABLE 2-continued

| PEP SEQ ID | PHE ID | NUC SEQ ID | Gene Name | Gene Effect | Coding Sequence | Species |
|---|---|---|---|---|---|---|
| 677 | PHE0000490 | 64 | corn HAL3-like 2- | Plant growth and development | 237-881 | *Zea mays* |
| 678 | PHE0000491 | 65 | corn GLC8-like 2 | Plant growth and development | 232-726 | *Zea mays* |
| 679 | PHE0000492 | 66 | corn GLC8-like 1 | Plant growth and development | 98-625 | *Zea mays* |
| 680 | PHE0000495 | 69 | *Agrobacterium* aiiA-like protein [attM]-AAD43990 | Stress tolerance | 98-865 | *Agrobacterium tumefaciens* |
| 681 | PHE0000496 | 70 | *Xylella* aiiA-like protein-XF1361 | Stress tolerance | 365-1204 | *Xylella fastidiosa* |
| 682 | PHE0000497 | 71 | *Xanthomonas* aiiA-like protein | Stress tolerance | 121-1044 | |
| 683 | PHE0000498 | 72 | corn histone H4 | Seed development | 83-391 | *Zea mays* |
| 684 | PHE0000499 | 73 | high sulfur zein protein precursor | Seed development | 29-661 | *Zea mays* |
| 685 | PHE0000500 | 74 | corn RING finger protein 25 | Plant growth and development | 353-1771 | *Zea mays* |
| 686 | PHE0000501 | 75 | corn MKP 1 [MAP kinase 4] | Signal transduction | 157-1278 | *Zea mays* |
| 687 | PHE0000502 | 76 | corn MKP 3 [MAP kinase 5] | Signal transduction | 110-1300 | *Zea mays* |
| 688 | PHE0000503 | 77 | corn MKP 4 | Signal transduction | 76-1185 | *Zea mays* |
| 689 | PHE0000504 | 78 | corn MKP 6 | Signal transduction | 411-2174 | *Zea mays* |
| 690 | PHE0000505 | 79 | corn MKP 7 | Signal transduction | 382-1854 | *Zea mays* |
| 691 | PHE0000506 | 80 | corn MKP 8 [cdc2 kinase] | Signal transduction | 217-1098 | *Zea mays* |
| 692 | PHE0000507 | 81 | soy MKP 1 | Signal transduction | 175-1293 | *Glycine max* |
| 693 | PHE0000508 | 82 | soy MKP 4 | Signal transduction | 334-1446 | *Glycine max* |
| 694 | PHE0000509 | 83 | corn ABF2-like 1 | Stress tolerance | 141-350, 440-1315 | *Zea mays* |
| 695 | PHE0000510 | 84 | soy ABF2-like 1 | Stress tolerance | 114-1046 | *Glycine max* |
| 696 | PHE0000511 | 85 | maize PPDK | Carbon and/or nitrogen metabolism | 131-3043 | *Zea mays* |
| 697 | PHE0000512 | 86 | yeast YOR161c-Z75069 | Stress tolerance | 1002-2621 | *Saccharomyces cerevisiae* |
| 698 | PHE0000513 | 87 | yeast HNM1-Z72599 | Stress tolerance | 419-2110 | *Saccharomyces cerevisiae* |
| 699 | PHE0000514 | 88 | *Xylella* SAG13-like-E82748 | Plant growth and development | 67-843 | *Xylella fastidiosa* |
| 700 | PHE0000515 | 89 | corn SAG13-like 1 | Plant growth and development | 74-862 | *Zea mays* |
| 701 | PHE0000516 | 90 | soy SAG13-like 1 | Plant growth and development | 49-855 | *Glycine max* |
| 702 | PHE0000517 | 91 | soy SAG13-like 2 | Plant growth and development | 25-837 | *Glycine max* |
| 703 | PHE0000518 | 92 | *Nostoc punctiforme* SAG13-like | Plant growth and development | 68-853 | *Nostoc punctiforme* |
| 704 | PHE0000520 | 93 | corn clavata3-like | Plant growth and development | 145-384 | *Zea mays* |
| 705 | PHE0000521 | 94 | corn clavata3-like | Plant growth and development | 22-255 | *Zea mays* |
| 706 | PHE0000523 | 96 | corn clv3-like 2 | Plant growth and development | 69-356 | *Zea mays* |
| 707 | PHE0000525 | 98 | corn violaxanthin de-epoxidase | Stress tolerance | 77-1414 | *Zea mays* |
| 708 | PHE0000526 | 99 | rice serine acetyltransferase 1 | Stress tolerance | 51-1070 | *Oryza sativa* |
| 709 | PHE0000527 | 100 | rice serine acetyltranferase 2 | Stress tolerance | 131-1192 | *Oryza sativa* |
| 710 | PHE0000528 | 101 | corn CEO-like protein | Stress tolerance | 134-1873 | *Zea mays* |
| 711 | PHE0000529 | 102 | wheat nicotianamine aminotransferase | Iron uptake | 43-1041 | *Triticum aestivum* |
| 712 | PHE0000530 | 103 | corn nicotianamine synthase 1 | Iron uptake | 55-1146 | *Zea mays* |
| 713 | PHE0000531 | 104 | corn ys1-like1 | Iron uptake | 277-2292 | *Zea mays* |
| 714 | PHE0000532 | 105 | rice glutamate decarboxylase | Plant growth and development | 77-1552 | *Oryza sativa* |
| 715 | PHE0000533 | 106 | rice GA2 oxidase | Plant growth and development | 74-1219 | *Oryza sativa* |

TABLE 2-continued

| PEP SEQ ID | PHE ID | NUC SEQ ID | Gene Name | Gene Effect | Coding Sequence | Species |
|---|---|---|---|---|---|---|
| 716 | PHE0000534 | 107 | corn mlo-like 1 | Plant growth and development | 57-1583 | Zea mays |
| 717 | PHE0000535 | 108 | corn G alpha 1 | Plant growth and development | 220-1329 | Zea mays |
| 718 | PHE0000536 | 109 | corn G beta 2 | Plant growth and development | 58-1059 | Zea mays |
| 719 | PHE0000537 | 110 | corn g gamma-like 1 | Plant growth and development | 64-407, 514-655 | Zea mays |
| 720 | PHE0000538 | 111 | rice tubby 1 | Plant growth and development | 4-1221 | Oryza sativa |
| 721 | PHE0000539 | 112 | maize tubby 3 | Plant growth and development | 49-1122 | Zea mays |
| 722 | PHE0000540 | 113 | maize tubby 4 | Plant growth and development | 257-1600 | Zea mays |
| 723 | PHE0000541 | 114 | corn tubby 5 | Plant growth and development | 100-1200 | Zea mays |
| 724 | PHE0000542 | 115 | maize tubby 6 | Plant growth and development | 83-1390 | Zea mays |
| 725 | PHE0000543 | 116 | maize tubby 7 | Plant growth and development | 125-1327 | Zea mays |
| 726 | PHE0000544 | 117 | corn tubby 9 | Plant growth and development | 333-1700 | Zea mays |
| 727 | PHE0000545 | 118 | rice LRR.F-box protein 1 | Plant growth and development | 83-1867 | Oryza sativa |
| 728 | PHE0000546 | 119 | corn LRR.F-box protein 7 | Plant growth and development | 167-1936 | Zea mays |
| 729 | PHE0000547 | 120 | cotton ttg1-1 | Stress tolerance | 19-1056 | Gossypium hirsutum |
| 730 | PHE0000548 | 121 | corn nucellin-like protein 1 | Seed development | 42-1424 | Zea mays |
| 731 | PHE0000549 | 122 | rice nucellin-like protein 1 | Seed development | 37-1443 | Oryza sativa |
| 732 | PHE0000550 | 123 | rice G1449-like 1 | Plant growth and development | 107-652 | Oryza sativa |
| 733 | PHE0000551 | 124 | rice LEA 1 | Stress tolerance | 87-686 | Oryza sativa |
| 734 | PHE0000552 | 125 | rice LEA 2 [wsi18] | Stress tolerance | 70-714 | Oryza sativa |
| 735 | PHE0000553 | 126 | corn LEA 1 | Stress tolerance | 94-1008 | Zea mays |
| 736 | PHE0000554 | 127 | corn LEA 2 | Stress tolerance | 85-777 | Zea mays |
| 737 | PHE0000555 | 128 | corn adenylate transporter 1 | Plant growth and development | 49-1938 | Zea mays |
| 738 | PHE0000556 | 129 | Xylella adenylate transporter-XF1738 | Plant growth and development | 54-1376 | Xylella fastidiosa |
| 739 | PHE0000557 | 130 | yeast AAC2-Z35791 | Plant growth and development | 66-1022 | Saccharomyces cerevisiae |
| 740 | PHE0000558 | 131 | yeast TFS1-X62105 | Flower development | 16-675 | Saccharomyces cerevisiae |
| 741 | PHE0000559 | 132 | yeast YLR179C-AAB67472 | Flower development | 124-729 | Saccharomyces cerevisiae |
| 742 | PHE0000560 | 133 | ZmSPS2-2 | Carbon and/or nitrogen metabolism | 29-2920 | Zea mays |
| 743 | PHE0000561 | 134 | rice FPF1-like 1 | Flower development | 93-458 | Oryza sativa |
| 744 | PHE0000562 | 135 | rice FPF1-like 3 | Flower development | 60-413 | Oryza sativa |
| 745 | PHE0000563 | 136 | corn FPF1-like 1 | Flower development | 132-473 | Zea mays |
| 746 | PHE0000564 | 137 | corn FPF1-like 6 | Flower development | 31-345 | Zea mays |
| 747 | PHE0000565 | 138 | corn FLC-like 3 | Flower development | 210-905 | Zea mays |
| 748 | PHE0000566 | 139 | corn FLC-like 9 | Flower development | 305-976 | Zea mays |
| 749 | PHE0000567 | 140 | corn selenium-binding protein | Stress tolerance | 239-1717 | Zea mays |
| 750 | PHE0000568 | 141 | maize glutathione S-transferase IV | Stress tolerance | 103-771 | Zea mays |
| 751 | PHE0000569 | 142 | calcium-dependent protein kinase | Stress tolerance | 177-1844 | Zea mays |
| 752 | PHE0000570 | 143 | protein kinase CK2 regulatory subunit CK2B3 | Stress tolerance | 178-993 | Zea mays |
| 753 | PHE0000571 | 144 | 19K zein precursor | Stress tolerance | 46-747 | Zea mays |
| 754 | PHE0000572 | 145 | corn EREBP/AP2-like transcription factor | Stress tolerance | 114-1196 | Zea mays |
| 755 | PHE0000573 | 146 | G-box binding factor 1 | Stress tolerance | 145-1275 | Zea mays |

TABLE 2-continued

| PEP SEQ ID | PHE ID | NUC SEQ ID | Gene Name | Gene Effect | Coding Sequence | Species |
|---|---|---|---|---|---|---|
| 756 | PHE0000574 | 147 | corn high mobility group protein | Stress tolerance | 145-615 | Zea mays |
| 757 | PHE0000575 | 148 | corn glycine-rich RNA-binding protein | Stress tolerance | 70-492 | Zea mays |
| 758 | PHE0000576 | 149 | corn enolase 1 | Stress tolerance | 86-1423 | Zea mays |
| 759 | PHE0000577 | 150 | maize RING finger protein | Stress tolerance | 72-680 | Zea mays |
| 760 | PHE0000578 | 151 | maize 60S acidic ribosomal protein P0 | Stress tolerance | 123-1079 | Zea mays |
| 761 | PHE0000579 | 152 | corn nucleotide-binding protein | Stress tolerance | 223-1266 | Zea mays |
| 762 | PHE0000580 | 153 | MADS affecting flowering 1-AAK37527 | Flower development | 31-618 | Arabidopsis thaliana |
| 763 | PHE0000581 | 154 | G1760-Q9SZJ6 | Flower development | 50-733 | Arabidopsis thaliana |
| 764 | PHE0000582 | 155 | G2010-CAB56582 | Flower development | 1-522 | Arabidopsis thaliana |
| 765 | PHE0000583 | 156 | SAG13-AAF09487 | Plant growth and development | 1-903 | Arabidopsis thaliana |
| 766 | PHE0000584 | 157 | Rice SAG13-like | Plant growth and development | 7-786 | Oryza sativa |
| 767 | PHE0000585 | 158 | corn FLT-like 1 | Flower development | 317-835 | Zea mays |
| 768 | PHE0000586 | 159 | corn FLT-like 2 | Flower development | 65-595 | Zea mays |
| 769 | PHE0000587 | 160 | corn FLT-like 3 | Flower development | 72-263, 626-994 | Zea mays |
| 770 | PHE0000588 | 161 | rice leafy-AB005620 | Flower development | 76-1245 | Oryza sativa |
| 771 | PHE0000589 | 162 | corn HD1-like 1 | Flower development | 93-926 | Zea mays |
| 772 | PHE0000590 | 163 | rice plastidic ATP/ADP-transporter-BAB40979 | Plant growth and development | 109-915, 2211-2480, 2563-2706, 2792-3145, 3591-3950 | Oryza sativa |
| 773 | PHE0000591 | 164 | rice L5 a | Plant growth and development | 80-991 | Oryza sativa |
| 774 | PHE0000592 | 165 | corn L5 | Plant growth and development | 61-966 | Zea mays |
| 775 | PHE0000593 | 166 | corn L5-like | Plant growth and development | 8-871 | Zea mays |
| 776 | PHE0000594 | 167 | Agrobacterium ornithine decarboxylase | Plant growth and development | 24-1562 | Agrobacterium tumefaciens |
| 777 | PHE0000601 | 168 | corn IAP-like RING finger protein 1 | Plant growth and development | 179-1291 | Zea mays |
| 778 | PHE0000603 | 170 | corn BAX inhibitor 1-like 1 | Plant growth and development | 157-906 | Zea mays |
| 779 | PHE0000604 | 171 | corn Bax inhibitor 1-like 2 | Plant growth and development | 113-697 | Zea mays |
| 780 | PHE0000605 | 172 | corn Bax inhibitor 1-like 3 | Plant growth and development | 144-890 | Zea mays |
| 781 | PHE0000606 | 173 | corn caspase-like 1 | Plant growth and development | 141-1193 | Zea mays |
| 782 | PHE0000607 | 174 | corn caspase-like 2 | Plant growth and development | 86-1018 | Zea mays |
| 783 | PHE0000608 | 175 | corn caspase-like 3 | Plant growth and development | 74-1141 | Zea mays |
| 784 | PHE0000609 | 176 | yeast YOR197w | Plant growth and development | 186-1547 | Saccharomyces cerevisiae |
| 785 | PHE0000610 | 177 | soy Lls1-like | Plant growth and development | 7-1695 | Glycine max |
| 786 | PHE0000611 | 178 | Synechocystis Rieske iron-sulfur protein | Plant growth and development | 38-1447 | Synechocystis sp. PCC 6803 |
| 787 | PHE0000612 | 179 | Arabidopsis AGL15 | Plant growth and development | 80-892 | Arabidopsis thaliana |
| 788 | PHE0000613 | 180 | yeast OST2 | Plant growth and development | 24-425 | Saccharomyces cerevisiae |
| 789 | PHE0000614 | 181 | corn DAD1 | Plant growth and development | 72-413 | Zea mays |
| 790 | PHE0000615 | 182 | corn pirin | Plant growth and development | 98-1222 | Zea mays |
| 791 | PHE0000616 | 183 | corn betaine-aldehyde dehydrogenase | Stress tolerance | 17-1531 | Zea mays |
| 792 | PHE0000617 | 184 | rice betaine aldehyde dehydrogenase | Stress tolerance | 93-1610 | Oryza sativa |

TABLE 2-continued

| PEP SEQ ID | PHE ID | NUC SEQ ID | Gene Name | Gene Effect | Coding Sequence | Species |
|---|---|---|---|---|---|---|
| 793 | PHE0000618 | 185 | yeast PEM1/CHO2 | Stress tolerance | 617-3226 | Saccharomyces cerevisiae |
| 794 | PHE0000619 | 186 | yeast PEM2/OPI3 | Stress tolerance | 160-780 | Saccharomyces cerevisiae |
| 795 | PHE0000620 | 187 | corn phosphoethanolamine N-methyltransferase 2 | Stress tolerance | 392-1894 | Zea mays |
| 796 | PHE0000621 | 188 | E. coli betT | Stress tolerance | 36-2069 | Escherichia coli |
| 797 | PHE0000622 | 189 | Xenorhabdus BetT-like 1 | Stress tolerance | 29-2068 | Xenorhabdus sp. |
| 798 | PHE0000623 | 190 | corn NHX1-like 1 | Stress tolerance | 38-1675 | Zea mays |
| 799 | PHE0000624 | 191 | OsNHX1-AB021878 | Stress tolerance | 297-1904 | Oryza sativa |
| 800 | PHE0000625 | 192 | corn vacuolar H+-pyrophosphatase 1 | Stress tolerance | 124-2409 | Zea mays |
| 801 | PHE0000626 | 193 | corn vacuolar H+-pyrophosphatase 2 | Stress tolerance | 93-2390 | Zea mays |
| 802 | PHE0000627 | 194 | corn vacuolar H+-pyrophosphatase 5 | Stress tolerance | 35-2329 | Zea mays |
| 803 | PHE0000628 | 195 | soy homeobox-leucine zipper protein homolog h1- | Light response | 66-920 | Glycine max |
| 804 | PHE0000629 | 196 | soy zinc finger protein | Light response | 98-622 | Glycine max |
| 805 | PHE0000630 | 197 | soy TGACG-motif-binding protein STF2 | Light response | 82-1053 | Glycine max |
| 806 | PHE0000631 | 198 | corn putative zinc finger protein | Light response | 225-842 | Zea mays |
| 807 | PHE0000632 | 199 | soy AP2 domain transcription factor | Light response | 227-928 | Glycine max |
| 808 | PHE0000633 | 200 | soy pseudo-response regulator | Light response | 27-2060 | Glycine max |
| 809 | PHE0000634 | 201 | soy CONSTANS-like B-box zinc finger protein | Light response | 108-1229 | Glycine max |
| 810 | PHE0000635 | 202 | soy RPT2-like | Light response | 23-1762 | Glycine max |
| 811 | PHE0000636 | 203 | corn myb-related protein | Light response | 34-1101 | Zea mays |
| 812 | PHE0000637 | 204 | Arabidopsis salt-tolerance protein | Light response | 274-1017 | Arabidopsis thaliana |
| 813 | PHE0000638 | 205 | soy AP2 domain transcription factor | Light response | 98-1555 | Glycine max |
| 814 | PHE0000639 | 206 | soy late elongated hypocotyl | Light response | 626-2875 | Glycine max |
| 815 | PHE0000640 | 207 | soy zinc finger protein | Light response | 139-1416 | Glycine max |
| 816 | PHE0000641 | 208 | soy putative protein kinase | Light response | 73-1764 | Glycine max |
| 817 | PHE0000642 | 209 | soy auxin-responsive GH3 protein | Light response | 42-1820 | Glycine max |
| 818 | PHE0000643 | 210 | corn ripening-related protein | Light response | 131-775 | Zea mays |
| 819 | PHE0000644 | 211 | corn beta-expansin 4 | Light response | 97-1020 | Zea mays |
| 820 | PHE0000645 | 212 | corn hypothetical protein | Light response | 330-716 | Zea mays |
| 821 | PHE0000646 | 213 | corn unknown protein | Light response | 69-710 | Zea mays |
| 822 | PHE0000647 | 214 | corn unknown protein | Light response | 234-563 | Zea mays |
| 823 | PHE0000648 | 215 | corn unknown protein | Light response | 169-1542 | Zea mays |
| 824 | PHE0000649 | 216 | soy unknown protein | Light response | 585-1889 | Glycine max |
| 825 | PHE0000650 | 217 | corn unknown protein | Light response | 211-2514 | Zea mays |
| 826 | PHE0000651 | 218 | rice Lls1 (CAO)-AF284781 | Light response | 100-1722 | Oryza sativa |
| 827 | PHE0000654 | 219 | G896 | Plant growth and development | 47-1147 | Arabidopsis thaliana |
| 828 | PHE0000655 | 220 | G1435 | Plant growth and development | 8-901 | Arabidopsis thaliana |
| 829 | PHE0000656 | 221 | LIB4074-003-H1__FLI-corn G1435-like | Plant growth and development | 83-856 | Zea mays |
| 830 | PHE0000658 | 222 | G1496 | Plant growth and development | 116-1120 | Arabidopsis thaliana |
| 831 | PHE0000660 | 223 | 700072387__FLI-ZmSPS3-1 | Carbon and/or nitrogen metabolism | 89-3265 | Zea mays |
| 832 | PHE0000661 | 224 | GATE90-ZmSPS2-3 | Carbon and/or nitrogen metabolism | 72-2987 | Zea mays |
| 833 | PHE0000662 | 225 | corn ELI17-like protein 1 | Disease resistance | 7-1350 | Zea mays |
| 834 | PHE0000663 | 226 | soy ELI17-like protein 1 | Disease resistance | 63-1355 | Glycine max |

TABLE 2-continued

| PEP SEQ ID | PHE ID | NUC SEQ ID | Gene Name | Gene Effect | Coding Sequence | Species |
|---|---|---|---|---|---|---|
| 835 | PHE0000664 | 227 | X58872-*E. coli* hmp1 | Nitric oxide signaling | 293-1483 | *Escherichia coli* |
| 836 | PHE0000665 | 228 | *Nostoc* sp. PCC 7120 glnB | Carbon and/or nitrogen metabolism | 1074-1412 | *Nostoc* PCC7120 |
| 837 | PHE0000666 | 229 | Brassica P-II | Carbon and/or nitrogen metabolism | 49-639 | *Brassica napus* |
| 838 | PHE0000700 | 230 | *Arabidopsis* eskimo 1 | Stress tolerance | 592-2052 | *Arabidopsis thaliana* |
| 839 | PHE0000701 | 231 | soy 1-deoxy-D-xylulose-5-phosphate reductoisomerase- | Isoprenoid biosynthesis | 76-1500 | *Glycine max* |
| 840 | PHE0000702 | 232 | *Synechocystis* 1-deoxy-D-xylulose-5-phosphate reductoisomerase-D64000 | Isoprenoid biosynthesis | 100-1284 | *Synechocystis* sp. PCC 6803 |
| 841 | PHE0000703 | 233 | *Agrobacterium* 1-deoxy-D-xylulose 5-phosphate reductoisomerase-AAK88334 | Isoprenoid biosynthesis | 52-1245 | *Agrobacterium tumefaciens* |
| 842 | PHE0000704 | 234 | corn 1-deoxy-D-xylulose-5-phosphate synthase- | Isoprenoid biosynthesis | 289-2445 | *Zea mays* |
| 843 | PHE0000705 | 235 | *Agrobacterium* 1-deoxy-D-xylulose-5-phosphate synthase-AAK86554 | Isoprenoid biosynthesis | 13-1932 | *Agrobacterium tumefaciens* |
| 844 | PHE0000706 | 236 | *Xylella* 1-deoxyxylulose-5-phosphate synthase-AAF85048 | Isoprenoid biosynthesis | 38-2050 | *Xylella fastidiosa* |
| 845 | PHE0000709 | 237 | corn HMT 1 (N-methyltransferase) | Stress tolerance | 102-1070 | *Zea mays* |
| 846 | PHE0000710 | 238 | corn HMT 2 (N-methyltransferase) | Stress tolerance | 94-1107 | *Zea mays* |
| 847 | PHE0000711 | 239 | *E. coli* yagD homocysteine S-methyltransferase-Q47690 | Stress tolerance | 21-953 | *Escherichia coli* |
| 848 | PHE0000712 | 240 | yeast Mht1-NP_013038 | Stress tolerance | 60-1034 | *Saccharomyces cerevisiae* |
| 849 | PHE0000713 | 241 | corn H2A.F/Z 1 | DNA integration | 102-515 | *Zea mays* |
| 850 | PHE0000714 | 242 | corn H2A 1 | DNA integration | 56-457 | *Zea mays* |
| 851 | PHE0000715 | 243 | corn H2A 3 | DNA integration | 71-541 | *Zea mays* |
| 852 | PHE0000716 | 244 | corn H2A 7 | DNA integration | 33-512 | *Zea mays* |
| 853 | PHE0000717 | 245 | wilt-1256 | Stress tolerance | 316-1980 | *Zea mays* |
| 854 | PHE0000735 | 246 | corn NAD(P)H quinone oxidoreductase | Stress tolerance | 67-834 | *Zea mays* |
| 855 | PHE0000736 | 247 | rice CBP80-AY017415 | Stress tolerance | 76-2808 | *Oryza sativa* |
| 856 | PHE0000737 | 248 | yeast GCR3-D10224 | Stress tolerance | 908-3484 | *Saccharomyces cerevisiae* |
| 857 | PHE0000738 | 249 | corn CBP20 | Stress tolerance | 8-736 | *Zea mays* |
| 858 | PHE0000739 | 250 | yeast CBC2-Z73534 | Stress tolerance | 2352-2978 | *Saccharomyces cerevisiae* |
| 859 | PHE0000740 | 251 | rice serine decarboxylase-AAG12476 | Stress tolerance | 37-289, 1008-1239, 1601-1794, 1915-2048, 2422-2621, 2796-2943, 3677-3790 | *Oryza sativa* |
| 860 | PHE0000741 | 252 | corn serine decarboxylase | Stress tolerance | 21-1376 | *Zea mays* |
| 861 | PHE0000742 | 253 | soy serine decarboxylase | Stress tolerance | 94-1542 | *Glycine max* |
| 862 | PHE0000743 | 254 | yeast DBF2-P22204 | Plant growth and development | 1-1716 | *Saccharomyces cerevisiae* |
| 863 | PHE0000744 | 255 | yeast DBF20-P32328 | Plant growth and development | 1-1692 | *Saccharomyces cerevisiae* |
| 864 | PHE0000745 | 256 | *Arabidopsis* agl8-Q38876 | Plant growth and development | 1-726 | *Arabidopsis thaliana* |
| 865 | PHE0000746 | 257 | corn AGL8-like B | Plant growth and development | 1-753 | *Zea mays* |
| 866 | PHE0000747 | 258 | corn PHR1-like 1 | Plant growth and development | 150-1496 | *Zea mays* |

TABLE 2-continued

| PEP SEQ ID | PHE ID | NUC SEQ ID | Gene Name | Gene Effect | Coding Sequence | Species |
|---|---|---|---|---|---|---|
| 867 | PHE0000748 | 259 | corn PHR1-like 2 | Plant growth and development | 55-1302 | Zea mays |
| 868 | PHE0000749 | 260 | Nitrosomonas europaea dual function SBPase/FBPase- | Carbon and/or nitrogen metabolism | 94-1095 | Nitrosomonas europaea |
| 869 | PHE0000750 | 261 | rice VP14-like 1 | Stress tolerance | 23-1936 | Oryza sativa |
| 870 | PHE0000751 | 262 | rice VP14-like 2 | Stress tolerance | 220-1947 | Oryza sativa |
| 871 | PHE0000754 | 263 | rice ANT-like | Flower development | 1-1926 | Oryza sativa |
| 872 | PHE0000755 | 264 | Nostoc sp. PCC 7120 GlpX protein | Carbon and/or nitrogen metabolism | 1-1035 | Nostoc PCC7120 |
| 873 | PHE0000756 | 265 | Nostoc punctiforme strain ATCC 29133 GlpX protein-NOS1c0617 | Carbon and/or nitrogen metabolism | 1-1035 | Nostoc punctiforme |
| 874 | PHE0000757 | 266 | Anabaena SPS C154 | Carbon and/or nitrogen metabolism | 1-1275 | Nostoc PCC7120 |
| 875 | PHE0000758 | 267 | Anabaena SPS C287 | Carbon and/or nitrogen metabolism | 1-1266 | Nostoc PCC7120 |
| 876 | PHE0000762 | 268 | G557 (HY5) | Light response | 1-507 | Arabidopsis thaliana |
| 877 | PHE0000763 | 269 | G189 | Plant growth and development | 1-951 | Arabidopsis thaliana |
| 878 | PHE0000764 | 270 | G736 | Plant growth and development | 1-510 | Arabidopsis thaliana |
| 879 | PHE0000766 | 272 | G671 | Plant growth and development | 1-1056 | Arabidopsis thaliana |
| 880 | PHE0000767 | 273 | G247 | Plant growth and development | 1-660 | Arabidopsis thaliana |
| 881 | PHE0000768 | 274 | G1384 | Plant growth and development | 1-942 | Arabidopsis thaliana |
| 882 | PHE0000769 | 275 | G779 | Plant growth and development | 1-594 | Arabidopsis thaliana |
| 883 | PHE0000770 | 276 | G1795 | Plant growth and development | 1-393 | Arabidopsis thaliana |
| 884 | PHE0000771 | 277 | G977 | Plant growth and development | 1-543 | Arabidopsis thaliana |
| 885 | PHE0000772 | 278 | G568 | Plant growth and development | 1-858 | Arabidopsis thaliana |
| 886 | PHE0000773 | 279 | G1269 | Plant growth and development | 1-861 | Arabidopsis thaliana |
| 887 | PHE0000774 | 280 | G1050 | Plant growth and development | 1-1557 | Arabidopsis thaliana |
| 888 | PHE0000779 | 281 | yeast GPA2 | Stress tolerance | 1-1347 | Saccharomyces cerevisiae |
| 889 | PHE0000796 | 282 | phytosulfokine 4-13399211 | Plant growth and development | 67-315 | Oryza sativa |
| 890 | PHE0000797 | 283 | rice phytosulfokine 2-13399209 | Plant growth and development | 107-463 | Oryza sativa |
| 891 | PHE0000798 | 284 | rice phytosulfokine-alpha-11907498 | Plant growth and development | 102-368 | Oryza sativa |
| 892 | PHE0000799 | 285 | rice phytosulphokine SH27A-3201971 | Plant growth and development | 9-314 | Oryza sativa |
| 893 | PHE0000800 | 286 | AtSUC1 | Carbon and/or nitrogen metabolism | 1-1539 | Arabidopsis thaliana |
| 894 | PHE0000801 | 287 | Arabidopsis SUT2 | Carbon and/or nitrogen metabolism | 1-1773 | Arabidopsis thaliana |
| 895 | PHE0000802 | 288 | Arabidopsis SUT4 | Carbon and/or nitrogen metabolism | 1-1530 | Arabidopsis thaliana |
| 896 | PHE0000803 | 289 | OsSUT1-D87819 | Carbon and/or nitrogen metabolism | 67-1680 | Oryza sativa |
| 897 | PHE0000804 | 290 | OsSUT3-AB071809 | Carbon and/or nitrogen metabolism | 85-1605 | Oryza sativa |
| 898 | PHE0000805 | 291 | Aspergillis phytochrome | Light response | 1-2013 | Emericella nidulans |
| 899 | PHE0000806 | 292 | corn histidine phosphotransfer protein 1 | Plant growth and development | 103-561 | Zea mays |

TABLE 2-continued

| PEP SEQ ID | PHE ID | NUC SEQ ID | Gene Name | Gene Effect | Coding Sequence | Species |
|---|---|---|---|---|---|---|
| 900 | PHE0000807 | 293 | corn histidine phosphotransfer protein 2 | Plant growth and development | 57-512 | *Zea mays* |
| 901 | PHE0000808 | 294 | soy histidine phosphotransfer protein 1 | Plant growth and development | 63-527 | *Glycine max* |
| 902 | PHE0000809 | 295 | YPD1-Z74283 | Plant growth and development | 320-823 | *Saccharomyces cerevisiae* |
| 903 | PHE0000810 | 296 | rice ethylene receptor-AF013979 | Plant growth and development | 66-1976 | *Oryza sativa* |
| 904 | PHE0000811 | 297 | rice ethylene responsive factor-AAK70909 | Plant growth and development | 9-917, 1160-1528, 1646-1912, 2188-2312, 2425-2662 | *Oryza sativa* |
| 905 | PHE0000812 | 298 | CYP79F1 (supershoot)-AF370512 | Plant growth and development | 75-1688 | *Arabidopsis thaliana* |
| 906 | PHE0000813 | 299 | AtSUC2 | Carbon and/or nitrogen metabolism | 1-1536 | *Arabidopsis thaliana* |
| 907 | PHE0000814 | 300 | soy G28 like | Stress tolerance | 1-753 | *Glycine max* |
| 908 | PHE0000815 | 301 | corn G1792-like 2 | Stress tolerance | 104-661 | *Zea mays* |
| 909 | PHE0000816 | 302 | G1792 | Stress tolerance | 77-493 | *Arabidopsis thaliana* |
| 910 | PHE0000817 | 303 | corn duf6 2 | Carbon and/or nitrogen metabolism | 54-1394 | *Zea mays* |
| 911 | PHE0000818 | 304 | corn duf6 3 | Carbon and/or nitrogen metabolism | 30-1112 | *Zea mays* |
| 912 | PHE0000819 | 305 | corn duf6 | Carbon and/or nitrogen metabolism | 62-1324 | *Zea mays* |
| 913 | PHE0000820 | 306 | corn duf6 6 | Carbon and/or nitrogen metabolism | 174-1271 | *Zea mays* |
| 914 | PHE0000822 | 307 | corn duf6 11 | Carbon and/or nitrogen metabolism | 5-1072 | *Zea mays* |
| 915 | PHE0000823 | 308 | corn duf6 12 | Carbon and/or nitrogen metabolism | 113-1261 | *Zea mays* |
| 916 | PHE0000824 | 309 | corn duf6 13 | Carbon and/or nitrogen metabolism | 48-1127 | *Zea mays* |
| 917 | PHE0000825 | 310 | corn duf6 14 | Carbon and/or nitrogen metabolism | 112-1290 | *Zea mays* |
| 918 | PHE0000826 | 311 | corn duf6 15 | Carbon and/or nitrogen metabolism | 197-1327 | *Zea mays* |
| 919 | PHE0000827 | 312 | corn duf6 16 | Carbon and/or nitrogen metabolism | 111-1142 | *Zea mays* |
| 920 | PHE0000828 | 313 | corn duf6 17 | Carbon and/or nitrogen metabolism | 6-1097 | *Zea mays* |
| 921 | PHE0000829 | 314 | corn duf6 18 | Carbon and/or nitrogen metabolism | 149-1375 | *Zea mays* |
| 922 | PHE0000830 | 315 | corn duf6 19 | Carbon and/or nitrogen metabolism | 153-1193 | *Zea mays* |
| 923 | PHE0000831 | 316 | corn duf6 20 | Carbon and/or nitrogen metabolism | 145-1641 | *Zea mays* |
| 924 | PHE0000832 | 317 | soy duf6 1 | Carbon and/or nitrogen metabolism | 52-1170 | *Glycine max* |
| 925 | PHE0000833 | 318 | soy duf6 2 | Carbon and/or nitrogen metabolism | 151-1203 | *Glycine max* |
| 926 | PHE0000834 | 319 | soy duf6 3 | Carbon and/or nitrogen metabolism | 36-1073 | *Glycine max* |
| 927 | PHE0000835 | 320 | soy duf6 4 | Carbon and/or nitrogen metabolism | 69-1118 | *Glycine max* |

TABLE 2-continued

| PEP SEQ ID | PHE ID | NUC SEQ ID | Gene Name | Gene Effect | Coding Sequence | Species |
|---|---|---|---|---|---|---|
| 928 | PHE0000836 | 321 | soy duf6 5 | Carbon and/or nitrogen metabolism | 55-1140 | *Glycine max* |
| 929 | PHE0000837 | 322 | soy duf6 6 | Carbon and/or nitrogen metabolism | 36-1271 | *Glycine max* |
| 930 | PHE0000838 | 323 | soy duf6 7 | Carbon and/or nitrogen metabolism | 228-1226 | *Glycine max* |
| 931 | PHE0000839 | 324 | soy duf6 8 | Carbon and/or nitrogen metabolism | 140-1126 | *Glycine max* |
| 932 | PHE0000840 | 325 | soy duf6 9 | Carbon and/or nitrogen metabolism | 61-1173 | *Glycine max* |
| 933 | PHE0000841 | 326 | soy duf6 10 | Carbon and/or nitrogen metabolism | 99-1265 | *Glycine max* |
| 934 | PHE0000842 | 327 | soy duf6 11 | Carbon and/or nitrogen metabolism | 167-1084 | *Glycine max* |
| 935 | PHE0000843 | 328 | soy duf6 12 | Carbon and/or nitrogen metabolism | 158-1258 | *Glycine max* |
| 936 | PHE0000844 | 329 | soy duf6 13 | Carbon and/or nitrogen metabolism | 250-1284 | *Glycine max* |
| 937 | PHE0000845 | 330 | soy duf6 15 | Carbon and/or nitrogen metabolism | 96-1157 | *Glycine max* |
| 938 | PHE0000846 | 331 | rice Crinkly4-AB057787 | Seed development | 805-3510 | *Oryza sativa* |
| 939 | PHE0000847 | 332 | rice S-domain receptor-like protein kinase 1-BAA94516 | Seed development | 89-2395 | *Oryza sativa* |
| 940 | PHE0000848 | 333 | rice S-domain receptor-like protein kinase 2-BAB07906.1 | Seed development | 89-2437 | *Oryza sativa* |
| 941 | PHE0000849 | 334 | rice S-domain receptor-like protein kinase 3-BAB07905.1 | Seed development | 98-2539 | *Oryza sativa* |
| 942 | PHE0000850 | 335 | rice S-domain receptor-like protein kinase 4-BAB07904.1 | Seed development | 72-2321 | *Oryza sativa* |
| 943 | PHE0000851 | 336 | rice S-domain receptor-like protein kinase 5 | Seed development | 28-44, 145-173, 272-397, 1180-3476 | *Oryza sativa* |
| 944 | PHE0000852 | 337 | rice S-receptor kinase PK3-BAB64641.1 | Seed development | 67-2562 | *Oryza sativa* |
| 945 | PHE0000853 | 338 | OsPK10-L27821 | Seed development | 1-2475 | *Oryza sativa* |
| 946 | PHE0000854 | 339 | soy 14-3-3 22 | Stress tolerance | 32-802 | *Glycine max* |
| 947 | PHE0000855 | 340 | soy 14-3-3 22 N-terminus | Stress tolerance | 32-382 | *Glycine max* |
| 948 | PHE0000856 | 341 | 14-3-3-like protein N-terminus | Stress tolerance | 6-365 | *Oryza sativa* |
| 949 | PHE0000857 | 342 | *sorghum* 14-3-3 10 | Stress tolerance | 116-874 | *Sorghum bicolor* |
| 950 | PHE0000858 | 343 | *sorghum* 14-3-3 10 N-terminus | Stress tolerance | 116-460 | *Sorghum bicolor* |
| 951 | PHE0000859 | 344 | rice 14-3-3 15 | Stress tolerance | 70-855 | *Oryza sativa* |
| 952 | PHE0000860 | 345 | rice 14-3-3 15 N-terminus | Stress tolerance | 70-429 | *Oryza sativa* |
| 953 | PHE0000861 | 346 | corn 14-3-3 13 | Stress tolerance | 62-808 | *Zea mays* |
| 954 | PHE0000862 | 347 | corn 14-3-3 13 N-terminus | Stress tolerance | 62-409 | *Zea mays* |
| 955 | PHE0000863 | 348 | 14-3-3 protein N-terminus | Stress tolerance | 42-389 | *Glycine max* |
| 956 | PHE0000864 | 349 | rice 14-3-3 10 | Stress tolerance | 105-875 | *Oryza sativa* |
| 957 | PHE0000865 | 350 | rice 14-3-3 10 N-terminus | Stress tolerance | 105-449 | *Oryza sativa* |
| 958 | PHE0000866 | 351 | soy 14-3-3 21 | Stress tolerance | 84-860 | *Glycine max* |
| 959 | PHE0000867 | 352 | soy 14-3-3 21 N-terminus | Stress tolerance | 84-443 | *Glycine max* |
| 960 | PHE0000868 | 353 | wheat 14-3-3 10 | Stress tolerance | 64-840 | *Triticum aestivum* |
| 961 | PHE0000869 | 354 | wheat 14-3-3 10 N-terminus | Stress tolerance | 64-420 | *Triticum aestivum* |

TABLE 2-continued

| PEP SEQ ID | PHE ID | NUC SEQ ID | Gene Name | Gene Effect | Coding Sequence | Species |
|---|---|---|---|---|---|---|
| 962 | PHE0000870 | 355 | corn 14-3-3 17 | Stress tolerance | 132-929 | Zea mays |
| 963 | PHE0000871 | 356 | corn 14-3-3 17 N-terminus | Stress tolerance | 132-506 | Zea mays |
| 964 | PHE0000872 | 357 | rice G alpha XL-BAA93022 | Plant growth and development | 48-1040, 1127-1264, 2100-2204, 2500-2682, 3113-3290, 3374-3618, 3937-4109, 4430-4627, 4988-5378 | Oryza sativa |
| 965 | PHE0000873 | 358 | yeast casein kinase II alpha-CAA86916 | Flower development | 2-1120 | Saccharomyces cerevisiae |
| 966 | PHE0000874 | 359 | rice casein kinase alpha subunit-AAL34126 | Flower development | 29-363, 471-600, 1034-1228, 2564-2721, 3082-3172, 3250-3315, 3657-3739, 3821-3884, 3967-4035, 4124-4159 | Oryza sativa |
| 967 | PHE0000875 | 360 | soy casein kinase alpha | Flower development | 129-1127 | Glycine max |
| 968 | PHE0000876 | 361 | rice casein kinase II beta subunit-AAG60201 | Flower development | 52-262, 2992-3213, 3477-3586, 3679-3844, 4365-4498 | Oryza sativa |
| 969 | PHE0000877 | 362 | yeast CKB1-Z72541 | Flower development | 286-1122 | Saccharomyces cerevisiae |
| 970 | PHE0000878 | 363 | corn casein kinase beta 1 | Flower development | 231-1055 | Zea mays |
| 971 | PHE0000879 | 364 | corn casein kinase beta 2 | Flower development | 178-993 | Zea mays |
| 972 | PHE0000884 | 365 | CAR1-like 1 | Stress tolerance | 82-546 | Zea mays |
| 973 | PHE0000885 | 366 | corn CAR1-like 3 | Stress tolerance | 161-775 | Zea mays |
| 974 | PHE0000886 | 367 | corn CAR1-like 4 | Stress tolerance | 192-659 | Zea mays |
| 975 | PHE0000887 | 368 | corn CAR1-like 5 | Stress tolerance | 86-484 | Zea mays |
| 976 | PHE0000888 | 369 | yeast hnRNP methyltransferase-CAA53689 | Stress tolerance | 76-1122 | Saccharomyces cerevisiae |
| 977 | PHE0000889 | 370 | corn arginine N-methyl transferase 1 | Stress tolerance | 44-1318 | Zea mays |
| 978 | PHE0000890 | 371 | corn arginine N-methyl transferase 2 | Stress tolerance | 102-1232 | Zea mays |
| 979 | PHE0000891 | 372 | CAR1-corn ABA inducible RNA-binding protein | Stress tolerance | 68-538 | Zea mays |
| 980 | PHE0000892 | 373 | corn RING finger 100 | Plant growth and development | 292-1404 | Zea mays |
| 981 | PHE0000893 | 374 | corn RING finger 101 | Plant growth and development | 103-1077 | Zea mays |
| 982 | PHE0000894 | 375 | corn RING finger 103 | Plant growth and development | 20-1093 | Zea mays |
| 983 | PHE0000895 | 376 | corn RING finger 102 | Plant growth and development | 252-1295 | Zea mays |
| 984 | PHE0000896 | 377 | corn RING finger 104 | Plant growth and development | 293-925 | Zea mays |
| 985 | PHE0000897 | 378 | corn RING finger 105 | Plant growth and development | 95-934 | Zea mays |
| 986 | PHE0000898 | 379 | corn RING finger 106 | Plant growth and development | 99-563 | Zea mays |
| 987 | PHE0000899 | 380 | corn RING finger 108 | Plant growth and development | 308-1054 | Zea mays |
| 988 | PHE0000900 | 381 | corn RING finger 109 | Plant growth and development | 71-622 | Zea mays |
| 989 | PHE0000901 | 382 | corn RING finger 110 [ReMembR-H2 protein JR702]- | Plant growth and development | 215-1756 | Zea mays |
| 990 | PHE0000902 | 383 | corn RING finger 111 | Plant growth and development | 162-599 | Zea mays |
| 991 | PHE0000903 | 384 | corn RING finger 112 | Plant growth and development | 411-2375 | Zea mays |
| 992 | PHE0000904 | 385 | corn RING finger 113 | Plant growth and development | 269-1828 | Zea mays |
| 993 | PHE0000905 | 386 | corn RING finger 114 | Plant growth and development | 167-781 | Zea mays |
| 994 | PHE0000906 | 387 | corn RING finger 115 | Plant growth and development | 294-806 | Zea mays |
| 995 | PHE0000907 | 388 | corn RING finger 116 | Plant growth and development | 187-1374 | Zea mays |
| 996 | PHE0000908 | 389 | corn Skp1-like 118 [UIP2] | Plant growth and development | 94-597 | Zea mays |

TABLE 2-continued

| PEP SEQ ID | PHE ID | NUC SEQ ID | Gene Name | Gene Effect | Coding Sequence | Species |
|---|---|---|---|---|---|---|
| 997 | PHE0000909 | 390 | corn Skp1-like 119 | Plant growth and development | 158-1159 | Zea mays |
| 998 | PHE0000910 | 391 | corn Skp1-like 120 [UIP2] | Plant growth and development | 106-633 | Zea mays |
| 999 | PHE0000911 | 392 | corn F-box 123 | Plant growth and development | 184-1980 | Zea mays |
| 1000 | PHE0000912 | 393 | corn F-box 124 [TIR1] | Plant growth and development | 167-1936 | Zea mays |
| 1001 | PHE0000913 | 394 | corn F-box 125 [TIR1] | Plant growth and development | 174-1892 | Zea mays |
| 1002 | PHE0000914 | 395 | corn F-box 126 | Plant growth and development | 107-1894 | Zea mays |
| 1003 | PHE0000915 | 396 | corn RING finger 128 [response regulator 6] | Plant growth and development | 42-746 | Zea mays |
| 1004 | PHE0000916 | 397 | corn RING finger 132 | Plant growth and development | 107-985 | Zea mays |
| 1005 | PHE0000917 | 398 | corn RING finger 133 | Plant growth and development | 597-1496 | Zea mays |
| 1006 | PHE0000918 | 399 | corn ASH1 | Stress tolerance | 144-899 | Zea mays |
| 1007 | PHE0000919 | 400 | corn RING finger 136 | Plant growth and development | 95-1012 | Zea mays |
| 1008 | PHE0000920 | 401 | corn RING finger 138 | Plant growth and development | 117-902 | Zea mays |
| 1009 | PHE0000921 | 402 | corn F-box 141 | Plant growth and development | 487-1428 | Zea mays |
| 1010 | PHE0000922 | 403 | corn F-box 142 | Plant growth and development | 227-1114 | Zea mays |
| 1011 | PHE0000923 | 404 | corn F-box 143 | Plant growth and development | 352-1410 | Zea mays |
| 1012 | PHE0000924 | 405 | corn F-box 144 | Plant growth and development | 96-1406 | Zea mays |
| 1013 | PHE0000925 | 406 | corn F-box 145 | Plant growth and development | 436-1524 | Zea mays |
| 1014 | PHE0000926 | 407 | corn RING finger 147 | Plant growth and development | 79-927 | Zea mays |
| 1015 | PHE0000927 | 408 | corn RING finger 149 [anaphase promoting complex subunit 11]- | Plant growth and development | 128-379 | Zea mays |
| 1016 | PHE0000928 | 409 | corn RING finger 151 [ROC1] | Plant growth and development | 77-442 | Zea mays |
| 1017 | PHE0000929 | 410 | corn U-box 153 | Plant growth and development | 166-1743 | Zea mays |
| 1018 | PHE0000930 | 411 | corn RING finger 154 [VIP2] | Plant growth and development | 262-1560 | Zea mays |
| 1019 | PHE0000931 | 412 | corn RING finger 155 [VIP2] | Plant growth and development | 161-1498 | Zea mays |
| 1020 | PHE0000932 | 413 | rice U-box 100 | Plant growth and development | 121-939 | Oryza sativa |
| 1021 | PHE0000933 | 414 | corn RING finger protein 157 | Plant growth and development | 168-857 | Zea mays |
| 1022 | PHE0000934 | 415 | corn F-box 159 [FKF1-like] | Plant growth and development | 195-2021 | Zea mays |
| 1023 | PHE0000935 | 416 | corn F-box 160 [FKF-like] | Plant growth and development | 77-1930 | Zea mays |
| 1024 | PHE0000936 | 417 | corn RING finger 161 [cellulose synthase] | Plant growth and development | 78-3026 | Zea mays |
| 1025 | PHE0000937 | 418 | corn RING finger 162 [cellulose synthase] | Plant growth and development | 193-3414 | Zea mays |
| 1026 | PHE0000938 | 419 | corn RING finger 163 | Plant growth and development | 277-1059 | Zea mays |
| 1027 | PHE0000939 | 420 | corn RING finger 164 | Plant growth and development | 218-1033 | Zea mays |
| 1028 | PHE0000940 | 421 | corn RING finger 165 | Plant growth and development | 167-754 | Zea mays |
| 1029 | PHE0000941 | 422 | corn F-box 166 | Plant growth and development | 62-814 | Zea mays |
| 1030 | PHE0000942 | 423 | corn RING finger 167 [seven in absentia-like] | Plant growth and development | 266-1288 | Zea mays |
| 1031 | PHE0000943 | 424 | corn F-box 168 | Plant growth and development | 203-1402 | Zea mays |
| 1032 | PHE0000944 | 425 | corn RING finger 169 [S-ribonuclease binding protein] | Plant growth and development | 103-1113 | Zea mays |
| 1033 | PHE0000945 | 426 | corn F-box 170 | Plant growth and development | 123-1184 | Zea mays |

TABLE 2-continued

| PEP SEQ ID | PHE ID | NUC SEQ ID | Gene Name | Gene Effect | Coding Sequence | Species |
|---|---|---|---|---|---|---|
| 1034 | PHE0000946 | 427 | corn F-box 172 | Plant growth and development | 42-803 | Zea mays |
| 1035 | PHE0000947 | 428 | corn RING finger 174 | Plant growth and development | 255-1280 | Zea mays |
| 1036 | PHE0000948 | 429 | corn RING 175 | Plant growth and development | 179-1291 | Zea mays |
| 1037 | PHE0000949 | 430 | corn Cullin 176 | Plant growth and development | 221-931 | Zea mays |
| 1038 | PHE0000950 | 431 | corn RING finger 177 | Plant growth and development | 33-863 | Zea mays |
| 1039 | PHE0000951 | 432 | corn RING finger 178 | Plant growth and development | 227-1492 | Zea mays |
| 1040 | PHE0000952 | 433 | corn RING finger 179 [alpha-galactosidase] | Plant growth and development | 68-1342 | Zea mays |
| 1041 | PHE0000953 | 434 | corn RING finger 180 | Plant growth and development | 265-1431 | Zea mays |
| 1042 | PHE0000954 | 435 | corn F-box 181 | Plant growth and development | 354-1397 | Zea mays |
| 1043 | PHE0000955 | 436 | corn RING finger 182 | Plant growth and development | 113-1282 | Zea mays |
| 1044 | PHE0000956 | 437 | corn RING finger 183 | Plant growth and development | 293-997 | Zea mays |
| 1045 | PHE0000957 | 438 | corn RING finger 185 | Plant growth and development | 104-829 | Zea mays |
| 1046 | PHE0000958 | 439 | corn F-box 186 | Plant growth and development | 47-1303 | Zea mays |
| 1047 | PHE0000959 | 440 | corn F-box 187 | Plant growth and development | 195-1199 | Zea mays |
| 1048 | PHE0000960 | 441 | corn RING/U-box 188 | Plant growth and development | 63-1142 | Zea mays |
| 1049 | PHE0000961 | 442 | corn SPS2-4 | Carbon and/or nitrogen metabolism | 105-3035 | Zea mays |
| 1050 | PHE0000962 | 443 | rice IRE1-AB031396 | Seed development | 239-2920 | Oryza sativa |
| 1051 | PHE0000963 | 444 | rice IRE1 N-terminal domain-AB031396 | Seed development | 239-1483 | Oryza sativa |
| 1052 | PHE0000964 | 445 | rice IRE1 C-terminal domain-AB031396 | Seed development | 1481-2920 | Oryza sativa |
| 1053 | PHE0000965 | 446 | yeast IRE1-P32361 | Seed development | 80-3427 | Saccharomyces cerevisiae |
| 1054 | PHE0000966 | 447 | yeast IRE1 N-terminal domain-P32361 | Seed development | 80-1798 | Saccharomyces cerevisiae |
| 1055 | PHE0000967 | 448 | yeast IRE1 C-terminal domain-P32361 | Seed development | 1799-3427 | Saccharomyces cerevisiae |
| 1056 | PHE0000968 | 449 | corn cytosine deaminase-like | Seed development | 80-1339 | Zea mays |
| 1057 | PHE0000969 | 450 | corn aldose reductase | Seed development | 106-1041 | Zea mays |
| 1058 | PHE0000970 | 451 | soy NADPH dependent mannose 6-phosphate reductase- | Seed development | 32-958 | Glycine max |
| 1059 | PHE0000972 | 453 | yeast Ydr210w-NP_010496 | Seed development | 101-325 | Saccharomyces cerevisiae |
| 1060 | PHE0000974 | 455 | yeast Soh1-NP_011388 | Seed development | 101-481 | Saccharomyces cerevisiae |
| 1061 | PHE0000975 | 456 | yeast TAD2-NP_012499 | Seed development | 101-850 | Saccharomyces cerevisiae |
| 1062 | PHE0000978 | 459 | yeast Ynl010w-NP_014388 | Seed development | 101-823 | Saccharomyces cerevisiae |
| 1063 | PHE0000979 | 460 | yeast Ynl124w-NP_014275 | Seed development | 101-1576 | Saccharomyces cerevisiae |
| 1064 | PHE0000980 | 461 | yeast Ydl124w-NP_010159 | Seed development | 101-1036 | Saccharomyces cerevisiae |
| 1065 | PHE0000984 | 465 | yeast Glutaredoxin-NP_009895 | Seed development | 101-430 | Saccharomyces cerevisiae |
| 1066 | PHE0000985 | 466 | soy unknown protein | Seed development | 228-1226 | Saccharomyces cerevisiae |
| 1067 | PHE0000986 | 467 | soy putative protein | Seed development | 265-1002 | Glycine max |
| 1068 | PHE0000987 | 468 | corn CLC1 | Stress tolerance | 102-599 | Zea mays |
| 1069 | PHE0000988 | 469 | corn CLD1 | Stress tolerance | 69-461 | Zea mays |
| 1070 | PHE0000989 | 470 | rice Asr1-AF039573 | Stress tolerance | 71-487 | Oryza sativa |
| 1071 | PHE0000990 | 471 | rice CLC1-like 1-BAB19059 | Stress tolerance | 37-326, 451-703 | Oryza sativa |
| 1072 | PHE0000991 | 472 | corn Asr1-like 1 | Stress tolerance | 151-690 | Zea mays |

TABLE 2-continued

| PEP SEQ ID | PHE ID | NUC SEQ ID | Gene Name | Gene Effect | Coding Sequence | Species |
|---|---|---|---|---|---|---|
| 1073 | PHE0000992 | 473 | corn Asr1-like 5 | Stress tolerance | 89-511 | *Zea mays* |
| 1074 | PHE0000993 | 474 | corn sigma factor 1 | Plant growth and development | 219-1715 | *Zea mays* |
| 1075 | PHE0000994 | 475 | corn sigma factor 2 [Sig3] | Plant growth and development | 166-1815 | *Zea mays* |
| 1076 | PHE0000995 | 476 | corn sigma factor 3 [Sig1] | Plant growth and development | 101-1717 | *Zea mays* |
| 1077 | PHE0000996 | 477 | corn bromodomain protein | Seed development | 417-2147 | *Zea mays* |
| 1078 | PHE0000997 | 478 | corn homeodomain leucine zipper protein | Seed development | 292-1269 | *Zea mays* |
| 1079 | PHE0000998 | 479 | corn bZIP protein 3 | Seed development | 63-908 | *Zea mays* |
| 1080 | PHE0000999 | 480 | corn bZIP protein 4 [G-box binding factor 1] | Seed development | 95-1225 | *Zea mays* |
| 1081 | PHE0001000 | 481 | corn remorin like DNA-binding protein 1 | Seed development | 84-1637 | *Zea mays* |
| 1082 | PHE0001001 | 482 | corn remorin like DNA-binding protein 2 | Seed development | 43-639 | *Zea mays* |
| 1083 | PHE0001002 | 483 | corn Gld-Tea protein 2 | Seed development | 47-811 | *Zea mays* |
| 1084 | PHE0001003 | 484 | corn homeobox protein 1 | Seed development | 370-1179 | *Zea mays* |
| 1085 | PHE0001004 | 485 | corn homeobox protein 3 | Seed development | 485-1300 | *Zea mays* |
| 1086 | PHE0001005 | 486 | corn heat shock transcription factor 1 | Seed development | 75-875 | *Zea mays* |
| 1087 | PHE0001006 | 487 | corn heat shock transcription factor 2 | Seed development | 895-1575 | *Zea mays* |
| 1088 | PHE0001007 | 488 | corn heat shock transcription factor 3 | Seed development | 195-965 | *Zea mays* |
| 1089 | PHE0001008 | 489 | corn heat shock transcription factor 4 | Seed development | 383-1276 | *Zea mays* |
| 1090 | PHE0001009 | 490 | corn IAA-like 1 | Seed development | 65-724 | *Zea mays* |
| 1091 | PHE0001010 | 491 | corn IAA-like 4 | Seed development | 762-1448 | *Zea mays* |
| 1092 | PHE0001011 | 492 | corn MADS box protein 100 | Seed development | 114-286, 383-819 | *Zea mays* |
| 1093 | PHE0001012 | 493 | corn MADS box protein 102 | Seed development | 293-1027 | *Zea mays* |
| 1094 | PHE0001013 | 494 | corn MADS box protein 103 | Seed development | 63-731 | *Zea mays* |
| 1095 | PHE0001014 | 495 | corn MADS box protein 104 | Seed development | 213-890 | *Zea mays* |
| 1096 | PHE0001015 | 496 | corn MADS box protein 105 | Seed development | 101-853 | *Zea mays* |
| 1097 | PHE0001016 | 497 | corn MADS box protein 108 | Seed development | 115-741 | *Zea mays* |
| 1098 | PHE0001018 | 498 | corn MADS box protein 114 | Seed development | 246-980 | *Zea mays* |
| 1099 | PHE0001019 | 499 | corn LIM domain protein 1 | Seed development | 99-1160 | *Zea mays* |
| 1100 | PHE0001020 | 500 | corn LIM domain protein 2 | Seed development | 171-782 | *Zea mays* |
| 1101 | PHE0001021 | 501 | corn myb-like DNA binding protein | Seed development | 248-1105 | *Zea mays* |
| 1102 | PHE0001022 | 502 | corn myb domain protein 1 | Seed development | 112-945 | *Zea mays* |
| 1103 | PHE0001023 | 503 | corn myb domain protein 3 | Seed development | 125-1030 | *Zea mays* |
| 1104 | PHE0001024 | 504 | corn myb domain protein 4 | Seed development | 34-1101 | *Zea mays* |
| 1105 | PHE0001025 | 505 | corn NAM-like protein | Seed development | 139-1563 | *Zea mays* |
| 1106 | PHE0001026 | 506 | corn transcriptional co-activator-like protein 1 | Seed development | 165-686 | *Zea mays* |
| 1107 | PHE0001027 | 507 | corn LSD1-like protein 1 | Seed development | 222-650 | *Zea mays* |
| 1108 | PHE0001028 | 508 | corn GS1-like protein | Seed development | 84-806 | *Zea mays* |
| 1109 | PHE0001029 | 509 | corn RING finger 200 | Seed development | 268-1470 | *Zea mays* |
| 1110 | PHE0001030 | 510 | corn RING finger protein 202 | Seed development | 187-1158 | *Zea mays* |

TABLE 2-continued

| PEP SEQ ID | PHE ID | NUC SEQ ID | Gene Name | Gene Effect | Coding Sequence | Species |
|---|---|---|---|---|---|---|
| 1111 | PHE0001031 | 511 | corn PGPD14-like protein | Seed development | 107-985 | Zea mays |
| 1112 | PHE0001032 | 512 | corn Ankyrin protein 1 | Seed development | 440-1891 | Zea mays |
| 1113 | PHE0001033 | 513 | corn zinc finger protein 10 [corn G325-like 3] | Seed development | 424-1644 | Zea mays |
| 1114 | PHE0001034 | 514 | corn scarecrow protein 100 | Seed development | 242-1903 | Zea mays |
| 1115 | PHE0001035 | 515 | corn transcription elongation factor | Seed development | 131-1234 | Zea mays |
| 1116 | PHE0001036 | 516 | corn constans-like protein 10 | Seed development | 128-904 | Zea mays |
| 1117 | PHE0001037 | 517 | corn copine-like protein 1 | Seed development | 518-1861 | Zea mays |
| 1118 | PHE0001038 | 518 | corn copine-like protein 2 | Seed development | 281-1513 | Zea mays |
| 1119 | PHE0001039 | 519 | corn RING finger protein 201 | Seed development | 311-1579 | Zea mays |
| 1120 | PHE0001040 | 520 | corn zinc finger protein | Seed development | 65-1138 | Zea mays |
| 1121 | PHE0001041 | 521 | corn IAA-like 10 | Seed development | 146-823 | Zea mays |
| 1122 | PHE0001042 | 522 | corn constans-like 5 | Seed development | 215-829 | Zea mays |
| 1123 | PHE0001043 | 523 | soy G-gamma subunit DC-terminus | Plant growth and development | 210-518 | Glycine max |
| 1124 | PHE0001044 | 524 | soy AGL8-like 1 | Plant growth and development | 346-1077 | Glycine max |
| 1125 | PHE0001045 | 525 | soy AGL8-like 3 | Plant growth and development | 147-863 | Glycine max |
| 1126 | PHE0001046 | 526 | corn Agl8D (LIB5131-001-H1) | Plant growth and development | 1-735 | Zea mays |
| 1127 | PHE0001047 | 527 | corn Agl8E (LIB5131-001-H2) | Plant growth and development | 1-798 | Zea mays |
| 1128 | PHE0001048 | 528 | corn Agl8F (LIB5131-001-H3) | Plant growth and development | 1-798 | Zea mays |
| 1129 | PHE0001050 | 529 | Arabidopsis LFY | Flower development | 40-1311 | Arabidopsis thaliana |
| 1130 | PHE0001103 | 530 | corn Isr | Plant growth and development | 220-1254 | Zea mays |
| 1131 | PHE0001104 | 531 | soy Isr-like 1 | Plant growth and development | 365-1495 | Glycine max |
| 1132 | PHE0001105 | 532 | rice Isr-like 1 | Plant growth and development | 110-1159 | Oryza sativa |
| 1133 | PHE0001160 | 533 | soy G1792-like | Stress tolerance | 20-391 | Glycine max |
| 1134 | PHE0001161 | 534 | corn sucrose export defective 1 (sdx1)-AF302187 | Carbon and/or nitrogen metabolism | 1-1425 | Zea mays |
| 1135 | PHE0001162 | 535 | rice sdx1 delta ctp | Carbon and/or nitrogen metabolism | 345-409, 581-692, 710-827, 2019-2098, 3567-3646, 5059-5228, 5675-5772, 6541-6645, 7487-7603, 7908-8057, 9155-9328 | Oryza sativa |
| 1136 | PHE0001163 | 536 | Arabidopsis sucrose export defective 1-AF302188 | Carbon and/or nitrogen metabolism | 1-1467 | Arabidopsis thaliana |
| 1137 | PHE0001164 | 537 | Nostoc sp. PCC 7120 sdx1-like-17134979 | Carbon and/or nitrogen metabolism | 1-1092 | Nostoc PCC7120 |
| 1138 | PHE0001165 | 538 | Synechocystis sp. PCC 6803 sdx1-like-1652844 | Carbon and/or nitrogen metabolism | 1-1092 | Synechocystis sp. PCC 6803 |
| 1139 | PHE0001166 | 539 | Nostoc punctiforme sdx1-like | Carbon and/or nitrogen metabolism | 294-1388 | Nostoc punctiforme |
| 1140 | PHE0001173 | 540 | corn CVY-CIK | Stress tolerance | 217-1563 | Zea mays |
| 1141 | PHE0001187 | 541 | corn spa1-like | Light response | 104-2467 | Zea mays |
| 1142 | PHE0001188 | 542 | corn calcium dependant protein kinase | Stress tolerance | 649-2424 | Zea mays |
| 1143 | PHE0001189 | 543 | corn unknown protein | Stress tolerance | 127-813 | Zea mays |
| 1144 | PHE0001190 | 544 | corn putative splicing factor | Stress tolerance | 153-671 | Zea mays |
| 1145 | PHE0001191 | 545 | rice hydroxyproline-rich glycoprotein | Stress tolerance | 120-1769 | Oryza sativa |

TABLE 2-continued

| PEP SEQ ID | PHE ID | NUC SEQ ID | Gene Name | Gene Effect | Coding Sequence | Species |
|---|---|---|---|---|---|---|
| 1146 | PHE0001192 | 546 | rice unknown protein-AAK14418 | Stress tolerance | 605-719, 800-864, 1161-1503, 1666-1732, 1833-1986, 2283-2450, 2553-2663, 2773-2883, 3025-3042, 3078-3179, 3748-3978, 4551-4625, 4905-4976, 5758-5943, 6029-6187, 6412-6504, 6891-6962, 7497-7587, 7830-8008, 8413-8494, 8687-8797, 8876-8982, 9355-9432, 9518-9613, 9788-9883, 11533-11700 | *Oryza sativa* |
| 1147 | PHE0001193 | 547 | corn unknown protein | Stress tolerance | 87-1147, 1229-1919 | *Zea mays* |
| 1148 | PHE0001194 | 548 | corn alpha-amylase | Stress tolerance | 553-1797 | *Zea mays* |
| 1149 | PHE0001233 | 549 | rice G1073-like 1 | Plant growth and development | 1-1008 | *Oryza sativa* |
| 1150 | PHE0001234 | 550 | rice inosine monophosphate dehydrogenase-AAK09225 | Plant growth and development | 45-1040, 2559-2738, 3841-4098, 4927-4998 | *Oryza sativa* |
| 1151 | PHE0001235 | 551 | yeast IMP dehydrogenase [Imd2p]-NP_012088 | Plant growth and development | 101-1669 | *Saccharomyces cerevisiae* |
| 1152 | PHE0001236 | 552 | *E. coli* guaB-NP_417003 | Plant growth and development | 1-1467 | *Escherichia coli* |
| 1153 | PHE0001237 | 553 | *Agrobacterium* GuaB-AE007996 | Plant growth and development | 7-1512 | *Agrobacterium tumefaciens* |
| 1154 | PHE0001276 | 554 | corn Transcription Factor #1 | Seed development | 1-921 | *Zea mays* |
| 1155 | PHE0001277 | 555 | corn Transcription Factor #2 | Seed development | 1-2028 | *Zea mays* |
| 1156 | PHE0001325 | 556 | corn RING finger protein 25 | Plant growth and development | 353-1771 | *Zea mays* |
| 1157 | PHE0001326 | 557 | yeast VHT1-YGR065C | Carbon and/or nitrogen metabolism | 101-1879 | *Saccharomyces cerevisiae* |
| 1158 | PHE0001327 | 558 | *Arabidopsis* Suc5-AJ252133 | Carbon and/or nitrogen metabolism | 63-1592 | *Arabidopsis thaliana* |
| 1159 | PHE0001400 | 559 | soy G1792-like 2 | Stress tolerance | 18-431 | *Glycine max* |
| 1160 | PHE0001401 | 560 | corn G1792-like 3 | Stress tolerance | 247-639 | *Zea mays* |
| 1161 | PHE0001423 | 561 | Glutamate Decarboxylase | Plant growth and development | 268-1761 | *Zea mays* |
| 1162 | PHE0001432 | 562 | putative carnitine/acylcarnitine translocase- | Plant growth and development | 94-909 | *Zea mays* |
| 1163 | PHE0001433 | 563 | corn cycA-like [GATE80] | Plant growth and development | 196-1230 | *Zea mays* |
| 1164 | PHE0001434 | 564 | corn cycA-like [GAT81] | Plant growth and development | 188-1306 | *Zea mays* |
| 1165 | PHE0001435 | 565 | corn E4/E8 binding protein-like [GATE68] | Plant growth and development | 253-2259 | *Zea mays* |
| 1166 | PHE0001438 | 566 | *Arabidopsis* G748 | Plant growth and development | 98-1441 | *Arabidopsis thaliana* |
| 1167 | PHE0001439 | 567 | *Arabidopsis* NAM (no apical meristem)-like protein- | Plant growth and development | 175-1293 | *Arabidopsis thaliana* |
| 1168 | PHE0001440 | 568 | soy G1452-like protein | Plant growth and development | 207-1319 | *Glycine max* |
| 1169 | PHE0001497 | 569 | corn cytochrome P450 | Plant growth and development | 143-1588 | *Zea mays* |
| 1170 | PHE0001498 | 570 | rice receptor-like protein | Plant growth and development | 1-3885 | *Oryza sativa* |
| 1171 | PHE0001499 | 571 | rice receptor-like protein kinase | Plant growth and development | 1-3333 | *Oryza sativa* |
| 1172 | PHE0001500 | 572 | rice putative brassinosteroid-insensitive protein | Plant growth and development | 1-3366 | *Oryza sativa* |
| 1173 | PHE0001501 | 573 | rice cell elongation protein DIMINUTO | Plant growth and development | 1-1686 | *Oryza sativa* |
| 1174 | PHE0001502 | 574 | corn Dwarf1-like 1 | Plant growth and development | 138-1823 | *Zea mays* |
| 1175 | PHE0001503 | 575 | rice putative sterol-C5(6)-desaturase | Plant growth and development | 1-717 | *Oryza sativa* |

TABLE 2-continued

| PEP SEQ ID | PHE ID | NUC SEQ ID | Gene Name | Gene Effect | Coding Sequence | Species |
|---|---|---|---|---|---|---|
| 1176 | PHE0001504 | 576 | corn sterol-C5(6)-desaturase 2 | Plant growth and development | 60-881 | Zea mays |
| 1177 | PHE0001505 | 577 | corn sterol-C5(6)-desaturase 1 | Plant growth and development | 43-870 | Zea mays |
| 1178 | PHE0001506 | 578 | soy sterol-C5(6)-desaturase | Plant growth and development | 158-1006 | Glycine max |
| 1179 | PHE0001507 | 579 | rice BRS1-like protease 4 | Plant growth and development | 78-1490 | Oryza sativa |
| 1180 | PHE0001508 | 580 | corn BRS1-like protease 1 | Plant growth and development | 109-1548 | Zea mays |
| 1181 | PHE0001509 | 581 | soy FKF1-like protein | Plant growth and development | 19-1878 | Glycine max |
| 1182 | PHE0001510 | 582 | corn FKF-like protein 2 | Plant growth and development | 70-2115 | Zea mays |
| 1183 | PHE0001552 | 583 | yeast YDL168W/SFA1-NP_010113 | Nitric oxide signaling | 101-1258 | Saccharomyces cerevisiae |
| 1184 | PHE0001543 | 584 | E. coli adhC-AE000142 | Nitric oxide signaling | 1-1110 | Escherichia coli |
| 1185 | PHE0001544 | 585 | Nostoc sp. PCC 7120 glutathione dependent formaldehyde dehydrogenase-BAB74509 | Nitric oxide signaling | 1-1110 | Nostoc PCC7120 |
| 1186 | PHE0001545 | 586 | rice glutathione dependent formaldehyde dehydrogenase-U77637 | Nitric oxide signaling | 204-243, 391-527, 1160-1206, 1296-1621, 1946-2028, 2107-2182, 2805-2962, 3285-3446, 3541-3657 | Oryza sativa |
| 1187 | PHE0001546 | 587 | corn glutathione-dependent formaldehyde dehydrogenase-Y11029 | Nitric oxide signaling | 82-1227 | Zea mays |
| 1188 | PHE0001547 | 588 | corn corn glutathione-dependent formaldehyde dehydrogenase 2- | Nitric oxide signaling | 108-1265 | Zea mays |
| 1189 | PHE0001548 | 589 | corn corn glutathione-dependent formaldehyde dehydrogenase 3- | Nitric oxide signaling | 95-1231 | Zea mays |
| 1190 | PHE0001549 | 590 | soy glutathione dependent formaldehyde dehydrogenase- | Nitric oxide signaling | 30-1166 | Glycine max |
| 1191 | PHE0001550 | 591 | rice putative phosphate translocator-AAK21346 | Carbon and/or nitrogen metabolism | 1-1113 | Oryza sativa |
| 1192 | PHE0001551 | 592 | rice glucose-6-phosphate/phosphate-tranlocator-13486660 | Carbon and/or nitrogen metabolism | 1-1071 | Oryza sativa |
| 1193 | PHE0001552 | 593 | corn glucose-6-phosphate/phosphate-tranlocator- | Carbon and/or nitrogen metabolism | 165-1184 | Zea mays |
| 1194 | PHE0001553 | 594 | rice putative sugar transporter-AF416867 | Carbon and/or nitrogen metabolism | 3-1736 | Oryza sativa |
| 1195 | PHE0001554 | 595 | soy cycD4-like protein | Plant growth and development | 222-1277 | Glycine max |
| 1196 | PHE0001578 | 596 | rice RPN12-AB037153 | Plant growth and development | 76-879 | Oryza sativa |
| 1197 | PHE0001579 | 597 | YFR052W/RPN12-NP_116710 | Plant growth and development | 101-922 | Saccharomyces cerevisiae |
| 1198 | PHE0001580 | 598 | corn rpn12 | Plant growth and development | 83-883 | Zea mays |
| 1199 | PHE0001581 | 599 | soy rpn12 | Plant growth and development | 113-913 | Glycine max |
| 1200 | PHE0001583 | 600 | sorghum TTG1-like | Stress tolerance | 107-1288 | Sorghum bicolor |
| 1201 | PHE0001584 | 601 | corn TTG1-like protein 2 | Stress tolerance | 141-1388 | Zea mays |
| 1202 | PHE0001595 | 602 | ZmHK1 | Plant growth and development | 77-3001 | Zea mays |
| 1203 | PHE0001596 | 603 | Arabidopsis CRE1b | Plant growth and development | 69-3311 | Arabidopsis thaliana |
| 1204 | PHE0001597 | 604 | Arabidopsis HK2 | Plant growth and development | 1-3531 | Arabidopsis thaliana |

TABLE 2-continued

| PEP SEQ ID | PHE ID | NUC SEQ ID | Gene Name | Gene Effect | Coding Sequence | Species |
|---|---|---|---|---|---|---|
| 1205 | PHE0001598 | 605 | Arabidopsis HK3 | Plant growth and development | 1-3111 | Arabidopsis thaliana |
| 1206 | PHE0001607 | 606 | maize nitrate transporter like 1 sequence | Seed development | 494-2068 | Zea mays |
| 1207 | PHE0001608 | 607 | rice nitrate transporter like 1 sequence | Seed development | 97-1698 | Oryza sativa |
| 1208 | PHE0001609 | 608 | rice nitrate transporter like 2 sequence | Seed development | 1-1551 | Oryza sativa |
| 1209 | PHE0001667 | 609 | rice histidine kinase | Plant growth and development | 201-3239 | Oryza sativa |
| 1210 | PHE0002018 | 610 | Arabidopsis nitrate transporter NTL1 like sequence | Seed development | 76-1833 | Arabidopsis thaliana |
| 1211 | PHE0002019 | 611 | maize nitrate transporter NTL1 like sequence | Seed development | 75-1907 | Zea mays |
| 1212 | PHE0002020 | 612 | maize nitrate transporter NTL1 like 2 sequence | Seed development | 212-1954 | Zea mays |
| 1213 | PHE0002021 | 613 | rice nitrate transporter NTL1 like 1 sequence | Seed development | 163-1944 | Oryza sativa |
| 1214 | PHE0002022 | 614 | rice nitrate transporter NTL1 like 2 sequence | Seed development | 1-1743 | Oryza sativa |
| 1215 | PHE0000372 | 22 | G1073 | Plant growth and development | 1-810 | Arabidopsis thaliana |
| 1216 | PHE0000493 | 67 | Synechocystis ssr3189-BAA17701 | Stress tolerance | 54-221 | Synechocystis sp. PCC 6803 |
| 1217 | PHE0000494 | 68 | Synechocystis ssr2315-BAA17190 | Stress tolerance | 242-457 | Synechocystis sp. PCC 6803 |
| 1218 | PHE0000522 | 95 | wheat clv3-like | Plant growth and development | 102-365 | Triticum aestivum |
| 1219 | PHE0000524 | 97 | corn ESR2 | Plant growth and development | 46-441 | Zea mays |
| 1220 | PHE0000602 | 169 | yeast BIR1 | Plant growth and development | 345-3209 | Saccharomyces cerevisiae |
| 1221 | PHE0000765 | 271 | G1073 | Plant growth and development | 1-810 | Arabidopsis thaliana |
| 1222 | PHE0000971 | 452 | yeast YBL107c-Z35868 | Seed development | 29-619 | Saccharomyces cerevisiae |
| 1223 | PHE0000973 | 454 | yeast YDR209c-S61572 | Seed development | 101-511 | Saccharomyces cerevisiae |
| 1224 | PHE0000976 | 457 | yeast Yet1-NP_012858 | Seed development | 101-718 | Saccharomyces cerevisiae |
| 1225 | PHE0000977 | 458 | yeast Ylr162w-NP_013263 | Seed development | 101-454 | Saccharomyces cerevisiae |
| 1226 | PHE0000981 | 462 | yeast Ygr039w-NP_011553 | Seed development | 101-409 | Saccharomyces cerevisiae |
| 1227 | PHE0000982 | 463 | yeast Usa1-NP_013683 | Seed development | 101-2614 | Saccharomyces cerevisiae |
| 1228 | PHE0000983 | 464 | yeast Ynr061c-NP_014459 | Seed development | 101-757 | Saccharomyces cerevisiae |

Selection Methods for Transgenic Plants with Enhanced Agronomic Trait

Within a population of transgenic plants regenerated from plant cells transformed with the recombinant DNA in their nucleus many plants that survive to fertile transgenic plants that produce seeds and progeny plants will not exhibit an enhanced agronomic trait. Selection from the population is necessary to identify one or more transgenic plant cells that can provide plants with the enhanced trait. Transgenic plants having enhanced traits are selected from populations of plants regenerated or derived from plant cells transformed as described herein by evaluating the plants in a variety of assays to detect an enhanced trait, e.g. enhanced water use efficiency, enhanced cold tolerance, increased yield, enhanced nitrogen use efficiency, enhanced seed protein and enhanced seed oil. These assays also may take many forms including, but not limited to, direct screening for the trait in a greenhouse or field trial or by screening for a surrogate trait. Such analyses can be directed to detecting changes in the chemical composition, biomass, physiological properties, morphology of the plant. Changes in chemical compositions such as nutritional composition of grain can be detected by analysis of the seed composition and content of protein, free amino acids, oil, free fatty acids, starch or tocopherols. Changes in biomass characteristics can be made on greenhouse or field grown plants and can include plant height, stem diameter, root and shoot dry weights; and, for corn plants, ear length and diameter. Changes in physiological properties can be identified by evaluating responses to stress conditions, for example assays using imposed stress conditions such as water deficit, nitrogen deficiency, cold growing conditions, pathogen or insect attack or light deficiency, or increased plant density. Changes in morphology can be measured by visual observation of tendency of a transformed plant with an enhanced agronomic trait to also appear to be a normal plant as compared to changes toward bushy, taller, thicker, narrower leaves, striped leaves, knotted trait, chlorosis, albino, anthocyanin production, or altered tassels, ears or roots. Other selection properties include days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barreness/prolificacy; green snap, and pest resistance. In addition, phenotypic characteristics of harvested grain may be evaluated, including number of kernels per row on the ear, number of rows of kernels on the ear, kernel abortion, kernel weight, kernel size, kernel density and physical grain quality.

Although the transgenic plant nuclei, plant cells, plant pollen, plants and methods of this invention can be applied to a wide variety of plant species such as fruits, vegetables, grasses and trees, they are particularly useful when applied to crops such as corn, soybean, cotton, oilseed rape (canola), alfalfa, rice, wheat, sugar beet, sugar cane and sunflower.

The following examples illustrate aspects of the inventions.

Example 1

Plant Expression Constructs

This example illustrates the construction of a several alternative base transformation vectors for transferring recombinant DNA into the nucleus of a plant cell which can be regenerated into a transgenic plant of this invention.

A base transformation vector for bombardment transformation is produced using GATEWAY™ Destination (Invitrogen Life Technologies, Carlsbad, Calif.) vectors. pMON65154 is constructed for use in preparation of constructs comprising recombinant polynucleotides for corn transformation. The elements of the expression vector are summarized in Table 3 below. Generally, pMON65154 comprises a selectable marker expression cassette comprising a Cauliflower Mosaic Virus 35S promoter operably linked to a gene encoding neomycin phosphotransferase II (nptII). The 3' region of the selectable marker expression cassette comprises the 3' region of the Agrobacterium tumefaciens nopaline synthase gene (nos) followed 3' by the 3' region of the potato proteinase inhibitor II (pinII) gene. The plasmid pMON 65154 further comprises a plant expression cassette into which a gene of interest may be inserted using GATEWAY™ cloning methods. The GATEWAY™ cloning cassette is flanked 5' by a rice actin 1 promoter, exon and intron and flanked 3' by the 3' region of the potato pinII gene. Using GATEWAY™ methods, the cloning cassette may be replaced with a gene of interest. The vector pMON65154, and derivatives thereof comprising a gene of interest, are particularly useful in methods of plant transformation via direct DNA delivery, such as microprojectile bombardment.

TABLE 3

Elements of Plasmid pMON65154

| FUNCTION | ELEMENT | REFERENCE |
| --- | --- | --- |
| Plant gene of interest expression cassette | Rice actin 1 promoter Rice actin 1 exon 1, intron 1 enhancer | U.S. Pat. No. 5,641,876 U.S. Pat. No. 5,641,876 |
| Gene of interest insertion site | AttR1 | GATEWAY ™Cloning Technology Instruction Manual |
| | CmR gene | GATEWAY ™Cloning Technology Instruction Manual |

TABLE 3-continued

Elements of Plasmid pMON65154

| FUNCTION | ELEMENT | REFERENCE |
| --- | --- | --- |
| | ccdA, ccdB genes | GATEWAY ™Cloning Technology Instruction Manual |
| | attR2 | GATEWAY ™Cloning Technology Instruction Manual |
| Plant gene of interest expression cassette | Potato pinII 3' region | An et al. (1989) Plant Cell 1:115-122 |
| Plant selectable marker expression cassette | CaMV 35S promoter nptII selectable marker nos 3' region PinII 3' region | U.S. Pat. No. 5,858,742 U.S. Pat. No. 5,858,742 U.S. Pat. No. 5,858,742 An et al. (1989) Plant Cell 1:115-122 |
| Maintenance in E. coli | ColE1 origin of replication F1 origin of replication Bla ampicillin resistance | |

A similar plasmid vector, pMON72472, is constructed for use in Agrobacterium-mediated methods of plant transformation. pMON72472 comprises the gene of interest plant expression cassette, GATEWAY™ cloning, and plant selectable marker expression cassettes present in pMON65154. In addition, left and right T-DNA border sequences from Agrobacterium are added to the plasmid (Zambryski et al. (1982)). The right border sequence is located 5' to the rice actin 1 promoter and the left border sequence is located 3' to the pinII 3' sequence situated 3' to the nptII gene. Furthermore, pMON72472 comprises a plasmid backbone to facilitate replication of the plasmid in both E. coli and Agrobacterium tumefaciens. The backbone has an oriV wide host range origin of DNA replication functional in Agrobacterium, a pBR322 origin of replication functional in E. coli, and a spectinomycin/streptomycin resistance gene for selection in both E. coli and Agrobacterium.

Vectors similar to those described above may be constructed for use in Agrobacterium or microprojectile bombardment maize transformation systems where the rice actin 1 promoter in the plant expression cassette portion is replaced with other desirable promoters including, but not limited to a corn globulin 1 promoter, a maize oleosin promoter, a glutelin 1 promoter, an aldolase promoter, a zein Z27 promoter, a pyruvate orthophosphate dikinase (PPDK) promoter, a soybean 7S alpha promoter, a peroxiredoxin antioxidant (Per1) promoter and a CaMV 35S promoter. Protein coding segments are amplified by PCR prior to insertion into vectors such as described above. Primers for PCR amplification can be designed at or near the start and stop codons of the coding sequence, in order to eliminate most of the 5' and 3' untranslated regions. For GATEWAY cloning methods, PCR products are tailed with attB1 and attB2 sequences, purified then recombined into a destination vectors to produce an expression vector for use in transformation.

An alternative base transformation vector specifically useful for inserting a recombinant DNA construct into a chromosome in a nucleus in a corn plant cell by Agrobacterium-mediated transformation is pMON93039 which has the DNA in the nucleotide sequence of SEQ ID NO:27374 and the elements described in Table 4 and illustrated in FIG. 2.

TABLE 4

| Function | Name | Annotation | Coordinates of SEQ ID NO: 27374 |
|---|---|---|---|
| Agrobacterium T-DNA transfer | B-AGRtu.right border | Agro right border sequence, essential for transfer of T-DNA. | 11364-11720 |
| Gene of interest expression cassette | E-Os.Act1 | Upstream promoter region of the rice actin 1 gene | 19-775 |
| | E-CaMV.35S.2xA1-B3 | Duplicated 35S A1-B3 domain without TATA box | 788-1120 |
| | P-Os.Act1 | Promoter region of the rice actin 1 gene | 1125-1204 |
| | L-Ta.Lhcb1 | 5' untranslated leader of wheat major chlorophyll a/b binding protein | 1210-1270 |
| | I-Os.Act1 | First intron and flanking UTR exon sequences from the rice actin 1 gene | 1287-1766 |
| | T-St.Pis4 | 3' non-translated region of the potato proteinase inhibitor II gene which functions to direct polyadenylation of the mRNA | 1838-2780 |
| Plant selectable marker expression cassette | P-Os.Act1 | Promoter from the rice actin 1 gene | 2830-3670 |
| | L-Os.Act1 | First exon of the rice actin 1 gene | 3671-3750 |
| | I-Os.Act1 | First intron and flanking UTR exon sequences from the rice actin 1 gene | 3751-4228 |
| | TS-At.ShkG-CTP2 | Transit peptide region of Arabidopsis EPSPS | 4238-4465 |
| | CR-AGRtu.aroA-CP4.nat | Coding region for bacterial strain CP4 native aroA gene. | 4466-5833 |
| | T-AGRtu.nos | A 3' non-translated region of the nopaline synthase gene of Agrobacterium tumefaciens Ti plasmid which functions to direct polyadenylation of the mRNA. | 5849-6101 |
| Agrobacterium T-DNA transfer | B-AGRtu.left border. | Agro left border sequence, essential for transfer of T-DNA. | 6168-6609 |
| Maintenance in E. coli | OR-Ec.oriV-RK2 | The vegetative origin of replication from plasmid RK2. | 6696-7092 |
| | CR-Ec.rop | Coding region for repressor of primer from the ColE1 plasmid. Expression of this gene product interferes with primer binding at the origin of replication, keeping plasmid copy number low. | 8601-8792 |
| | OR-Ec.ori-ColE1 | The minimal origin of replication from the E. coli plasmid ColE1. | 9220-9808 |
| | P-Ec.aadA-SPC/STR | Promoter for Tn7 adenylyltransferase (AAD(3")) | 10339-10380 |
| | CR-Ec.aadA-SPC/STR | Coding region for Tn7 adenylyltransferase (AAD(3")) conferring spectinomycin and streptomycin resistance. | 10381-11169 |
| | T-Ec.aadA-SPC/STR | 3' UTR from the Tn7 adenylyltransferase (AAD(3")) gene of E. coli. | 11170-11227 |

An alternative base transformation vector specifically useful for inserting a recombinant DNA construct into a chromosome in a nucleus in a dicot plant cell, e.g. soybean or oilseed rape, by *Agrobacterium*-mediated transformation is pMON82053 which has the DNA in the nucleotide sequence of SEQ ID NO:27375 and the elements described in Table 5 and illustrated in FIG. 3.

TABLE 5

| Function | Name | Annotation | Coordinates of SEQ ID NO: 27375 |
|---|---|---|---|
| Agrobacterium T-DNA transfer | B-AGRtu.left border | Agro left border sequence, essential for transfer of T-DNA. | 6144-6585 |
| Plant selectable marker expression cassette | P-At.Act7 | Promoter from the Arabidopsis actin 7 gene | 6624-7861 |
| | L-At.Act7 | 5'UTR of Arabidopsis Act7 gene | |
| | I-At.Act7 | Intron from the Arabidopsis actin7 gene | |

TABLE 5-continued

| Function | Name | Annotation | Coordinates of SEQ ID NO: 27375 |
|---|---|---|---|
| | TS-At.ShkG-CTP2 | Transit peptide region of Arabidopsis EPSPS | 7864-8091 |
| | CR-AGRtu.aroA-CP4.nno_At | Synthetic CP4 coding region with dicot preferred codon usage. | 8092-9459 |
| | T-AGRtu.nos | A 3' non-translated region of the nopaline synthase gene of Agrobacterium tumefaciens Ti plasmid which functions to direct polyadenylation of the mRNA. | 9466-9718 |
| Gene of interest expression cassette | P-CaMV.35S-enh | Promoter for 35S RNA from CaMV containing a duplication of the −90 to −350 region. | 1-613 |
| | T-Gb.E6-3b | 3' untranslated region from the fiber protein E6 gene of sea-island cotton. | 688-1002 |
| Agrobacterium T-DNA transfer | B-AGRtu.right border | Agro right border sequence, essential for transfer of T-DNA. | 1033-1389 |
| Maintenance in E. coli | OR-Ec.oriV-RK2 | The vegetative origin of replication from plasmid RK2. | 5661-6057 |
| | CR-Ec.rop | Coding region for repressor of primer from the ColE1 plasmid. Expression of this gene product interferes with primer binding at the origin of replication, keeping plasmid copy number low. | 3961-4152 |
| | OR-Ec.ori-ColE1 | The minimal origin of replication from the E. coli plasmid ColE1. | 2945-3533 |
| | P-Ec.aadA-SPC/STR | Promoter for Tn7 adenylyltransferase (AAD(3")) | 2373-2414 |
| | CR-Ec.aadA-SPC/STR | Coding region for Tn7 adenylyltransferase (AAD(3")) conferring spectinomycin and streptomycin resistance. | 1584-2372 |
| | T-Ec.aadA-SPC/STR | 3' UTR from the Tn7 adenylyltransferase (AAD(3")) gene of E. coli. | 1526-1583 |

An alternative base transformation vector specifically useful for inserting a recombinant DNA construct into a chromosome in a nucleus in a dicot plant cell, e.g. cotton, by Agrobacterium-mediated transformation is pMON99053 which has the DNA in the nucleotide sequence of SEQ ID NO:27376 and the elements described in Table 6 and illustrated in FIG. 4.

TABLE 6

| Function | Name | Annotation | Coordinates of SEQ ID NO: 27376 |
|---|---|---|---|
| Agrobacterium T-DNA transfer | B-AGRtu.right border | Agro right border sequence, essential for transfer of T-DNA. | 11364-11720 |
| Gene of interest expression cassette | Exp-CaMV.35S-enh + Ph.DnaK | Enhanced version of the 35S RNA promoter from CaMV plus the petunia hsp70 5' untranslated region | 7794-8497 |
| | T-Ps.RbcS2-E9 | The 3' non-translated region of the pea RbcS2 gene which functions to direct polyadenylation of the mRNA. | 67-699 |
| Plant selectable marker expression cassette | Exp-CaMV.35S | Promoter and 5' untranslated region from the 35S RNA of CaMV | 730-1053 |
| | CR-Ec.nptII-Tn5 | Coding region for neomycin phosphotransferase gene from transposon Tn5 which confers resistance to neomycin and kanamycin. | 1087-1881 |
| | T-AGRtu.nos | A 3' non-translated region of the nopaline synthase gene of Agrobacterium tumefaciens Ti plasmid which functions to direct polyadenylation of the mRNA. | 1913-2165 |
| Agrobacterium T-DNA transfer | B-AGRtu.left border | Agro left border sequence, essential for transfer of T-DNA. | 2211-2652 |
| Maintenance in E. coli | OR-Ec.oriV-RK2 | The vegetative origin of replication from plasmid RK2. | 2739-3135 |
| | CR-Ec.rop | Coding region for repressor of primer from the ColE1 plasmid. Expression | 4644-4835 |

TABLE 6-continued

| Function | Name | Annotation | Coordinates of SEQ ID NO: 27376 |
|---|---|---|---|
| | | of this gene product interferes with primer binding at the origin of replication, keeping plasmid copy number low. | |
| | OR-Ec.ori-ColE1 | The minimal origin of replication from the *E. coli* plasmid ColE1. | 5263-5851 |
| | P-Ec.aadA-SPC/STR | Promoter for Tn7 adenylyltransferase (AAD(3")) | 6382-6423 |
| | CR-Ec.aadA-SPC/STR | Coding region for Tn7 adenylyltransferase (AAD(3")) conferring spectinomycin and streptomycin resistance. | 6424-7212 |
| | T-Ec.aadA-SPC/STR | 3' UTR from the Tn7 adenylyltransferase (AAD(3")) gene of *E. coli*. | 7213-7270 |

Primers for PCR amplification of protein coding nucleotides of recombinant DNA are designed at or near the start and stop codons of the coding sequence, in order to eliminate most of the 5' and 3' untranslated regions. Each recombinant DNA coding for a protein identified in Table 2 is amplified by PCR prior to insertion into the insertion site within the gene of interest expression cassette of one of the base transformation vectors.

Example 2

Corn Transformation

This example illustrates transformation methods useful in introducing recombinant DNA into corn chromosomes to produce the transgenic nuclei, plant cells, plants and pollen and the production and identification of transgenic corn plants and seed with an enhanced trait, i.e. enhanced water use efficiency, enhanced cold tolerance, increased yield, enhanced nitrogen use efficiency, enhanced seed protein and enhanced seed oil. Plasmid vectors were prepared by cloning DNA identified in Table 1 and inserting the cloned DNA into a base transformation vector.

In *Agrobacterium*-mediated transformation corn embryo cells from a corn line that is readily transformable (e.g. corn line designated LH59) are grown in a greenhouse to produce ears that are harvested when the embryos are 1.5 to 2.0 mm in length. The ears are surface sterilized by spraying or soaking in 80% ethanol, followed by air drying. Immature embryos are isolated from individual kernels on surface sterilized ears. Prior to inoculation of maize cells, *Agrobacterium* cells are grown overnight at room temperature. Immature maize embryo cells are inoculated with *Agrobacterium* shortly after excision, and incubated at room temperature with *Agrobacterium* for 5-20 minutes. Immature embryo plant cells are then co-cultured with *Agrobacterium* for 1 to 3 days at 23° C. in the dark. Co-cultured embryos are transferred to selection media and cultured for approximately two weeks to allow embryogenic callus to develop. Embryogenic callus is transferred to culture medium containing 100 mg/L paromomycin and subcultured at about two week intervals. Transformed plant cells are recovered 6 to 8 weeks after initiation of selection.

For transformation by microprojectile bombardment maize immature embryos are isolated and cultured 3-4 days prior to bombardment. Prior to microprojectile bombardment, a suspension of gold particles is prepared onto which the desired recombinant DNA expression cassettes are precipitated. DNA is introduced into maize cells as described in U.S. Pat. Nos. 5,550,318 and 6,399,861 using the electric discharge particle acceleration gene delivery device. Following microprojectile bombardment, tissue is cultured in the dark at 27° C. Additional transformation methods and materials for making transgenic plants of this invention, for example, various media and recipient target cells, transformation of immature embryos and subsequence regeneration of fertile transgenic plants are disclosed in U.S. Pat. Nos. 6,194,636 and 6,232,526 and U.S. patent application Ser. No. 09/757,089, which are incorporated herein by reference.

To regenerate transgenic corn plants a callus of transgenic plant cells resulting from transformation and selection is placed on media to initiate shoot development into plantlets which are transferred to potting soil for initial growth in a growth chamber at 26° C. followed by a mist bench before transplanting to 5 inch pots where plants are grown to maturity. The regenerated plants are self-fertilized and seed is harvested for use in one or more methods to select seeds, seedlings or progeny second generation transgenic plants (R2 plants) or hybrids, e.g. by selecting transgenic plants exhibiting an enhanced trait as compared to a control plant.

Transgenic corn plant cells are transformed with recombinant DNA from each of the genes identified in Table 1, e.g. with DNA having the nucleotide sequence of SEQ ID NO:1-614. Progeny transgenic plants and seed of the transformed plant cells are screened for enhanced water-use efficiency, enhanced cold tolerance, increased yield, enhanced nitrogen use efficiency, enhanced seed protein and enhanced seed oil as reported in Example 7.

Example 3

Soybean Transformation

This example illustrates transformation methods useful in introducing recombinant DNA into soybean chromosomes to produce the transgenic nuclei, plant cells, plants and pollen and the production and identification of transgenic soybean plants and seed with an enhanced trait, i.e. enhanced water use efficiency, enhanced cold tolerance, increased yield, enhanced nitrogen use efficiency, enhanced seed protein and enhanced seed oil. Plasmid vectors were prepared by cloning DNA identified in Table 1 and inserting the cloned DNA into a base transformation vector.

For *Agrobacterium*-mediated transformation, soybean seeds are imbibed overnight and the meristem explants excised. The explants are placed in a wounding vessel. Soybean explants and induced *Agrobacterium* cells from a strain containing plasmid DNA with the gene of interest cassette and a plant selectable marker cassette are mixed no later than 14 hours from the time of initiation of seed imbibition, and wounded using sonication. Following wounding, explants are placed in co-culture for 2-5 days at which point they are transferred to selection media for 6-8 weeks to allow selection and growth of transgenic shoots. Resistant shoots are harvested approximately 6-8 weeks and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil. Additionally, a DNA construct can be transferred into the genome of a soybean cell by particle bombardment and the cell regenerated into a fertile soybean plant as described in U.S. Pat. No. 5,015,580, herein incorporated by reference.

Transgenic soybean plant cells are transformed with recombinant DNA from each of the genes identified in Table 2, i.e. with DNA having the nucleotide sequence of SEQ ID NO: 1-614. Transgenic progeny plants and seed of the transformed plant cells are screened for enhanced water use efficiency, enhanced cold tolerance, increased yield, enhanced nitrogen use efficiency, enhanced seed protein and enhanced seed oil as reported in Example 7.

Example 4

Cotton Transgenic Plants with Enhanced Agronomic Traits

This example illustrates transformation methods useful in introducing recombinant DNA into cotton chromosomes to produce the transgenic nuclei, plant cells, plants and pollen and the production and identification of transgenic cotton plants and seed with an enhanced trait, i.e. enhanced water use efficiency, enhanced cold tolerance, increased yield, enhanced nitrogen use efficiency, enhanced seed protein and enhanced seed oil. Plasmid vectors were prepared by cloning DNA identified in Table 1 and inserting the cloned DNA into a base transformation vector.

Cotton transformation is performed as generally described in WO0036911 and in U.S. Pat. No. 5,846,797. Transgenic cotton plants containing each of the recombinant DNA having a sequence of SEQ ID NO: 1 through SEQ ID NO: 614 are obtained by transforming with recombinant DNA from each of the genes identified in Table 2. Progeny transgenic plants are selected from a population of transgenic cotton events under specified growing conditions and are compared with control cotton plants. Control cotton plants are substantially the same cotton genotype but without the recombinant DNA, for example, either a parental cotton plant of the same genotype that was not transformed with the identical recombinant DNA or a negative isoline of the transformed plant. Additionally, a commercial cotton cultivar adapted to the geographical region and cultivation conditions, i.e. cotton variety ST474, cotton variety FM 958, and cotton variety Siokra L-23, are used to compare the relative performance of the transgenic cotton plants containing the recombinant DNA. The specified culture conditions are growing a first set of transgenic and control plants under "wet" conditions, i.e. irrigated in the range of 85 to 100 percent of evapotranspiration to provide leaf water potential of −14 to −18 bars, and growing a second set of transgenic and control plants under "dry" conditions, i.e. irrigated in the range of 40 to 60 percent of evapotranspiration to provide a leaf water potential of −21 to −25 bars. Pest control, such as weed and insect control is applied equally to both wet and dry treatments as needed. Data gathered during the trial includes weather records throughout the growing season including detailed records of rainfall; soil characterization information; any herbicide or insecticide applications; any gross agronomic differences observed such as leaf morphology, branching habit, leaf color, time to flowering, and fruiting pattern; plant height at various points during the trial; stand density; node and fruit number including node above white flower and node above crack boll measurements; and visual wilt scoring. Cotton boll samples are taken and analyzed for lint fraction and fiber quality. The cotton is harvested at the normal harvest timeframe for the trial area. Enhanced water use efficiency is indicated by increased yield, improved relative water content, enhanced leaf water potential, increased biomass, enhanced leaf extension rates, and improved fiber parameters.

The transgenic cotton plants of this invention are identified from among the transgenic cotton plants by agronomic trait screening as having increased yield and enhanced water use efficiency.

Example 5

Oilseed Rape Transformation

This example illustrates transformation methods useful in introducing recombinant DNA into oilseed-rape (canola) chromosomes to produce the transgenic nuclei, plant cells, plants and pollen and the production and identification of transgenic canola plants and seed with an enhanced trait, i.e. enhanced water use efficiency, enhanced cold tolerance, increased yield, enhanced nitrogen use efficiency, enhanced seed protein and enhanced seed oil.

Tissues from in vitro grown canola seedlings are prepared and inoculated with overnight-grown *Agrobacterium* cells containing plasmid DNA with the gene of interest cassette and a plant selectable marker cassette. Following co-cultivation with *Agrobacterium*, the infected tissues are allowed to grow on selection to promote growth of transgenic shoots, followed by growth of roots from the transgenic shoots. The selected plantlets are then transferred to the greenhouse and potted in soil. Molecular characterization are performed to confirm the presence of the gene of interest, and its expression in transgenic plants and progenies. Progeny transgenic plants are selected from a population of transgenic canola events under specified growing conditions and are compared with control canola plants. Control canola plants are substantially the same canola genotype but without the recombinant DNA, for example, either a parental canola plant of the same genotype that is not transformed with the identical recombinant DNA or a negative isoline of the transformed plant Transgenic canola plant cells are transformed with recombinant DNA from each of the genes identified in Table 2. Transgenic progeny plants and seed of the transformed plant cells are screened for enhanced water use efficiency, enhanced cold tolerance, increased yield, enhanced nitrogen use efficiency, enhanced seed protein and enhanced seed oil as reported in Example 7.

Example 6

Homolog Identification

This example illustrates the identification of homologs of proteins encoded by the DNA identified in Table 2 which is used to provide transgenic seed and plants having enhanced agronomic traits. From the sequence of the homologs, homologous DNA sequence can be identified for preparing additional transgenic seeds and plants of this invention with enhanced agronomic traits.

An "All Protein Database" was constructed of known protein sequences using a proprietary sequence database and the National Center for Biotechnology Information (NCBI) non-redundant amino acid database (nr.aa). For each organism from which a polynucleotide sequence provided herein was obtained, an "Organism Protein Database".was constructed of known protein sequences of the organism; it is a subset of the All Protein Database based on the NCBI taxonomy ID for the organism.

The All Protein Database was queried using amino acid sequences provided herein as SEQ ID NO: 615 through SEQ ID NO: 1228 using NCBI "blastp" program with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes of the polynucleotides provided herein, and is referred to as the Core List. Another list was kept for all the hits from each organism, sorted by E-value, and referred to as the Hit List.

The Organism Protein Database was queried using polypeptide sequences provided herein as SEQ ID NO: 615 through SEQ ID NO: 1228 using NCBI "blastp" program with E-value cutoff of 1e-4. Up to 1000 top hits were kept. A BLAST searchable database was constructed based on these hits, and is referred to as "SubDB". SubDB was queried with each sequence in the Hit List using NCBI "blastp" program with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Homologs from a large number of distinct organisms were identified and are reported by amino acid sequences of SEQ ID NO: 1229 through SEQ ID NO: 27373. These relationships of proteins of SEQ ID NO: 615 through 1228 and homologs of SEQ ID NO: 1229 through 27373 are identified in Table 7. The source organism for each homolog is found in the Sequence Listing.

Example 7

Selection of Transgenic Plants with Enhanced Agronomic Trait(s)

This example illustrates identification of plant cells of the invention by screening derived plants and seeds for enhanced trait. Transgenic corn, soybean, cotton and canola seeds and plants with recombinant DNA from each of the genes identified in Table 2 are prepared using plant cells transformed with DNA that is stably integrated into a chromosome of the nuclei in a plant cell. Progeny transgenic plants and seed of the transformed plant cells are screened for enhanced water use efficiency, enhanced cold tolerance, increased yield, enhanced nitrogen use efficiency, enhanced seed protein and enhanced seed oil as compared to control plants.

A. Selection for Enhanced Nitrogen Use Efficiency

The physiological efficacy of transgenic plants, e.g. transgenic corn plants (tested as hybrids), can be tested for nitrogen use efficiency (NUE) traits in a high-throughput nitrogen (N) selection method compared to the measurements from testing of control plants.

Plants are allowed to grow for 28 days in a low nitrogen nutrient environment or for 23 days in a high nitrogen nutrient environment. The nitrogen nutrients are dispensed in the form of a macronutrient solution (see composition below) containing different amounts of nitrogen nutrient (2 mM $NH_4NO_3$ for a low nitrogen environment or 20 mM $NH_4NO_3$ for a high nitrogen environment). Pots with corn plants a provided with 100 ml of nutrient solution three times a week on alternate days starting at eight days after planting for low nitrogen and ten days after planting for high nitrogen. Matting under the pots should be changed as needed to avoid nitrogen accumulation and buildup of root matter. Table 8 shows the amount of nutrients in the low and high nitrogen solutions.

TABLE 8

| Nutrient Stock | 2 mM $NH_4NO_3$ solution (mL/L) | 20 mM $NH_4NO_3$ solution (mL/L) |
|---|---|---|
| 1M $NH_4NO_3$ | 2 | 20 |
| 1M $KH_2PO_4$ | 0.5 | 0.5 |
| 1M $MgSO_4 \cdot 7H_2O$ | 2 | 2 |
| 1M $CaCl_2$ | 2.5 | 2.5 |
| 1M $K_2SO_4$ | 1 | 1 | pH adjusted to 5.6 with HCl or KOH

After 28 days of plant growth under low nitrogen and 23 days of plant growth under high nitrogen, the following variables are measured: total shoot fresh mass (SFM) in grams (g), V6 leaf chlorophyll (LC) measured by Minolta SPAD meter in "relative units", V6 leaf area (LA) measured in square centimeters ($cm^2$), V6 leaf fresh mass (LFM) measured in grams and V6 leaf dry mass (LDM) measured in grams. Leaf fresh mass is measure on leaves that have been dried in a forced air oven at 80° C. for 3 days. From the collected data, two derived measurements are made: (1) Leaf chlorophyll area (LCA), which is a product of V6 relative chlorophyll content and its leaf area (relative units), indicates the spread of chlorophyll over the entire leaf area; and (2) specific leaf area (LSA), which is the ratio of V6 leaf area to its dry mass ($cm^2$/g dry mass), serves as an indicator of nitrogen use efficiency (NUE).

A list of recombinant DNA constructs which improved growth in high nitrogen environments in transgenic plants is reported in Table 9.

TABLE 9

| NUC SEQ ID | PHE ID | Construct | Positive events/Total events screened | Confirmed events/Actual events with confirmation attempted |
|---|---|---|---|---|
| 3 | PHE0000004 | PMON67819 | 2/2 | 2/2 |
| 4 | PHE0000005 | PMON67820 | 2/2 | 2/2 |
| 9 | PHE0000080 | PMON68366 | 1/1 | 0/0 |
| 22 | PHE0000372 | PMON72460 | 2/4 | 1/1 |
| 43 | PHE0000459 | PMON68390 | 2/2 | 0/0 |
| 44 | PHE0000460 | PMON73751 | 3/3 | 2/2 |
| 66 | PHE0000492 | PMON69490 | 3/3 | 2/3 |
| 67 | PHE0000493 | PMON68403 | 2/5 | 0/0 |
| 72 | PHE0000498 | PMON76305 | 5/5 | 0/5 |
| 74 | PHE0000500 | PMON69495 | 1/4 | 0/0 |
| 124 | PHE0000551 | PMON74450 | 1/2 | 0/0 |

TABLE 9-continued

| NUC SEQ ID | PHE ID | Construct | Positive events/Total events screened | Confirmed events/Actual events with confirmation attempted |
|---|---|---|---|---|
| 137 | PHE0000564 | PMON68619 | 6/7 | 0/2 |
| 165 | PHE0000592 | PMON68639 | 4/4 | 2/4 |
| 166 | PHE0000593 | PMON68634 | 5/5 | 1/5 |
| 220 | PHE0000655 | PMON68607 | 5/7 | 1/5 |
| 227 | PHE0000664 | PMON69471 | 4/4 | 3/4 |
| 229 | PHE0000666 | PMON68398 | 6/9 | 2/9 |
| 285 | PHE0000799 | PMON75317 | 1/4 | 0/0 |
| 293 | PHE0000807 | PMON76309 | 1/3 | 0/0 |
| 295 | PHE0000809 | PMON76311 | 3/8 | 0/0 |
| 296 | PHE0000810 | PMON75319 | 1/2 | 0/0 |
| 339 | PHE0000854 | PMON73795 | 1/1 | 0/0 |
| 340 | PHE0000855 | PMON75347 | 1/2 | 0/0 |
| 347 | PHE0000862 | PMON75335 | 2/2 | 0/0 |
| 348 | PHE0000863 | PMON75349 | 1/2 | 0/0 |
| 354 | PHE0000869 | PMON75339 | 1/2 | 0/0 |
| 476 | PHE0000995 | PMON77871 | 1/3 | 0/0 |
| 487 | PHE0001006 | PMON73814 | 1/1 | 0/0 |
| 508 | PHE0001028 | PMON73823 | 1/1 | 0/0 |
| 560 | PHE0001401 | PMON84122 | 7/9 | 0/0 |
| 587 | PHE0001546 | PMON79717 | 2/5 | 0/0 |
| 589 | PHE0001548 | PMON75547 | 2/6 | 0/0 |

A list of recombinant DNA constructs which improved growth in a low (limiting) nitrogen environment in transgenic plants is reported in Table 10.

TABLE 10

| NUC SEQ ID | PHE ID | Construct | Positive events/Total events screened | Confirmed events/Actual events with confirmation attempted |
|---|---|---|---|---|
| 1 | PHE0000002 | PMON80861 | 3/4 | 2/4 |
| 3 | PHE0000004 | PMON67819 | 2/3 | 0/3 |
| 4 | PHE0000005 | PMON67820 | 3/7 | 0/4 |
| 9 | PHE0000080 | PMON68366 | 2/3 | 0/2 |
| 13 | PHE0000113 | PMON68365 | 1/3 | 0/0 |
| 14 | PHE0000140 | PMON73157 | 1/1 | 0/0 |
| 22 | PHE0000372 | PMON72460 | 3/8 | 1/5 |
| 25 | PHE0000375 | PMON73153 | 1/2 | 0/1 |
| 28 | PHE0000378 | PMON72461 | 1/2 | 0/0 |
| 30 | PHE0000381 | PMON72469 | 1/1 | 0/0 |
| 32 | PHE0000384 | PMON68621 | 2/3 | 1/3 |
| 43 | PHE0000459 | PMON68390 | 3/5 | 0/5 |
| 44 | PHE0000460 | PMON73751 | 4/6 | 2/3 |
| 45 | PHE0000461 | PMON67829 | 2/2 | 2/2 |
| 56 | PHE0000479 | PMON68402 | 4/8 | 0/0 |
| 58 | PHE0000481 | PMON75472 | 5/7 | 2/7 |
| 61 | PHE0000487 | PMON80267 | 2/3 | 0/0 |
| 62 | PHE0000488 | PMON75473 | 3/5 | 0/5 |
| 65 | PHE0000491 | PMON72489 | 1/2 | 0/2 |
| 66 | PHE0000492 | PMON69490 | 3/3 | 0/3 |
| 67 | PHE0000493 | PMON68403 | 3/5 | 1/5 |
| 68 | PHE0000494 | PMON75459 | 1/1 | 0/1 |
| 72 | PHE0000498 | PMON76305 | 4/5 | 2/5 |
| 74 | PHE0000500 | PMON69495 | 3/5 | 1/4 |
| 77 | PHE0000503 | PMON69493 | 1/5 | 0/0 |
| 81 | PHE0000507 | PMON69492 | 4/2 | 0/0 |
| 90 | PHE0000516 | PMON72492 | 1/2 | 0/0 |
| 91 | PHE0000517 | PMON72493 | 1/2 | 0/1 |
| 96 | PHE0000523 | PMON69487 | 1/2 | 0/0 |
| 102 | PHE0000529 | PMON69482 | 1/4 | 1/1 |
| 106 | PHE0000533 | PMON84135 | 1/7 | 0/0 |
| 113 | PHE0000540 | PMON75451 | 1/4 | 0/0 |
| 116 | PHE0000543 | PMON69499 | 1/4 | 0/0 |
| 124 | PHE0000551 | PMON74450 | 2/2 | 0/2 |
| 125 | PHE0000552 | PMON75460 | 1/2 | 1/2 |
| 131 | PHE0000558 | PMON68637 | 1/3 | 0/0 |
| 132 | PHE0000559 | PMON74431 | 2/3 | 0/0 |

TABLE 10-continued

| NUC SEQ ID | PHE ID | Construct | Positive events/Total events screened | Confirmed events/Actual events with confirmation attempted |
|---|---|---|---|---|
| 134 | PHE0000561 | PMON68620 | 4/7 | 1/7 |
| 134 | PHE0000561 | PMON68620 | 4/7 | 1/7 |
| 135 | PHE0000562 | PMON75303 | 3/9 | 0/0 |
| 137 | PHE0000564 | PMON68619 | 3/3 | 1/3 |
| 139 | PHE0000566 | PMON75304 | 5/6 | 0/0 |
| 144 | PHE0000571 | PMON69484 | 3/4 | 0/0 |
| 151 | PHE0000578 | PMON69485 | 2/6 | 0/0 |
| 153 | PHE0000580 | PMON68611 | 1/4 | 0/0 |
| 157 | PHE0000584 | PMON68610 | 1/2 | 1/2 |
| 165 | PHE0000592 | PMON68639 | 2/4 | 2/4 |
| 166 | PHE0000593 | PMON68634 | 5/5 | 5/5 |
| 171 | PHE0000604 | PMON68625 | 2/3 | 0/0 |
| 178 | PHE0000611 | PMON68405 | 2/3 | 0/0 |
| 190 | PHE0000623 | PMON74438 | 2/7 | 0/0 |
| 196 | PHE0000629 | PMON68631 | 3/5 | 0/0 |
| 197 | PHE0000630 | PMON68648 | 2/3 | 0/0 |
| 198 | PHE0000631 | PMON75454 | 1/3 | 0/0 |
| 206 | PHE0000639 | PMON75457 | 3/5 | 2/5 |
| 216 | PHE0000649 | PMON78901 | 1/3 | 0/0 |
| 219 | PHE0000654 | PMON68605 | 1/6 | 1/1 |
| 220 | PHE0000655 | PMON84121 | 11/18 | 2/15 |
| 221 | PHE0000656 | PMON80923 | 6/17 | 2/8 |
| 227 | PHE0000664 | PMON69471 | 4/4 | 3/4 |
| 228 | PHE0000665 | PMON84120 | 5/13 | 0/0 |
| 229 | PHE0000666 | PMON68398 | 7/9 | 4/7 |
| 233 | PHE0000703 | PMON75517 | 1/1 | 0/0 |
| 234 | PHE0000704 | PMON76315 | 1/4 | 0/0 |
| 238 | PHE0000710 | PMON84772 | 1/2 | 0/0 |
| 259 | PHE0000748 | PMON75479 | 5/9 | 4/9 |
| 260 | PHE0000749 | PMON84133 | 1/12 | 0/0 |
| 268 | PHE0000762 | PMON75464 | 1/1 | 1/1 |
| 285 | PHE0000799 | PMON75317 | 4/4 | 2/4 |
| 293 | PHE0000807 | PMON76309 | 3/3 | 3/3 |
| 295 | PHE0000809 | PMON76311 | 7/8 | 2/8 |
| 296 | PHE0000810 | PMON75319 | 2/2 | 0/2 |
| 334 | PHE0000849 | PMON82608 | 1/4 | 1/1 |
| 339 | PHE0000854 | PMON73795 | 1/3 | 1/1 |
| 340 | PHE0000855 | PMON75347 | 2/4 | 2/2 |
| 342 | PHE0000857 | PMON75348 | 2/5 | 2/5 |
| 344 | PHE0000859 | PMON73798 | 1/8 | 0/0 |
| 347 | PHE0000862 | PMON75335 | 2/2 | 1/2 |
| 348 | PHE0000863 | PMON75349 | 2/5 | 0/2 |
| 350 | PHE0000865 | PMON75336 | 1/5 | 0/1 |
| 351 | PHE0000866 | PMON84970 | 2/10 | 0/0 |
| 354 | PHE0000869 | PMON75339 | 1/2 | 0/0 |
| 366 | PHE0000885 | PMON77853 | 3/3 | 0/3 |
| 378 | PHE0000897 | PMON73833 | 4/5 | 3/4 |
| 384 | PHE0000903 | PMON77865 | 1/4 | 0/0 |
| 390 | PHE0000909 | PMON73845 | 1/3 | 1/2 |
| 391 | PHE0000910 | PMON73846 | 1/3 | 0/0 |
| 394 | PHE0000913 | PMON78201 | 2/3 | 2/3 |
| 400 | PHE0000919 | PMON73848 | 1/2 | 0/0 |
| 406 | PHE0000925 | PMON73835 | 1 | 0/0 |
| 421 | PHE0000940 | PMON76317 | 1/1 | 0/1 |
| 425 | PHE0000944 | PMON76319 | 1/3 | 1/2 |
| 428 | PHE0000947 | PMON75493 | 1/1 | 1/1 |
| 434 | PHE0000953 | PMON76322 | 1/2 | 0/0 |
| 436 | PHE0000955 | PMON76324 | 1/1 | 0/0 |
| 445 | PHE0000964 | PMON77867 | 2/3 | 0/0 |
| 465 | PHE0000984 | PMON73809 | 1/2 | 0/0 |
| 470 | PHE0000989 | PMON0515 | 2/7 | 0/7 |
| 471 | PHE0000990 | PMON77858 | 6/9 | 2/9 |
| 476 | PHE0000995 | PMON77871 | 3/8 | 0/3 |
| 487 | PHE0001006 | PMON73814 | 1/2 | 1/2 |
| 488 | PHE0001007 | PMON84742 | 2/4 | 0/0 |
| 499 | PHE0001019 | PMON73817 | 1/3 | 0/0 |
| 508 | PHE0001028 | PMON73823 | 2/5 | 2/2 |
| 523 | PHE0001043 | PMON77881 | 1/2 | 1/2 |
| 524 | PHE0001044 | PMON77876 | 1/3 | 0/0 |
| 525 | PHE0001045 | PMON77872 | 2/7 | 0/7 |
| 528 | PHE0001048 | PMON80862 | 1/2 | 1/2 |
| 540 | PHE0001173 | PMON80469 | 6/11 | 0/1 |
| 548 | PHE0001194 | PMON78918 | 1/5 | 0/0 |
| 550 | PHE0001234 | PMON82646 | 2/6 | 0/0 |

TABLE 10-continued

| NUC SEQ ID | PHE ID | Construct | Positive events/Total events screened | Confirmed events/Actual events with confirmation attempted |
|---|---|---|---|---|
| 554 | PHE0001276 | PMON79652 | 2/2 | 1/2 |
| 560 | PHE0001401 | PMON84122 | 6/6 | 5/6 |
| 561 | PHE0001423 | PMON79672 | 2/7 | 0/0 |
| 575 | PHE0001503 | PMON84706 | 1/8 | 0/4 |
| 577 | PHE0001505 | PMON75536 | 2/2 | 0/2 |
| 578 | PHE0001506 | PMON75537 | 1 | 0/0 |
| 581 | PHE0001509 | PMON75540 | 1/3 | 0/0 |
| 587 | PHE0001546 | PMON79717 | 3/6 | 1/6 |
| 588 | PHE0001547 | PMON79184 | 1/3 | 0/2 |
| 589 | PHE0001548 | PMON75547 | 6/6 | 2/6 |
| 600 | PHE0001583 | PMON84780 | 6/7 | 0/0 |
| 608 | PHE0001609 | PMON84709 | 7/7 | 1/7 |
| 611 | PHE0002019 | PMON84744 | 1/3 | 0/0 |
| 612 | PHE0002020 | PMON84769 | 9/9 | 5/9 |
| 613 | PHE0002021 | PMON80309 | 1/4 | 1/1 |
| 614 | PHE0002022 | PMON84753 | 2/3 | 0/0 |

Nitrogen Use Efficacy Field Assay

Transgenic plants of this invention and control plants are planted in field without any supplemental nitrogen being applied. Nitrogen levels in the fields are analyzed in early April pre-planting, e.g. by collecting 30 sample soil cores from 0-24" and 24 to 48" soil layer and analyzing for nitrate-nitrogen, phosphorus (P), potassium (K), organic matter and pH. P, K and micronutrients are applied based upon soil test recommendations. Recombinant DNA constructs which improved growth without any nitrogen source in transgenic plants is reported in Table 11.

TABLE 11

| NUC SEQ ID | PHE ID | Construct | Positive events/Total events screened | Confirmed events/Actual events with confirmation attempted |
|---|---|---|---|---|
| 166 | PHE0000593 | PMON68634 | 1/3 | 0/3 |
| 302 | PHE0000816 | PMON93867 | 2/3 | 0/0 |
| 560 | PHE0001401 | PMON84122 | 3/9 | 0/0 |
| 561 | PHE0001423 | PMON79672 | 1/5 | 0/0 |
| 608 | PHE0001609 | PMON84709 | 1/3 | 0/0 |
| 612 | PHE0002020 | PMON84769 | 2/9 | 0/0 |
| 614 | PHE0002022 | PMON84753 | 1/3 | 0/0 |

B. Selection for Increased Yield

Many transgenic plants with recombinant DNA of this invention in a chromosome in the nucleus of their cells exhibit improved yield as compared to a control plant. Recombinant DNA constructs which show improved yield or enhancement in a surrogate indicators for yield in transgenic corn plants is reported in Table 12. Useful surrogate indicators for yield include source capacity (biomass), source output (sucrose and photosynthesis), sink components (kernel size, ear size, starch in the seed), development (light response, height, density tolerance), maturity, early flowering trait and physiological responses to high density planting, e.g., at 45,000 plants per acre.

TABLE 12

| NUC SEQ ID | PHE ID | Construct | Positive events/Total events screened | Confirmed events/Actual events with confirmation attempted |
|---|---|---|---|---|
| 3 | PHE0000004 | PMON67819 | 1/7 | 0/3 |
| 4 | PHE0000005 | PMON67820 | 1/11 | 0/6 |
| 4 | PHE0000005 | PMON73601 | 1/2 | 0/1 |
| 8 | PHE0000078 | PMON77877 | 1/4 | 0/3 |
| 9 | PHE0000080 | PMON68366 | 1/3 | 0/2 |
| 22 | PHE0000372 | PMON72460 | 2/7 | 0/3 |
| 26 | PHE0000376 | PMON73154 | 1/3 | 0/1 |
| 43 | PHE0000459 | PMON68390 | 1/5 | 0/4 |
| 61 | PHE0000487 | PMON80267 | 1/4 | 0/4 |
| 66 | PHE0000492 | PMON69490 | 1/3 | 0/3 |
| 69 | PHE0000495 | PMON73763 | 1/3 | 0/1 |
| 91 | PHE0000517 | PMON72493 | 3/4 | 0/2 |
| 106 | PHE0000533 | PMON84135 | 1/6 | 0/0 |
| 108 | PHE0000535 | PMON68615 | 1/5 | 1/2 |
| 109 | PHE0000536 | PMON74447 | 1/7 | 0/1 |
| 138 | PHE0000565 | PMON69483 | 1/3 | 0/2 |
| 166 | PHE0000593 | PMON68634 | 1/5 | 0/3 |
| 178 | PHE0000611 | PMON68405 | 2/3 | 0/3 |
| 181 | PHE0000614 | PMON68632 | 1/8 | 0/3 |
| 190 | PHE0000623 | PMON74438 | 2/7 | 1/5 |
| 196 | PHE0000629 | PMON68631 | 1/5 | 0/1 |
| 219 | PHE0000654 | PMON68605 | 1/6 | 0/4 |
| 220 | PHE0000655 | PMON68607 | 1/12 | 1/8 |
| 221 | PHE0000656 | PMON80923 | 1/11 | 0/0 |
| 227 | PHE0000664 | PMON69471 | 1/4 | 0/3 |
| 237 | PHE0000709 | PMON68643 | 1/6 | 0/1 |
| 240 | PHE0000712 | PMON73753 | 1/7 | 0/3 |
| 242 | PHE0000714 | PMON68642 | 2/6 | 1/4 |
| 246 | PHE0000735 | PMON75481 | 1/3 | 0/2 |
| 254 | PHE0000743 | PMON71005 | 3/4 | 0/0 |
| 254 | PHE0000743 | PMON81215 | 1/9 | 0/6 |
| 259 | PHE0000748 | PMON75479 | 1/9 | 0/6 |
| 262 | PHE0000751 | PMON75321 | 1/4 | 0/3 |
| 296 | PHE0000810 | PMON75319 | 1/1 | 0/1 |
| 314 | PHE0000829 | PMON73800 | 1/1 | 0/1 |
| 352 | PHE0000867 | PMON75337 | 1/2 | 0/2 |
| 355 | PHE0000870 | PMON75340 | 1/1 | 0/1 |
| 425 | PHE0000944 | PMON76319 | 2/3 | 1/2 |
| 465 | PHE0000984 | PMON73809 | 1/2 | 0/2 |
| 467 | PHE0000986 | PMON80929 | 2/4 | 0/2 |
| 527 | PHE0001047 | PMON75318 | 1/6 | 0/1 |
| 548 | PHE0001194 | PMON78918 | 1/5 | 0/2 |
| 550 | PHE0001234 | PMON82646 | 1/6 | 0/0 |
| 574 | PHE0001502 | PMON80908 | 1/2 | 0/1 |
| 589 | PHE0001548 | PMON75547 | 1/6 | 0/4 |

C. Selection for Enhanced Water Use Efficiency (WUE)

Water use efficiency can be evaluated by high-throughput methods in greenhouse screening of potted corn plants. This selection process imposes 3 drought/re-water cycles on plants over a total period of 15 days after an initial stress free growth period of 11 days. Each cycle consists of 5 days, with no water being applied for the first four days and water quenching on the 5th day of the cycle. The primary phenotypes analyzed by the selection method are the changes in plant growth rate as determined by height and biomass during a vegetative drought treatment. The hydration status of the shoot tissues following the drought is also measured. The plant height are measured at three time points. The first is taken just prior to the onset drought when the plant is 11 days old, which is the shoot initial height (SIH). The plant height is also measured halfway throughout the drought/re-water regimen, on day 18 after planting, to give rise to the shoot mid-drought height (SMH). Upon the completion of the final drought cycle on day 26 after planting, the shoot portion of the plant is harvested and measured for a final height, which is the shoot wilt height (SWH) and also measured for shoot wilted biomass (SWM). The shoot is placed in water at 40 degrees Celsius in the dark. Three days later, the shoot is weighted to give rise to the shoot turgid weight (STM). After drying in an oven for four days, the shoots are weighted for shoot dry biomass (SDM). The shoot average height (SAH) is the mean plant height across the 3 height measurements.

To correct for slight differences between plants, a size corrected growth value is derived from SIH and SWH. This is the Relative Growth Rate (RGR). Relative Growth Rate (RGR) is calculated for each shoot using the formula [RGR %=(SWH−SIH)/((SWH+SIH)/2)*100]. Relative water content (RWC) is a measurement of how much (%) of the plant was water at harvest. Water Content (RWC) is calculated for each shoot using the formula [RWC %=(SWM−SDM)/(STM−SDM)*100]. Fully watered corn plants of this age run around 98% RWC. Transgenic plants with recombinant DNA constructs which provide improved water use efficiency in transgenic corn plants are reported in Table 15.

TABLE 15

| NUC SEQ ID | PHE ID | Construct | Positive events/Total events screened | Confirmed events/ Actual events with confirmation attempted |
|---|---|---|---|---|
| 3 | PHE0000004 | PMON67819 | 3/7 | 2/4 |
| 3 | PHE0000004 | PMON82452 | 6/11 | 0/0 |
| 4 | PHE0000004 | PMON67820 | 4/11 | 2/11 |
| 8 | PHE0000078 | PMON77877 | 1/1 | 0/0 |
| 9 | PHE0000080 | PMON68366 | 2/3 | 2/3 |
| 10 | PHE0000081 | PMON67814 | 3/6 | 3/6 |
| 13 | PHE0000113 | PMON68365 | 2/3 | 0/3 |
| 15 | PHE0000151 | PMON67822 | 2/4 | 0/2 |
| 21 | PHE0000367 | PMON72500 | 1/1 | 0/1 |
| 22 | PHE0000372 | PMON72460 | 5/8 | 0/7 |
| 23 | PHE0000373 | PMON73151 | 1/2 | 1/2 |
| 27 | PHE0000377 | PMON73155 | 1/1 | 0/1 |
| 29 | PHE0000379 | PMON72457 | 3/3 | 0/2 |
| 30 | PHE0000381 | PMON72469 | 1/4 | 0/4 |
| 34 | PHE0000406 | PMON67841 | 1/1 | 0/0 |
| 43 | PHE0000459 | PMON68390 | 2/5 | 0/5 |
| 44 | PHE0000460 | PMON73751 | 2/5 | 0/3 |
| 45 | PHE0000461 | PMON67829 | 2/2 | 1/2 |
| 54 | PHE0000477 | PMON68401 | 2/4 | 0/0 |
| 58 | PHE0000481 | PMON75472 | 1/7 | 0/0 |
| 62 | PHE0000488 | PMON75473 | 2/6 | 0/0 |
| 63 | PHE0000489 | PMON74432 | 1/5 | 0/5 |
| 72 | PHE0000498 | PMON76305 | 3/5 | 0/0 |
| 76 | PHE0000502 | PMON75474 | 2/9 | 0/0 |
| 81 | PHE0000507 | PMON69492 | 1/4 | 0/0 |
| 84 | PHE0000510 | PMON72491 | 2/2 | 0/2 |
| 86 | PHE0000512 | PMON74444 | 3/9 | 0/2 |
| 91 | PHE0000517 | PMON72493 | 1/4 | 0/3 |
| 108 | PHE0000535 | PMON68615 | 2/5 | 0/0 |
| 109 | PHE0000536 | PMON74447 | 2/5 | 0/0 |
| 124 | PHE0000551 | PMON74450 | 1/2 | 0/2 |
| 125 | PHE0000552 | PMON75460 | 1/2 | 0/2 |
| 132 | PHE0000559 | PMON74431 | 2/4 | 0/2 |
| 135 | PHE0000562 | PMON75303 | 7/9 | 0/0 |
| 137 | PHE0000564 | PMON68619 | 2/3 | 0/0 |
| 138 | PHE0000565 | PMON69483 | 1/3 | 0/0 |
| 139 | PHE0000566 | PMON75304 | 6/7 | 0/0 |
| 152 | PHE0000579 | PMON68623 | 1/4 | 0/1 |
| 155 | PHE0000582 | PMON75476 | 1/4 | 0/0 |
| 165 | PHE0000592 | PMON68639 | 1/4 | 0/4 |
| 166 | PHE0000593 | PMON68634 | 1/5 | 0/5 |
| 170 | PHE0000603 | PMON68626 | 1/6 | 0/0 |
| 177 | PHE0000610 | PMON75494 | 1/4 | 0/0 |
| 186 | PHE0000619 | PMON74435 | 2/3 | 0/3 |
| 188 | PHE0000621 | PMON75482 | 2/3 | 0/0 |
| 190 | PHE0000623 | PMON74438 | 2/7 | 0/0 |
| 212 | PHE0000645 | PMON68640 | 2/4 | 0/0 |
| 220 | PHE0000655 | PMON68607 | 4/13 | 0/6 |
| 221 | PHE0000656 | PMON80923 | 2/9 | 0/0 |
| 229 | PHE0000666 | PMON68398 | 2/10 | 0/0 |
| 234 | PHE0000704 | PMON76315 | 2/4 | 0/0 |
| 237 | PHE0000709 | PMON68643 | 4/6 | 1/6 |
| 240 | PHE0000712 | PMON73753 | 1/7 | 0/0 |
| 242 | PHE0000714 | PMON68642 | 1/6 | 0/0 |

TABLE 15-continued

| NUC SEQ ID | PHE ID | Construct | Positive events/Total events screened | Confirmed events/ Actual events with confirmation attempted |
|---|---|---|---|---|
| 243 | PHE0000715 | PMON68641 | 1/5 | 0/0 |
| 246 | PHE0000735 | PMON75481 | 1/3 | 0/0 |
| 252 | PHE0000741 | PMON80930 | 2/8 | 0/0 |
| 253 | PHE0000742 | PMON75478 | 2/2 | 0/2 |
| 254 | PHE0000743 | PMON81215 | 2/9 | 0/5 |
| 256 | PHE0000745 | PMON73776 | 2/4 | 0/0 |
| 259 | PHE0000748 | PMON75479 | 2/8 | 0/0 |
| 262 | PHE0000751 | PMON75321 | 1/4 | 0/0 |
| 268 | PHE0000762 | PMON75464 | 1/1 | 0/1 |
| 270 | PHE0000764 | PMON75465 | 3/4 | 0/0 |
| 278 | PHE0000772 | PMON75468 | 1/3 | 0/0 |
| 281 | PHE0000779 | PMON76307 | 1/4 | 0/0 |
| 285 | PHE0000799 | PMON75317 | 3/4 | 0/0 |
| 295 | PHE0000809 | PMON76311 | 1/7 | 0/0 |
| 313 | PHE0000828 | PMON75327 | 1/3 | 0/0 |
| 320 | PHE0000835 | PMON75344 | 2/7 | 0/0 |
| 330 | PHE0000845 | PMON76313 | 1/3 | 0/0 |
| 339 | PHE0000854 | PMON73795 | 1/4 | 0/2 |
| 340 | PHE0000855 | PMON75347 | 2/4 | 0/0 |
| 342 | PHE0000857 | PMON75348 | 2/6 | 0/4 |
| 348 | PHE0000863 | PMON75349 | 2/5 | 0/0 |
| 350 | PHE0000865 | PMON75336 | 1/5 | 0/0 |
| 352 | PHE0000867 | PMON75337 | 1/2 | 0/0 |
| 354 | PHE0000869 | PMON75339 | 1/2 | 0/0 |
| 356 | PHE0000871 | PMON75341 | 2/8 | 0/6 |
| 367 | PHE0000886 | PMON73804 | 1/2 | 1/1 |
| 369 | PHE0000888 | PMON73830 | 1/2 | 0/0 |
| 378 | PHE0000897 | PMON73833 | 2/5 | 0/0 |
| 394 | PHE0000913 | PMON78201 | 1/3 | 0/0 |
| 445 | PHE0000964 | PMON77867 | 2/3 | 0/0 |
| 454 | PHE0000973 | PMON73827 | 2/5 | 0/0 |
| 465 | PHE0000984 | PMON73809 | 1/2 | 0/1 |
| 476 | PHE0000995 | PMON77871 | 1/7 | 0/0 |
| 487 | PHE0001006 | PMON73814 | 1/2 | 0/0 |
| 499 | PHE0001019 | PMON73817 | 1/3 | 0/0 |
| 508 | PHE0001028 | PMON73823 | 2/5 | 0/0 |
| 524 | PHE0001044 | PMON77876 | 2/3 | 0/0 |
| 525 | PHE0001045 | PMON77872 | 1/7 | 0/0 |
| 527 | PHE0001047 | PMON75318 | 4/6 | 4/6 |
| 587 | PHE0001546 | PMON79717 | 1/6 | 0/0 |
| 589 | PHE0001548 | PMON75547 | 3/6 | 0/0 |
| 613 | PHE0002021 | PMON80309 | 1/5 | 0/0 |

D. Selection for Growth Under Cold Stress

Plants can be identified as having enhanced growth under cold stress by a cold germination assay using three sets of seeds. The first set consists of seeds that are F1 hybrids that are tested positive for the transgenic events and the recombinant DNA is expressed in the growing seed. The second set consists of control seeds, e.g. a nontransgenic, wild-type negative control made from the same genotype as the seeds in the first set. The third set consists of two cold tolerant and one cold sensitive commercial check lines of corn. All seeds are treated with a fungicide "Captan" (MAESTRO®80DF Fungicide, Arvesta Corporation, San Francisco, Calif., USA), e.g. 0.43 mL Captan is applied per 45 g of corn seeds by mixing it well and drying the fungicide prior to the assay.

Corn seeds are placed embryo side down in deionized water on blotter paper in a tray that is held at 9.7° C. for 24 days (no light) in a growth chamber. Germination counts are taken on days 10, 11, 12, 13, 14, 17, 19, 21, and 24. Seeds are considered germinated if the emerged radicle size is 1 cm. Tissue samples are collected at random on the last day of the experiment for confirmation of RNA expression. A germination index (GI) is calculated after the day 24 count using the formula:

$$GI = (\Sigma([T+1-n][P_i - P_{i-1}]))/T$$

where "T" is the number of days for the experiment, i.e. 24; "n" is the number of days after start on which a count is made; "P" is the percentage of seed germinated during a count; and "i" represents a particular count. Statistical differences are calculated between positive and wild type control.

Events of transgenic plants that showed a statistical significance at the p level of less than 0.05 relative to wild-type controls for improved seed growth under cold stress are reported in Table 16.

TABLE 16

| NUC SEQ ID | PHE ID | Construct | Positive events/Total events screened | Confirmed events/Actual events with confirmation attempted |
|---|---|---|---|---|
| 3 | PHE0000004 | PMON67819 | 1/5 | 1/1 |
| 4 | PHE0000005 | PMON67820 | 7/11 | 3/9 |
| 9 | PHE0000080 | PMON68366 | 1/3 | 0/2 |
| 10 | PHE0000081 | PMON67814 | 1/6 | 0/4 |
| 13 | PHE0000113 | PMON68365 | 2/5 | 0/4 |
| 22 | PHE0000372 | PMON72460 | 5/8 | 2/7 |
| 25 | PHE0000375 | PMON73153 | 1/2 | 0/1 |
| 27 | PHE0000377 | PMON73155 | 1/1 | 0/1 |
| 28 | PHE0000378 | PMON72461 | 1/2 | 1/1 |
| 29 | PHE0000379 | PMON72457 | 3/4 | 2/3 |
| 30 | PHE0000381 | PMON72469 | 3/4 | 2/3 |
| 43 | PHE0000459 | PMON68390 | 3/5 | 2/5 |
| 56 | PHE0000479 | PMON68402 | 6/9 | 4/8 |
| 58 | PHE0000481 | PMON75472 | 1/7 | 0/1 |
| 62 | PHE0000488 | PMON75473 | 4/6 | 3/4 |
| 65 | PHE0000491 | PMON72489 | 2/2 | 0/2 |
| 68 | PHE0000494 | PMON75459 | 1/6 | 0/0 |
| 76 | PHE0000502 | PMON75474 | 4/9 | 1/4 |
| 77 | PHE0000503 | PMON69493 | 3/5 | 1/5 |
| 81 | PHE0000507 | PMON69492 | 3/4 | 2/3 |
| 84 | PHE0000510 | PMON72491 | 1/2 | 0/2 |
| 86 | PHE0000512 | PMON74444 | 2/7 | 2/5 |
| 91 | PHE0000517 | PMON72493 | 1/3 | 0/3 |
| 97 | PHE0000524 | PMON69491 | 1/1 | 1/1 |
| 98 | PHE0000525 | PMON75497 | 1/2 | 0/0 |
| 102 | PHE0000529 | PMON69482 | 3/3 | 3/3 |
| 108 | PHE0000535 | PMON68615 | 2/5 | 0/2 |
| 109 | PHE0000536 | PMON74447 | 1/5 | 0/1 |
| 116 | PHE0000543 | PMON69499 | 1/5 | 1/4 |
| 120 | PHE0000547 | PMON76304 | 4/4 | 0/4 |
| 124 | PHE0000551 | PMON74450 | 1/2 | 0/1 |
| 125 | PHE0000552 | PMON75460 | 1/2 | 0/0 |
| 131 | PHE0000558 | PMON68637 | 2/3 | 0/3 |
| 134 | PHE0000561 | PMON68620 | 6/7 | 5/7 |
| 138 | PHE0000565 | PMON69483 | 6/10 | 3/10 |
| 139 | PHE0000566 | PMON75304 | 1/7 | 0/0 |
| 146 | PHE0000573 | PMON68624 | 2/3 | 2/2 |
| 151 | PHE0000578 | PMON69485 | 4/4 | 4/4 |
| 152 | PHE0000579 | PMON68623 | 3/4 | 3/3 |
| 153 | PHE0000580 | PMON68611 | 5/5 | 4/5 |
| 156 | PHE0000583 | PMON80926 | 1/4 | 0/4 |
| 157 | PHE0000584 | PMON68610 | 1/3 | 0/3 |
| 166 | PHE0000593 | PMON68634 | 4/5 | 3/4 |
| 170 | PHE0000603 | PMON68626 | 1/6 | 0/0 |
| 171 | PHE0000604 | PMON68625 | 3/3 | 0/0 |
| 176 | PHE0000609 | PMON74443 | 1/3 | 0/0 |
| 178 | PHE0000611 | PMON68405 | 1/4 | 0/0 |
| 188 | PHE0000621 | PMON73769 | 1/4 | 0/0 |
| 193 | PHE0000626 | PMON68406 | 1/2 | 0/2 |
| 196 | PHE0000629 | PMON68631 | 1/5 | 0/0 |
| 197 | PHE0000630 | PMON68648 | 3/5 | 3/3 |
| 202 | PHE0000635 | PMON68407 | 1/1 | 1/1 |
| 206 | PHE0000639 | PMON75457 | 1/4 | 0/2 |
| 219 | PHE0000654 | PMON68605 | 4/6 | 1/4 |
| 220 | PHE0000655 | PMON68607 | 2/12 | 1/10 |
| 221 | PHE0000656 | PMON82689 | 4/8 | 2/7 |
| 221 | PHE0000656 | PMON84137 | 1/6 | 0/6 |
| 222 | PHE0000658 | PMON68606 | 2/2 | 2/2 |
| 225 | PHE0000662 | PMON80944 | 2/5 | 1/5 |
| 229 | PHE0000666 | PMON68398 | 3/10 | 0/5 |
| 237 | PHE0000709 | PMON68643 | 1/6 | 0/0 |

TABLE 16-continued

| NUC SEQ ID | PHE ID | Construct | Positive events/Total events screened | Confirmed events/Actual events with confirmation attempted |
|---|---|---|---|---|
| 242 | PHE0000714 | PMON68642 | 3/6 | 0/0 |
| 243 | PHE0000715 | PMON68641 | 1/4 | 0/1 |
| 252 | PHE0000741 | PMON80930 | 3/7 | 0/7 |
| 256 | PHE0000745 | PMON73776 | 1/2 | 0/1 |
| 258 | PHE0000747 | PMON75480 | 1/2 | 0/0 |
| 259 | PHE0000748 | PMON75479 | 3/9 | 2/4 |
| 264 | PHE0000755 | PMON92853 | 3/7 | 2/7 |
| 265 | PHE0000756 | PMON77884 | 1/1 | 0/0 |
| 268 | PHE0000762 | PMON75464 | 1/1 | 1/1 |
| 270 | PHE0000764 | PMON75465 | 1/4 | 1/2 |
| 272 | PHE0000766 | PMON75466 | 1/1 | 0/0 |
| 277 | PHE0000771 | PMON84798 | 1/3 | 0/0 |
| 295 | PHE0000809 | PMON76311 | 4/8 | 2/6 |
| 299 | PHE0000813 | PMON75530 | 1/1 | 0/0 |
| 307 | PHE0000822 | PMON73799 | 1/2 | 0/0 |
| 320 | PHE0000835 | PMON75344 | 1/7 | 0/0 |
| 338 | PHE0000853 | PMON77893 | 1/2 | 0/0 |
| 340 | PHE0000855 | PMON75347 | 1/4 | 0/0 |
| 348 | PHE0000863 | PMON75349 | 1/5 | 0/0 |
| 350 | PHE0000865 | PMON75336 | 1/1 | 0/0 |
| 351 | PHE0000866 | PMON84970 | 1/7 | 0/0 |
| 354 | PHE0000869 | PMON75339 | 1/2 | 0/0 |
| 356 | PHE0000871 | PMON75341 | 1/1 | 0/0 |
| 358 | PHE0000873 | PMON79671 | 1/2 | 0/0 |
| 363 | PHE0000878 | PMON77852 | 1/1 | 0/0 |
| 366 | PHE0000885 | PMON77853 | 3/3 | 0/3 |
| 373 | PHE0000892 | PMON77864 | 1/1 | 0/0 |
| 387 | PHE0000906 | PMON73842 | 1/1 | 0/0 |
| 390 | PHE0000909 | PMON73845 | 1/3 | 0/0 |
| 425 | PHE0000944 | PMON76319 | 1/3 | 0/0 |
| 454 | PHE0000973 | PMON73827 | 1/5 | 0/0 |
| 455 | PHE0000974 | PMON77855 | 1/1 | 0/0 |
| 457 | PHE0000976 | PMON78912 | 1/2 | 0/0 |
| 459 | PHE0000978 | PMON77856 | 1/2 | 0/0 |
| 460 | PHE0000979 | PMON73849 | 1/1 | 0/0 |
| 461 | PHE0000980 | PMON77869 | 1/3 | 0/0 |
| 475 | PHE0000994 | PMON77870 | 1/1 | 0/0 |
| 485 | PHE0001004 | PMON77860 | 1/1 | 0/0 |
| 488 | PHE0001007 | PMON84742 | 4/5 | 2/4 |
| 518 | PHE0001038 | PMON75839 | 1/2 | 0/0 |
| 527 | PHE0001047 | PMON75318 | 2/13 | 2/12 |
| 540 | PHE0001173 | PMON80469 | 1/14 | 0/1 |
| 548 | PHE0001194 | PMON78918 | 4/5 | 1/5 |
| 561 | PHE0001423 | PMON79672 | 3/5 | 1/5 |
| 575 | PHE0001503 | PMON84706 | 5/7 | 5/7 |
| 577 | PHE0001505 | PMON75536 | 2/3 | 0/0 |
| 578 | PHE0001506 | PMON75537 | 1/1 | 0/0 |
| 587 | PHE0001546 | PMON79717 | 4/6 | 2/6 |
| 590 | PHE0001549 | PMON79185 | 1/1 | 0/0 |
| 598 | PHE0001580 | PMON79190 | 2/2 | 1/2 |
| 599 | PHE0001581 | PMON79191 | 1/4 | 0/1 |
| 600 | PHE0001583 | PMON84780 | 2/7 | 0/7 |
| 613 | PHE0002021 | PMON80309 | 3/5 | 0/4 |

Cold stress tolerance for corn plants of this invention is also determined by a field trial under early spring planting around two weeks prior to the time local farmers plant corn to identify recombinant DNA constructs that confer enhanced cold vigor at germination and early seedling growth under cold stress. The same seeds also are planted under local optimal planting conditions such that the crop has little or no exposure to cold condition (normal treatment). Early planting cold field trials were carried out at five locations, Glyndon Minn., Mason Mich., Monmouth Ill., Dayton Iowa and Mystic Conn. At each location seeds are planted under both early and local optimal planting times with 3 repetitions of 20 kernels in a single row in a plot. Seeds are planted 1.5 to 2 inch deep into soil to avoid muddy conditions. Two temperature monitors are set up at each location to monitor both air and soil temperature daily. Seed emergence is defined as the time when the growing shoot breaks the soil surface. The number of emerged seedling in each plot is counted daily from the day the earliest plot begins to emerge until no significant changes in emergence occur. Seedling vigor is also rated on a scale of 1 to 9 at the V3-V4 stage before the average of corn plant height reaches 10 inches, where 1 represents excellent early growth, 5 represents average growth and 9 represents poor growth. Days to 50% emergence, maximum percent emergence and seedling vigor are calculated. Corn plants having recombinant DNA constructs showing enhanced cold vigor at germination and early seedling growth under the early spring planting field conditions are reported in Table 17.

TABLE 17

| NUC SEQ ID | PHE ID | Construct | Positive events/Total events screened | Confirmed events/Actual events with confirmation attempted |
|---|---|---|---|---|
| 56 | PHE0000479 | PMON68402 | 2/6 | 0/0 |
| 62 | PHE0000488 | PMON75473 | 2/3 | 0/0 |
| 77 | PHE0000503 | PMON69493 | 2/3 | 0/0 |
| 102 | PHE0000529 | PMON69482 | 2/3 | 0/0 |
| 134 | PHE0000561 | PMON68620 | 1/5 | 0/0 |
| 138 | PHE0000565 | PMON69483 | 2/2 | 0/0 |
| 152 | PHE0000579 | PMON68623 | 3/4 | 0/0 |
| 153 | PHE0000580 | PMON68611 | 4/5 | 0/0 |
| 197 | PHE0000630 | PMON68648 | 2/4 | 0/0 |
| 222 | PHE0000658 | PMON68606 | 1/2 | 0/0 |
| 259 | PHE0000748 | PMON75479 | 2/2 | 0/0 |
| 295 | PHE0000809 | PMON76311 | 1/3 | 0/0 |

E. Screens for Transgenic Plant Seeds with Increased Protein and/or Oil Levels

Transgenic plants with recombinant DNA producing seed with increased protein and/or oil content are determined by analyzing harvested seed. For example, near-infrared transmittance spectrometry is used to determine the composition of a bulk seed samples by analyzing for multiple traits in a single scan. Typical analysis parameters are provided in Table 18.

TABLE 18

| | |
|---|---|
| Typical sample(s): | Whole grain corn and soybean seeds |
| Analytical time to run method: | Less than 0.75 min per sample |
| Total elapsed time per run: | 1.5 minute per sample |
| Typical and minimum sample size: | Corn typical: 50 cc; minimum 30 cc<br>Soybean typical: 50 cc; minimum 5 cc |
| Typical analytical range: | Determined in part by the specific calibration.<br>Corn - moisture 5-15%, oil 5-20%, protein 5-30%, starch 50-75%, and density 1.0-1.3%.<br>Soybean - moisture 5-15%, oil 15-25%, and protein 35-50%. |

Transgenic plants with recombinant DNA constructs which improve seed compositions in terms of protein content are reported in Table 19.

TABLE 19

| NUC SEQ ID | PHE ID | Construct | Positive events/Total events screened | Confirmed events/Actual events with confirmation attempted |
|---|---|---|---|---|
| 3 | PHE0000004 | PMON67819 | 1/7 | 0/0 |
| 4 | PHE0000005 | PMON67820 | 1/8 | 0/0 |

TABLE 19-continued

| NUC SEQ ID | PHE ID | Construct | Positive events/Total events screened | Confirmed events/Actual events with confirmation attempted |
|---|---|---|---|---|
| 8 | PHE0000078 | PMON77877 | 1/4 | 0/1 |
| 10 | PHE0000081 | PMON67814 | 2/5 | 0/0 |
| 13 | PHE0000113 | PMON68365 | 3/5 | 3/4 |
| 18 | PHE0000364 | PMON77882 | 1/2 | 0/0 |
| 22 | PHE0000372 | PMON72460 | 1/2 | 2/4 |
| 23 | PHE0000373 | PMON73151 | 1/3 | 0/0 |
| 25 | PHE0000375 | PMON73153 | 1/2 | 0/0 |
| 26 | PHE0000376 | PMON73154 | 2/3 | 0/1 |
| 29 | PHE0000379 | PMON72457 | 2/4 | 0/1 |
| 30 | PHE0000381 | PMON72469 | 2/4 | 0/0 |
| 32 | PHE0000384 | PMON68621 | 3/3 | 0/0 |
| 37 | PHE0000409 | PMON72496 | 1/2 | 0/0 |
| 43 | PHE0000459 | PMON68390 | 1/5 | 0/1 |
| 44 | PHE0000460 | PMON73751 | 1/5 | 0/0 |
| 56 | PHE0000479 | PMON68402 | 2/8 | 1/3 |
| 58 | PHE0000481 | PMON75472 | 1/7 | 1/1 |
| 61 | PHE0000487 | PMON80267 | 1/4 | 0/1 |
| 62 | PHE0000488 | PMON75473 | 1/6 | 0/0 |
| 63 | PHE0000489 | PMON74432 | 3/5 | 2/3 |
| 67 | PHE0000493 | PMON68403 | 1/6 | 0/1 |
| 68 | PHE0000494 | PMON75459 | 4/6 | 0/0 |
| 69 | PHE0000495 | PMON73763 | 1/3 | 0/1 |
| 73 | PHE0000499 | PMON72490 | 3/12 | 0/1 |
| 74 | PHE0000500 | PMON69495 | 1/2 | 1/1 |
| 76 | PHE0000502 | PMON75474 | 1/9 | 0/1 |
| 81 | PHE0000507 | PMON69492 | 1/4 | 0/0 |
| 86 | PHE0000512 | PMON74444 | 2/9 | 0/0 |
| 90 | PHE0000516 | PMON72492 | 1/3 | 0/0 |
| 91 | PHE0000517 | PMON72493 | 1/4 | 0/0 |
| 96 | PHE0000523 | PMON69487 | 1/1 | 0/0 |
| 97 | PHE0000524 | PMON69491 | 1/1 | 1/1 |
| 100 | PHE0000527 | PMON74446 | 1/1 | 0/0 |
| 102 | PHE0000529 | PMON69482 | 2/4 | 0/2 |
| 106 | PHE0000533 | PMON81274 | 1/2 | 0/0 |
| 108 | PHE0000535 | PMON68615 | 2/5 | 0/1 |
| 109 | PHE0000536 | PMON74447 | 1/7 | 0/1 |
| 112 | PHE0000539 | PMON74448 | 1/1 | 1/1 |
| 113 | PHE0000540 | PMON75451 | 2/4 | 0/0 |
| 115 | PHE0000542 | PMON68613 | 2/4 | 0/1 |
| 116 | PHE0000543 | PMON69499 | 2/5 | 0/0 |
| 120 | PHE0000547 | PMON76304 | 3/7 | 0/2 |
| 125 | PHE0000552 | PMON75460 | 1/2 | 0/0 |
| 131 | PHE0000558 | PMON68637 | 1/3 | 0/0 |
| 132 | PHE0000559 | PMON74431 | 2/3 | 1/4 |
| 134 | PHE0000561 | PMON68620 | 2/4 | 0/0 |
| 135 | PHE0000562 | PMON75303 | 1/5 | 0/0 |
| 137 | PHE0000564 | PMON68619 | 1/3 | 0/0 |
| 138 | PHE0000565 | PMON69483 | 1/3 | 0/2 |
| 139 | PHE0000566 | PMON75304 | 4/5 | 0/0 |
| 144 | PHE0000571 | PMON69484 | 2/4 | 0/0 |
| 146 | PHE0000573 | PMON68624 | 3/3 | 2/3 |
| 147 | PHE0000574 | PMON74442 | 1/2 | 0/0 |
| 151 | PHE0000578 | PMON69485 | 2/5 | 0/0 |
| 153 | PHE0000580 | PMON68611 | 3/5 | 0/4 |
| 157 | PHE0000584 | PMON68610 | 2/4 | 1/1 |
| 159 | PHE0000586 | PMON68618 | 1/1 | 1/1 |
| 165 | PHE0000592 | PMON68639 | 2/4 | 0/0 |
| 171 | PHE0000604 | PMON68625 | 1/6 | 0/0 |
| 176 | PHE0000609 | PMON74443 | 1/3 | 0/0 |
| 177 | PHE0000610 | PMON75494 | 2/4 | 1/1 |
| 178 | PHE0000611 | PMON68405 | 1/4 | 0/1 |
| 181 | PHE0000614 | PMON68632 | 3/8 | 0/2 |
| 186 | PHE0000619 | PMON74435 | 1/3 | 0/1 |
| 196 | PHE0000629 | PMON68631 | 1/5 | 0/0 |
| 198 | PHE0000631 | PMON75454 | 1/4 | 0/0 |
| 206 | PHE0000639 | PMON75457 | 3/5 | 0/0 |
| 212 | PHE0000645 | PMON68640 | 1/4 | 0/0 |
| 214 | PHE0000647 | PMON74437 | 1/2 | 0/2 |
| 216 | PHE0000649 | PMON78901 | 1/3 | 0/0 |
| 217 | PHE0000650 | PMON76303 | 1/2 | 1/2 |
| 219 | PHE0000654 | PMON68605 | 2/6 | 0/2 |
| 220 | PHE0000655 | PMON68607 | 7/12 | 0/23 |
| 221 | PHE0000656 | PMON80923 | 3/19 | 0/0 |
| 222 | PHE0000658 | PMON68606 | 1/2 | 0/1 |

TABLE 19-continued

| NUC SEQ ID | PHE ID | Construct | Positive events/Total events screened | Confirmed events/Actual events with confirmation attempted |
|---|---|---|---|---|
| 227 | PHE0000664 | PMON69471 | 1/8 | 1/1 |
| 229 | PHE0000666 | PMON68398 | 1/8 | 0/0 |
| 232 | PHE0000702 | PMON77883 | 3/4 | 1/2 |
| 234 | PHE0000704 | PMON76315 | 1/4 | 1/1 |
| 235 | PHE0000705 | PMON75516 | 1/1 | 0/0 |
| 237 | PHE0000709 | PMON68643 | 1/6 | 0/0 |
| 240 | PHE0000712 | PMON73753 | 3/7 | 2/4 |
| 242 | PHE0000714 | PMON68642 | 1/6 | 0/0 |
| 243 | PHE0000715 | PMON68641 | 2/5 | 1/1 |
| 244 | PHE0000716 | PMON68644 | 1/4 | 0/0 |
| 246 | PHE0000735 | PMON75481 | 1/3 | 0/0 |
| 252 | PHE0000741 | PMON80930 | 1/1 | 0/0 |
| 254 | PHE0000743 | PMON71005 | 1/12 | 0/0 |
| 257 | PHE0000746 | PMON73777 | 1/4 | 0/0 |
| 259 | PHE0000748 | PMON75479 | 4/9 | 0/0 |
| 262 | PHE0000751 | PMON75321 | 1/4 | 0/1 |
| 268 | PHE0000762 | PMON75464 | 1/1 | 0/0 |
| 269 | PHE0000763 | PMON75956 | 1/2 | 0/1 |
| 270 | PHE0000764 | PMON75465 | 2/4 | 0/3 |
| 280 | PHE0000774 | PMON75461 | 1/2 | 0/0 |
| 281 | PHE0000779 | PMON74489 | 1/19 | 0/0 |
| 288 | PHE0000802 | PMON76337 | 1/2 | 0/1 |
| 292 | PHE0000806 | PMON76308 | 2/4 | 1/1 |
| 295 | PHE0000809 | PMON76311 | 2/8 | 0/0 |
| 305 | PHE0000819 | PMON75324 | 1/3 | 0/0 |
| 307 | PHE0000822 | PMON73799 | 1/2 | 0/0 |
| 320 | PHE0000835 | PMON75344 | 2/5 | 0/0 |
| 321 | PHE0000836 | PMON75328 | 2/2 | 0/0 |
| 327 | PHE0000842 | PMON75329 | 1/2 | 0/0 |
| 342 | PHE0000857 | PMON75348 | 5/6 | 0/2 |
| 343 | PHE0000858 | PMON73797 | 1/6 | 0/0 |
| 344 | PHE0000859 | PMON73798 | 5/8 | 5/5 |
| 348 | PHE0000863 | PMON75349 | 2/5 | 0/0 |
| 350 | PHE0000865 | PMON75336 | 2/5 | 1/1 |
| 353 | PHE0000868 | PMON75338 | 1/4 | 0/0 |
| 355 | PHE0000870 | PMON75340 | 1/1 | 0/2 |
| 356 | PHE0000871 | PMON75341 | 1/4 | 0/3 |
| 366 | PHE0000885 | PMON77853 | 3/3 | 2/2 |
| 367 | PHE0000886 | PMON73804 | 1/2 | 0/0 |
| 369 | PHE0000888 | PMON73830 | 2/2 | 0/0 |
| 373 | PHE0000892 | PMON77864 | 1/1 | 0/1 |
| 374 | PHE0000893 | PMON73831 | 2/3 | 1/1 |
| 378 | PHE0000897 | PMON73833 | 1/5 | 0/0 |
| 386 | PHE0000905 | PMON77866 | 2/2 | 0/0 |
| 394 | PHE0000913 | PMON78201 | 2/3 | 1/1 |
| 421 | PHE0000940 | PMON76317 | 1/1 | 0/0 |
| 425 | PHE0000944 | PMON76319 | 1/3 | 0/0 |
| 436 | PHE0000955 | PMON76324 | 1/2 | 0/0 |
| 445 | PHE0000964 | PMON77867 | 1/3 | 0/0 |
| 452 | PHE0000971 | PMON73806 | 1/2 | 0/0 |
| 454 | PHE0000973 | PMON73827 | 1/5 | 0/0 |
| 457 | PHE0000976 | PMON78912 | 1/4 | 0/1 |
| 470 | PHE0000989 | PMON80515 | 1/7 | 0/1 |
| 471 | PHE0000990 | PMON77858 | 2/9 | 0/1 |
| 476 | PHE0000995 | PMON77871 | 1/8 | 0/1 |
| 482 | PHE0001001 | PMON77859 | 1/4 | 0/0 |
| 485 | PHE0001004 | PMON77860 | 1/1 | 0/0 |
| 487 | PHE0001006 | PMON73814 | 1/2 | 0/0 |
| 497 | PHE0001016 | PMON73815 | 1/2 | 0/0 |
| 499 | PHE0001019 | PMON73817 | 2/3 | 0/0 |
| 500 | PHE0001020 | PMON73818 | 1/1 | 0/0 |
| 524 | PHE0001044 | PMON77876 | 1/3 | 0/0 |
| 525 | PHE0001045 | PMON77872 | 5/7 | 1/1 |
| 527 | PHE0001047 | PMON75318 | 1/2 | 0/0 |
| 538 | PHE0001165 | PMON75513 | 1/2 | 0/0 |
| 540 | PHE0001173 | PMON80469 | 4/11 | 0/3 |
| 548 | PHE0001194 | PMON78918 | 3/5 | 1/1 |
| 550 | PHE0001234 | PMON82646 | 1/3 | 0/0 |
| 554 | PHE0001276 | PMON79652 | 1/2 | 0/0 |
| 561 | PHE0001423 | PMON79672 | 2/6 | 2/2 |
| 575 | PHE0001503 | PMON84706 | 2/8 | 0/1 |
| 577 | PHE0001505 | PMON75536 | 1/3 | 0/0 |
| 581 | PHE0001509 | PMON75540 | 1/3 | 2/2 |
| 589 | PHE0001548 | PMON75547 | 1/6 | 0/0 |
| 598 | PHE0001580 | PMON79190 | 1/3 | 0/1 |
| 599 | PHE0001581 | PMON79191 | 1/4 | 0/0 |
| 610 | PHE0002018 | PMON79677 | 1/3 | 0/0 |

Transgenic plants with recombinant DNA constructs which improve seed compositions in terms of oil content are reported in Table 20.

TABLE 20

| NUC SEQ ID | PHE ID | Construct | Positive events/Total events screened | Confirmed events/Actual events with confirmation attempted |
|---|---|---|---|---|
| 3 | PHE0000004 | PMON67819 | 1/3 | 0/0 |
| 4 | PHE0000005 | PMON67820 | 1/6 | 0/0 |
| 9 | PHE0000080 | PMON68366 | 1/2 | 0/0 |
| 13 | PHE0000113 | PMON68365 | 2/3 | 0/4 |
| 22 | PHE0000372 | PMON72460 | 2/4 | 1/4 |
| 29 | PHE0000379 | PMON72457 | 1/3 | 0/0 |
| 74 | PHE0000500 | PMON69495 | 1/1 | 0/0 |
| 120 | PHE0000547 | PMON76304 | 1/2 | 0/0 |
| 122 | PHE0000549 | PMON75974 | 1/1 | 0/0 |
| 132 | PHE0000559 | PMON74431 | 1/1 | 0/0 |
| 138 | PHE0000565 | PMON69483 | 1/2 | 0/0 |
| 155 | PHE0000582 | PMON75476 | 1/2 | 0/0 |
| 190 | PHE0000623 | PMON74438 | 1/2 | 0/0 |
| 220 | PHE0000655 | PMON68607 | 2/12 | 0/4 |
| 234 | PHE0000704 | PMON76315 | 1/1 | 0/0 |
| 240 | PHE0000712 | PMON73753 | 1/2 | 0/0 |
| 254 | PHE0000743 | PMON81215 | 1/2 | 0/0 |
| 296 | PHE0000810 | PMON75319 | 1/1 | 0/0 |
| 344 | PHE0000859 | PMON73798 | 1/6 | 0/0 |
| 366 | PHE0000885 | PMON77853 | 1/2 | 0/0 |
| 394 | PHE0000913 | PMON78201 | 1/1 | 0/0 |
| 457 | PHE0000976 | PMON78912 | 1/2 | 0/0 |
| 471 | PHE0000990 | PMON77858 | 1/3 | 0/0 |
| 540 | PHE0001173 | PMON80469 | 2/7 | 0/0 |
| 587 | PHE0001546 | PMON79717 | 2/3 | 0/0 |
| 589 | PHE0001548 | PMON75547 | 1/2 | 0/0 |

Example 8

Consensus Amino Acid Sequence

This example illustrates the identification of consensus amino acid sequences for the proteins encoded by recombinant DNA in transgenic seeds and plants disclosed herein and homologs.

ClustalW program was selected for multiple sequence alignments of the amino acid sequence of SEQ ID NO: 684, 704, 705, 706, 710, 719, 734, 735, 738, 743, 744, 745, 746, 761, 777, 779, 793, 804, 824, 891, 896, 900, 918, 924, 932, 957, 961, 1001, 1015, 1016, 1026, 1027, 1032, 1033, 1036, 1043, 1044, 1045, 1051, 1054, 1059, 1087, 1119, 1123, 1135, 1136, 1137, 1138, 1139, 1165, and their homologs. Three major factors affecting the sequence alignments dramatically are (1) protein weight matrices; (2) gap open penalty; (3) gap extension penalty. Protein weight matrices available for ClustalW program include Blosum, Pam and Gonnet series. Those parameters with gap open penalty and gap extension penalty were extensively tested. On the basis of the test results, Blosum weight matrix, gap open penalty of 10 and gap extension penalty of were chosen for multiple sequence alignment. FIG. 1 shows the consensus sequence of SEQ ID NO: 684 and its homologs. The symbols for consensus sequence are (1) uppercase letters for 100% identity in all positions of multiple sequence alignment output; (2) lowercase letters for >=70% identity; symbol; (3) "X" indicated <70% identity; (4) dashes "-" meaning that gaps were in ≥70% of the sequences.

The consensus amino acid sequence can be used to identify DNA corresponding to the full scope of this invention that is useful in providing transgenic plants, for example corn and soybean plants with enhanced agronomic traits, for example improved nitrogen use efficiency, improved yield, improved water use efficiency and/or improved growth under cold stress, due to the expression in the plants of DNA encoding a protein with amino acid sequence identical to the consensus amino acid sequence.

Example 9

Pfam Domain Module Annotation

This example illustrates the identification by Pfam analysis of domain and domain module in proteins encoded by recombinant DNA in the transgenic plants and seeds disclosed herein. The amino acid sequence of the expressed proteins that were shown to be associated with an enhanced trait were analyzed for Pfam protein family against the current Pfam collection of multiple sequence alignments and hidden Markov models using the HMMER software in the appended computer listing. The Pfam domain modules and individual protein domain for the proteins of SEQ ID NO: 615 through 1228 are shown in Table 21 and Table 22 respectively. The Hidden Markov model databases for the identified protein families are also in the appended computer listing allowing identification of other homologous proteins and their cognate encoding DNA to enable the full breadth of the invention for a person of ordinary skill in the art. Certain proteins are identified by a single Pfam domain and others by multiple Pfam domains. For instance, the protein with amino acids of SEQ ID NO: 668 is characterized by three Pfam domains, i.e., AdoHcyase, 2-Hacid_dh_C and AdoHcyase_NAD. See also the protein with amino acids of SEQ ID NO: 659 which is characterized by five copies of the Pfam domain "Arm". In Table 22 "score" is the gathering score for the Hidden Markov Model of the domain which exceeds the gathering cutoff reported in Table 23.

TABLE 21

| PEP SEQ ID | Pfam module | Position |
|---|---|---|
| 615 | CBFD_NFYB_HMF | 24-89 |
| 616 | CBFD_NFYB_HMF | 26-91 |
| 617 | CBFD_NFYB_HMF | 34-106 |
| 618 | CBFD_NFYB_HMF | 22-87 |
| 619 | Myb_DNA-binding | 24-69 |
| 620 | Globin | 7-147 |
| 621 | HEAT::HEAT::HEAT::FAT::Rapamycin_bind::PI3_PI4_kinase::FATC | 204-240::303-338::748-785::1463-1829::1934-2046::2113-2363::2472-2504 |
| 622 | P-II | 4-105 |
| 623 | AP2 | 143-208 |
| 624 | zf-C3HC4 | 196-237 |
| 625 | AUX_IAA | 21-196 |
| 626 | SET | 772-900 |
| 627 | SET | 739-867 |
| 628 | Pkinase | 34-319 |
| 629 | AdoHcyase | 12-484 |
| 630 | GAF::HisKA::HATPase_c | 159-308::344-409::456-587 |
| 631 | RRM_1 | 10-81 |
| 632 | DUF231 | 283-433 |
| 633 | DUF231 | 210-384 |
| 634 | DUF231 | 254-427 |
| 635 | DUF231 | 232-404 |
| 636 | AP2 | 88-152 |
| 637 | AUX_IAA | 4-155 |
| 638 | Myb_DNA-binding | 55-100 |
| 639 | WRKY | 164-224 |
| 640 | AP2 | 77-141 |
| 641 | bZIP_1 | 201-263 |
| 642 | AP2 | 36-100 |
| 643 | Myb_DNA-binding | 24-69 |
| 644 | Ribosomal_L18p | 27-173 |
| 645 | Cyclin_N | 4-144 |
| 646 | PB1 | 54-147 |
| 647 | PB1 | 46-136 |
| 648 | PB1 | 55-146 |
| 649 | PB1 | 58-148 |
| 650 | Pescadillo_N::BRCT | 8-286::352-429 |
| 651 | Pescadillo_N::BRCT | 4-285::355-436 |
| 652 | 2OG-FeII_Oxy | 176-281 |
| 653 | PI-PLC-X::PI-PLC-Y::C2 | 109-253::320-438::459-551 |
| 654 | C1_1::DAGK_cat::DAGK_acc | 139-200::347-476::493-650 |
| 655 | Exo_endo_phos | 109-538 |
| 656 | S6PP | 2-247 |
| 657 | S6PP::S6PP_C | 8-261::262-393 |

TABLE 21-continued

| PEP SEQ ID | Pfam module | Position |
|---|---|---|
| 658 | UDPGP | 29-441 |
| 659 | U-box::Arm::Arm::Arm::Arm | 256-329::383-423::424-464::465-505::506-546::547-587 |
| 660 | U-box | 29-102 |
| 661 | U-box::Arm::Arm::Arm | 270-342::398-441::442-483::526-567 |
| 662 | Prp19::WD40::WD40::WD40 | 64-133::253-291::298-336::384-421 |
| 663 | U-box | 5-78 |
| 664 | PfkB | 21-336 |
| 665 | PfkB | 24-340 |
| 666 | PfkB | 23-339 |
| 667 | PfkB | 23-323 |
| 668 | AdoHcyase | 12-484 |
| 669 | AdoHcyase | 6-448 |
| 670 | AdoHcyase_NAD | 192-353 |
| 671 | BRAP2::zf-C3HC4::zf-UBP | 51-161::168-207::219-290 |
| 672 | Cu-oxidase_3::Cu-oxidase::Cu-oxidase_2 | 28-145::169-374::469-606 |
| 673 | Glycos_transf_1::S6PP | 241-428::466-713 |
| 674 | Flavoprotein | 264-428 |
| 676 | Flavoprotein | 18-138 |
| 677 | Flavoprotein | 18-163 |
| 678 | IPP-2 | 7-148 |
| 679 | IPP-2 | 2-137 |
| 680 | Lactamase_B | 27-240 |
| 681 | Lactamase_B | 45-264 |
| 682 | Lactamase_B | 50-244 |
| 683 | Histone | 25-94 |
| 685 | zf-C3HC4 | 251-291 |
| 686 | Pkinase | 40-327 |
| 687 | Pkinase | 71-351 |
| 688 | Pkinase | 32-319 |
| 689 | Pkinase | 33-324 |
| 690 | Pkinase | 13-304 |
| 691 | Pkinase | 4-287 |
| 692 | Pkinase | 39-325 |
| 693 | Pkinase | 32-319 |
| 694 | WRKY | 199-259 |
| 695 | WRKY | 158-218 |
| 696 | PPDK_N::PEP-utilizers::PEP-utilizers_C | 100-460::511-601::613-971 |
| 697 | DUF580 | 187-539 |
| 698 | AA_permease | 59-525 |
| 699 | adh_short | 11-180 |
| 700 | adh_short | 15-187 |
| 701 | adh_short | 19-188 |
| 702 | adh_short | 18-186 |
| 703 | adh_short | 17-184 |
| 707 | VDE | 163-360 |
| 708 | SATase_N::Hexapep::Hexapep::Hexapep | 73-177::231-248::257-274::275-292 |
| 709 | SATase_N::Hexapep::Hexapep::Hexapep | 80-184::238-255::264-281::282-299 |
| 711 | NAS | 3-285 |
| 712 | NAS | 39-319 |
| 713 | OPT | 43-656 |
| 714 | Pyridoxal_deC | 33-381 |
| 715 | 2OG-FeII_Oxy | 190-321 |
| 716 | Mlo | 4-501 |
| 717 | G-alpha | 22-366 |
| 718 | WD40::WD40::WD40::WD40::WD40::WD40 | 8-47::65-103::107-145::155-195::199-237::288-326 |
| 720 | F-box::Tub | 53-108::119-406 |
| 721 | F-box::Tub | 34-90::101-358 |
| 722 | F-box::Tub | 51-106::117-448 |
| 723 | F-box::Tub | 45-100::111-367 |
| 724 | F-box::Tub | 73-128::139-436 |
| 725 | F-box::Tub | 48-103::114-401 |
| 726 | F-box::Tub | 58-113::124-456 |
| 727 | LRR_2 | 297-321 |
| 728 | F-box::LRR_1 | 15-63::168-190 |
| 729 | WD40::WD40 | 168-205::257-296 |
| 730 | Asp | 127-460 |
| 731 | Asp | 130-466 |
| 732 | AUX_IAA | 2-182 |
| 733 | LEA_4 | 5-48 |
| 736 | LEA_4 | 57-100 |
| 737 | TLC | 65-563 |
| 739 | Mito_carr::Mito_carr::Mito_carr | 22-119::126-222::226-316 |

TABLE 21-continued

| PEP SEQ ID | Pfam module | Position |
|---|---|---|
| 740 | PBP | 28-218 |
| 741 | PBP | 22-191 |
| 742 | Glycos_transf_1::S6PP | 452-635::676-930 |
| 747 | SRF-TF::K-box | 9-59::74-172 |
| 748 | SRF-TF::K-box | 9-59::73-173 |
| 749 | SBP56 | 24-493 |
| 750 | GST_N::GST_C | 4-79::108-203 |
| 751 | Pkinase::efhand::efhand::efhand::efhand | 93-351::398-426::434-462::470-498::504-532 |
| 752 | CK_II_beta | 87-260 |
| 753 | Zein | 1-234 |
| 754 | AP2 | 113-177 |
| 755 | MFMR::bZIP_1 | 1-156::244-308 |
| 756 | HMG_box | 41-110 |
| 757 | RRM_1 | 10-81 |
| 758 | Enolase_N::Enolase_C | 4-140::148-443 |
| 759 | zf-C3HC4 | 118-160 |
| 760 | Ribosomal_L10::Ribosomal_60s | 6-110::227-317 |
| 762 | SRF-TF::K-box | 9-59::75-166 |
| 763 | SRF-TF::K-box | 9-59::75-172 |
| 764 | SBP | 53-131 |
| 765 | adh_short | 18-218 |
| 766 | adh_short | 16-184 |
| 767 | PBP | 18-163 |
| 768 | PBP | 20-165 |
| 769 | PBP | 17-162 |
| 770 | FLO_LFY | 1-379 |
| 771 | zf-B_box::CCT | 14-60::193-231 |
| 772 | TLC | 91-587 |
| 773 | Ribosomal_L18p | 27-173 |
| 774 | Ribosomal_L18p | 27-173 |
| 775 | Ribosomal_L18p | 26-172 |
| 776 | Orn_Arg_deC_N::Orn_DAP_Arg_deC | 158-396::399-512 |
| 778 | UPF0005 | 28-237 |
| 780 | UPF0005 | 37-249 |
| 781 | zf-LSD1::Peptidase_C14 | 7-31::64-347 |
| 782 | Peptidase_C14 | 65-310 |
| 783 | Peptidase_C14 | 73-352 |
| 784 | Peptidase_C14 | 157-450 |
| 785 | Rieske::PaO | 116-225::325-432 |
| 786 | Rieske::PaO | 33-139::244-336 |
| 787 | SRF-TF::K-box | 9-59::69-169 |
| 788 | DAD | 11-133 |
| 789 | DAD | 3-114 |
| 790 | Pirin::Pirin_C | 91-188::244-356 |
| 791 | Aldedh | 18-487 |
| 792 | Aldedh | 18-488 |
| 794 | PEMT | 10-205 |
| 795 | Methyltransf_11::Methyltransf_11 | 69-167::298-394 |
| 796 | BCCT | 17-503 |
| 797 | BCCT | 19-505 |
| 798 | Na_H_Exchanger | 22-444 |
| 799 | Na_H_Exchanger | 24-443 |
| 800 | H_PPase | 6-748 |
| 801 | H_PPase | 9-752 |
| 802 | H_PPase | 6-751 |
| 803 | HD-ZIP_N::Homeobox::HALZ | 1-96::123-177::178-222 |
| 805 | bZIP_1 | 244-308 |
| 806 | zf-B_box::zf-B_box | 1-47::51-96 |
| 807 | AP2 | 62-126 |
| 808 | Response_reg::CCT | 26-142::628-666 |
| 809 | zf-B_box::zf-B_box::CCT | 17-64::65-107::308-346 |
| 810 | BTB::NPH3 | 20-119::181-443 |
| 811 | Myb_DNA-binding::Myb_DNA-binding | 14-61::67-112 |
| 812 | zf-B_box::zf-B_box | 1-47::52-99 |
| 813 | AP2::AP2 | 159-222::251-315 |
| 814 | Myb_DNA-binding | 24-69 |
| 815 | zf-CCCH::zf-CCCH::zf-CCCH::zf-CCCH::zf-CCCH | 39-65::84-110::130-156::287-313::333-359 |
| 816 | Pkinase | 7-262 |
| 817 | GH3 | 15-570 |
| 818 | PMEI | 33-207 |
| 819 | DPBB_1::Pollen_allerg_1 | 117-199::211-292 |
| 820 | DUF1313 | 23-112 |
| 821 | Cu_bind_like | 35-120 |

TABLE 21-continued

| PEP SEQ ID | Pfam module | Position |
|---|---|---|
| 822 | UPF0041 | 1-109 |
| 823 | MatE::MatE | 15-172::233-396 |
| 825 | DUF221 | 303-726 |
| 826 | Rieske::PaO | 219-316::407-501 |
| 827 | zf-LSD1::Peptidase_C14 | 18-42::80-363 |
| 828 | Myb_DNA-binding | 143-193 |
| 829 | Myb_DNA-binding | 138-188 |
| 830 | HLH | 192-242 |
| 831 | Glycos_transf_1::S6PP | 481-664::773-1047 |
| 832 | Glycos_transf_1::S6PP | 460-643::683-937 |
| 833 | U-box | 29-103 |
| 834 | U-box | 29-102 |
| 835 | Globin::FAD_binding_6::NAD_binding_1 | 6-131::154-253::263-373 |
| 836 | P-II | 4-105 |
| 837 | P-II | 78-180 |
| 838 | DUF231 | 310-483 |
| 839 | DXP_reductoisom::DXP_redisom_C | 81-209::223-306 |
| 840 | DXP_reductoisom::DXP_redisom_C | 5-134::148-231 |
| 841 | DXP_reductoisom::DXP_redisom_C | 11-138::152-235 |
| 842 | Transket_pyr::Transketolase_C | 392-559::573-696 |
| 843 | Transket_pyr::Transketolase_C | 318-485::497-620 |
| 844 | Transket_pyr::Transketolase_C | 354-520::532-648 |
| 845 | S-methyl_trans | 14-319 |
| 846 | S-methyl_trans | 24-328 |
| 847 | S-methyl_trans | 16-310 |
| 848 | S-methyl_trans | 17-322 |
| 849 | Histone | 33-107 |
| 850 | Histone | 19-92 |
| 851 | Histone | 29-102 |
| 852 | Histone | 28-101 |
| 853 | DUF231 | 364-540 |
| 854 | Flavodoxin_2 | 5-218 |
| 855 | MIF4G::MIF4G_like::MIF4G_like_2 | 9-228::304-467::483-770 |
| 856 | MIF4G::MIF4G_like::MIF4G_like_2 | 33-261::343-539::580-820 |
| 857 | RRM_1 | 36-107 |
| 858 | RRM_1 | 48-119 |
| 859 | Pyridoxal_deC | 87-361 |
| 860 | Pyridoxal_deC | 80-381 |
| 861 | Pyridoxal_deC | 110-412 |
| 862 | Pkinase::Pkinase_C | 177-477::495-549 |
| 863 | Pkinase::Pkinase_C | 169-469::487-541 |
| 864 | SRF-TF::K-box | 9-59::75-174 |
| 865 | SRF-TF::K-box | 9-59::76-173 |
| 866 | Myb_DNA-binding | 233-284 |
| 867 | Myb_DNA-binding | 244-294 |
| 868 | FBPase | 5-334 |
| 869 | RPE65 | 131-630 |
| 870 | RPE65 | 68-569 |
| 871 | AP2::AP2 | 289-362::391-456 |
| 872 | FBPase_glpX | 2-334 |
| 873 | FBPase_glpX | 2-334 |
| 874 | Glycos_transf_1 | 211-388 |
| 875 | Glycos_transf_1 | 211-388 |
| 876 | bZIP_1 | 87-151 |
| 877 | WRKY | 239-299 |
| 878 | zf-Dof | 53-115 |
| 879 | Myb_DNA-binding::Myb_DNA-binding | 15-62::68-113 |
| 880 | Myb_DNA-binding::Myb_DNA-binding | 15-62::68-113 |
| 881 | AP2 | 140-204 |
| 882 | HLH | 121-168 |
| 883 | AP2 | 12-77 |
| 884 | AP2 | May-69 |
| 885 | bZIP_2 | 213-267 |
| 886 | Myb_DNA-binding | 36-81 |
| 887 | bZIP_1 | 368-432 |
| 888 | G-alpha | 103-447 |
| 889 | PSK | 13-83 |
| 890 | PSK | 20-118 |
| 892 | PSK | 20-101 |
| 893 | Sugar_tr | 33-473 |
| 894 | MFS_1 | 63-548 |
| 895 | MFS_1 | 46-466 |
| 898 | Phytochrome::HisKA::HATPase_c | 48-227::237-302::349-486 |
| 899 | Hpt | 44-129 |

TABLE 21-continued

| PEP SEQ ID | Pfam module | Position |
|---|---|---|
| 901 | Hpt | 44-122 |
| 902 | Hpt | 30-112 |
| 903 | GAF::HisKA::HATPase_c | 158-307::343-408::455-586 |
| 904 | GAF::HisKA::HATPase_c | 159-308::344-409::456-586 |
| 905 | p450 | 45-523 |
| 906 | Sugar_tr | 32-472 |
| 907 | AP2 | 131-196 |
| 908 | AP2 | 17-81 |
| 909 | AP2 | 17-82 |
| 910 | DUF6::DUF6 | 115-233::253-394 |
| 911 | TPT | 183-335 |
| 912 | TPT | 231-379 |
| 913 | DUF6::DUF6 | 24-157::204-333 |
| 914 | DUF6::DUF6 | 19-146::198-326 |
| 915 | DUF6::DUF6 | 21-154::198-328 |
| 916 | DUF6::DUF6 | 26-160::202-333 |
| 917 | DUF6::DUF6 | 28-161::202-331 |
| 919 | TPT | 156-298 |
| 920 | DUF6::DUF6 | 22-155::201-330 |
| 921 | DUF6::DUF6 | 26-159::205-334 |
| 922 | DUF914 | 1-328 |
| 923 | HEAT::HEAT::HEAT::HEAT::HEAT::HEAT::HEAT | 22-57::97-133::181-217::218-253::259-295::341-376::381-416 |
| 925 | DUF6 | 22-154 |
| 926 | TPT | 167-307 |
| 927 | DUF6 | 15-148 |
| 928 | DUF6::DUF6 | 27-160::201-330 |
| 929 | DUF6::DUF6 | 128-252::277-407 |
| 930 | TPT | 156-299 |
| 931 | DUF914 | 2-327 |
| 933 | DUF6::DUF6 | 31-164::215-344 |
| 934 | TPT | 156-300 |
| 935 | DUF6::DUF6 | 16-149::193-322 |
| 936 | TPT | 163-303 |
| 937 | TPT | 200-344 |
| 938 | Pkinase | 504-777 |
| 939 | B_lectin::PAN_2::Pkinase | 81-189::322-387::470-736 |
| 940 | B_lectin::PAN_2::Pkinase | 80-187::326-391::473-742 |
| 941 | B_lectin::PAN_2::Pkinase | 110-225::360-425::507-776 |
| 942 | B_lectin::PAN_2::Pkinase | 67-176::311-373::450-718 |
| 943 | B_lectin::S_locus_glycop::PAN_2::PAN_1::Pkinase | 74-188::202-333::350-415::362-433::499-784 |
| 944 | B_lectin::S_locus_glycop::PAN_2::Pkinase | 75-199::212-340::357-425::506-790 |
| 945 | PAN_1::Pkinase | 336-417::500-770 |
| 946 | 14-3-3 | 6-243 |
| 947 | 14-3-3 | 6-117 |
| 948 | 14-3-3 | 8-120 |
| 949 | 14-3-3 | 3-240 |
| 950 | 14-3-3 | 3-115 |
| 951 | 14-3-3 | 9-246 |
| 952 | 14-3-3 | 9-120 |
| 953 | 14-3-3 | 5-240 |
| 954 | 14-3-3 | 5-116 |
| 955 | 14-3-3 | 7-116 |
| 956 | 14-3-3 | 4-239 |
| 958 | 14-3-3 | 8-245 |
| 959 | 14-3-3 | 8-120 |
| 960 | 14-3-3 | 8-245 |
| 962 | 14-3-3 | 8-249 |
| 963 | 14-3-3 | 8-125 |
| 964 | G-alpha | 431-841 |
| 965 | Pkinase | 40-363 |
| 966 | Pkinase | 117-402 |
| 967 | Pkinase | 34-319 |
| 968 | CK_II_beta | 93-267 |
| 969 | CK_II_beta | 26-233 |
| 970 | CK_II_beta | 89-263 |
| 971 | CK_II_beta | 87-260 |
| 972 | RRM_1 | 10-81 |
| 973 | RRM_1::zf-CCHC | 9-80::128-145 |
| 974 | RRM_1 | 39-110 |
| 975 | RRM_1 | 33-104 |
| 976 | Methyltransf_11 | 63-162 |
| 977 | Methyltransf_11 | 85-184 |
| 978 | Methyltransf_11 | 70-169 |
| 979 | RRM_1 | 10-81 |

TABLE 21-continued

| PEP SEQ ID | Pfam module | Position |
|---|---|---|
| 980 | zf-C3HC4 | 253-293 |
| 981 | zf-C3HC4 | 190-230 |
| 982 | zf-C3HC4 | 234-274 |
| 983 | zf-C3HC4 | 221-261 |
| 984 | zf-C3HC4 | 156-196 |
| 985 | zf-C3HC4 | 218-258 |
| 986 | zf-C3HC4 | 94-135 |
| 987 | zf-C3HC4 | 204-245 |
| 988 | zf-C3HC4 | 126-169 |
| 989 | PA::zf-C3HC4 | 51-149::237-278 |
| 990 | zf-C3HC4 | 87-128 |
| 991 | zf-C3HC4 | 607-647 |
| 992 | zf-C3HC4 | 467-507 |
| 993 | zf-C3HC4 | 155-195 |
| 994 | zf-C3HC4 | 127-167 |
| 995 | zf-C3HC4 | 33-73 |
| 996 | Skp1_POZ::Skp1 | 5-65::91-168 |
| 997 | Skp1 | 90-164 |
| 998 | Skp1_POZ::Skp1 | 8-68::99-176 |
| 999 | LRR_2::LRR_2 | 174-201::301-325 |
| 1000 | F-box::LRR_1 | 15-63::168-190 |
| 1001 | F-box::LRR_2 | 17-64::299-323 |
| 1003 | Response_reg | 42-177 |
| 1004 | zf-CHY::zf-C3HC4 | 35-113::166-208 |
| 1005 | zf-CHY::zf-C3HC4 | 59-142::195-237 |
| 1006 | MtN3_slv::MtN3_slv | 9-98::132-218 |
| 1007 | zf-C3HC4 | 215-256 |
| 1008 | PHD | 198-248 |
| 1009 | F-box | 17-64 |
| 1010 | F-box | 22-69 |
| 1011 | F-box::Kelch_1::Kelch_1::Kelch_1 | 9-56::97-153::155-201::285-339 |
| 1012 | F-box::Kelch_1::Kelch_1 | 76-123::167-213::215-262 |
| 1013 | F-box::Kelch_1::Kelch_1 | 26-73::116-162::164-210 |
| 1014 | zf-C3HC4 | 49-91 |
| 1017 | Prp19::WD40::WD40::WD40 | 64-133::253-291::298-336::384-421 |
| 1018 | zf-C3HC4 | 36-81 |
| 1019 | zf-C3HC4 | 58-103 |
| 1020 | TPR_1::TPR_1::TPR_2::U-box | 14-47::48-81::82-115::195-269 |
| 1021 | zf-C3HC4 | 24-64 |
| 1022 | F-box::Kelch_1::Kelch_2::Kelch_1::Kelch_2::Kelch_2 | 195-243::292-340::345-392::397-445::449-501::516-564 |
| 1023 | F-box::Kelch_1::Kelch_2::Kelch_1::Kelch_2::Kelch_2 | 205-253::300-348::353-400::405-453::458-509::518-566 |
| 1024 | Cellulose_synt | 167-977 |
| 1025 | Cellulose_synt | 254-1069 |
| 1028 | zf-C3HC4 | 22-64 |
| 1029 | F-box::LysM | 32-79::109-152 |
| 1030 | Sina | 121-320 |
| 1031 | F-box | 18-65 |
| 1034 | F-box | 18-66 |
| 1035 | SPX::zf-C3HC4 | 1-167::238-286 |
| 1037 | Cullin | 15-237 |
| 1038 | zf-C3HC4 | 227-270 |
| 1039 | zf-C3HC4 | 361-398 |
| 1040 | Melibiase | 34-362 |
| 1041 | Copine | 80-227 |
| 1042 | F-box | 36-83 |
| 1046 | F-box::LRR_2 | 1-47::150-174 |
| 1047 | F-box | 11-59 |
| 1048 | U-box | 5-78 |
| 1049 | Glycos_transf_1::S6PP | 465-648::701-942 |
| 1050 | Pkinase::Ribonuc_2-5A | 491-759::764-890 |
| 1052 | Pkinase::Ribonuc_2-5A | 77-345::350-476 |
| 1053 | Pkinase::Ribonuc_2-5A | 674-980::985-1115 |
| 1055 | Pkinase::Ribonuc_2-5A | 101-407::412-542 |
| 1056 | dCMP_cyt_deam_1 | 218-319 |
| 1057 | Aldo_ket_red | 7-285 |
| 1058 | Aldo_ket_red | 5-292 |
| 1060 | SOH1 | 18-112 |
| 1061 | dCMP_cyt_deam_1 | 1-107 |
| 1062 | Put_Phosphatase | 4-229 |
| 1063 | NAF1 | 104-273 |
| 1064 | Aldo_ket_red | 10-289 |
| 1065 | Glutaredoxin | 19-85 |

TABLE 21-continued

| PEP SEQ ID | Pfam module | Position |
|---|---|---|
| 1066 | TPT | 156-299 |
| 1067 | DUF850 | 2-230 |
| 1068 | LEA_2 | 17-166 |
| 1069 | ABA_WDS | 43-96 |
| 1070 | ABA_WDS | 51-104 |
| 1071 | LEA_2 | 30-179 |
| 1072 | LEA_2 | 30-179 |
| 1073 | ABA_WDS | 54-107 |
| 1074 | Sigma70_r2::Sigma70_r3::Sigma70_r4 | 260-330::334-414::433-485 |
| 1075 | Sigma70_r2::Sigma70_r3::Sigma70_r4 | 314-384::388-469::482-535 |
| 1076 | Sigma70_r2::Sigma70_r3::Sigma70_r4 | 302-372::376-457::469-522 |
| 1077 | Bromodomain | 61-150 |
| 1078 | Homeobox::HALZ | 70-124::125-169 |
| 1079 | bZIP_1 | 118-179 |
| 1080 | MFMR::bZIP_1 | 1-156::244-308 |
| 1081 | Remorin_C | 402-512 |
| 1082 | Remorin_N::Remorin_C | 23-83::85-194 |
| 1083 | Myb_DNA-binding | 39-90 |
| 1084 | Homeobox::HALZ | 77-131::132-176 |
| 1085 | Homeobox::HALZ | 77-131::132-176 |
| 1086 | HSF_DNA-bind | 11-170 |
| 1088 | HSF_DNA-bind | 13-167 |
| 1089 | HSF_DNA-bind | 15-219 |
| 1090 | AUX_IAA | 18-218 |
| 1091 | AUX_IAA | 19-219 |
| 1092 | SRF-TF::K-box | 9-59::48-144 |
| 1093 | SRF-TF::K-box | 9-59::75-174 |
| 1094 | SRF-TF::K-box | 9-59::73-173 |
| 1095 | SRF-TF::K-box | 9-59::71-170 |
| 1096 | SRF-TF::K-box | 9-59::76-173 |
| 1097 | SRF-TF::K-box | 9-59::71-170 |
| 1098 | SRF-TF::K-box | 9-59::75-174 |
| 1099 | zf-C2H2 | 35-58 |
| 1100 | LIM::LIM | 10-67::105-162 |
| 1101 | Myb_DNA-binding::Linker_histone | 5-57::122-190 |
| 1102 | Myb_DNA-binding::Myb_DNA-binding | 14-61::67-112 |
| 1103 | Myb_DNA-binding::Myb_DNA-binding | 11-57::63-108 |
| 1104 | Myb_DNA-binding::Myb_DNA-binding | 14-61::67-112 |
| 1105 | NAM | 23-158 |
| 1106 | MED7 | 4-169 |
| 1107 | zf-LSD1::zf-LSD1::zf-LSD1 | 27-51::66-90::104-128 |
| 1108 | Hydrolase | 18-209 |
| 1109 | zf-C3HC4 | 349-389 |
| 1110 | zf-C3HC4 | 244-284 |
| 1111 | zf-CHY::zf-C3HC4 | 35-113::166-208 |
| 1112 | Ank::Ank::Ank::Ank::Ank::zf-C3HC4 | 50-82::83-115::117-148::180-212::223-255::321-370 |
| 1113 | zf-B_box::zf-B_box::CCT | 1-47::48-90::356-394 |
| 1114 | GRAS | 154-464 |
| 1115 | TFIIS::TFIIS_M::TFIIS_C | 1-93::189-317::328-366 |
| 1116 | zf-B_box::zf-B_box | 1-47::55-102 |
| 1117 | Copine | 111-259 |
| 1118 | Copine | 111-259 |
| 1120 | zf-CCCH::zf-CCCH::KH_1::zf-CCCH | 35-61::95-121::246-310::324-349 |
| 1121 | AUX_IAA | 7-222 |
| 1122 | zf-B_box::zf-B_box | 1-47::51-96 |
| 1123 | SRF-TF::K-box | 9-59::75-174 |
| 1124 | SRF-TF::K-box | 9-59::75-174 |
| 1125 | SRF-TF::K-box | 9-59::75-174 |
| 1126 | SRF-TF::K-box | 9-59::75-174 |
| 1127 | SRF-TF::K-box | 9-59::75-174 |
| 1128 | SRF-TF::K-box | 9-59::75-174 |
| 1129 | FLO_LFY | 1-395 |
| 1130 | Hydrolase | 114-295 |
| 1131 | Hydrolase | 130-317 |
| 1132 | Hydrolase | 110-298 |
| 1133 | AP2 | 15-80 |
| 1140 | Pkinase::NAF | 20-275::314-374 |
| 1141 | WD40::WD40 | 560-599::646-683 |
| 1142 | Pkinase | 139-401 |
| 1143 | EMP24_GP25L | 76-137 |
| 1144 | RRM_1::zf-CCHC | 4-70::86-103 |
| 1145 | Frigida | 112-414 |
| 1146 | DUF810 | 175-1046 |

TABLE 21-continued

| PEP SEQ ID | Pfam module | Position |
|---|---|---|
| 1147 | Dor1 | 21-369 |
| 1148 | Alpha-amylase::Alpha-amyl_C2 | 26-356::357-415 |
| 1149 | AT_hook::DUF296 | 99-111::126-246 |
| 1150 | IMPDH | 23-491 |
| 1151 | IMPDH | 35-512 |
| 1152 | IMPDH | 7-473 |
| 1153 | IMPDH | 12-486 |
| 1154 | zf-CCCH::zf-CCCH::KH_1::zf-CCCH | 38-64::105-131::174-236::274-299 |
| 1155 | Response_reg::Myb_DNA-binding | 21-134::214-264 |
| 1156 | zf-C3HC4 | 251-291 |
| 1157 | MFS_1 | 129-549 |
| 1158 | Sugar_tr | 34-472 |
| 1159 | AP2 | 15-80 |
| 1160 | AP2 | 7-72 |
| 1161 | Pyridoxal_deC | 35-383 |
| 1162 | AUX_IAA | 7-263 |
| 1163 | Cyclin_N::Cyclin_C | 92-207::209-336 |
| 1164 | Cyclin_N | 183-321 |
| 1166 | zf-Dof | 105-167 |
| 1167 | NAM | 52-179 |
| 1168 | NAM | 18-145 |
| 1169 | p450 | 41-477 |
| 1170 | LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase | 23-63::90-112::114-136::162-184::186-208::234-256::258-280::282-304::306-328::354-376::402-425::448-470::472-494::519-541::543-565::567-589::591-613::615-638::748-771::772-791::824-846::848-870::1002-1275 |
| 1171 | LRRNT_2::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase | 21-60::139-158::185-207::209-231::233-255::259-281::283-306::308-330::332-354::357-379::381-403::429-451::453-475::477-499::501-520::593-615::617-639::641-663::824-1098 |
| 1172 | LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::LRR_1::Pkinase | 199-219::221-244::246-268::270-293::295-317::319-342::345-367::369-391::393-415::417-439::441-463::465-487::489-511::582-604::630-652::653-674::807-1080 |
| 1173 | FAD_binding_4 | 55-200 |
| 1174 | FAD_binding_4 | 55-200 |
| 1175 | Sterol_desat | 35-210 |
| 1176 | Sterol_desat | 35-246 |
| 1177 | Sterol_desat | 37-248 |
| 1178 | Sterol_desat | 43-254 |
| 1179 | Peptidase_S10 | 41-465 |
| 1180 | Peptidase_S10 | 56-474 |
| 1181 | F-box::Kelch_2::Kelch_2::Kelch_1::Kelch_2 | 205-253::300-348::353-400::405-453::524-572 |
| 1182 | F-box::Kelch_1::Kelch_2::Kelch_1::Kelch_2::Kelch_2 | 272-320::367-415::420-467::472-520::525-576::586-634 |
| 1183 | ADH_N::ADH_zinc_N | 36-165::196-342 |
| 1184 | ADH_N::ADH_zinc_N | 27-155::186-332 |
| 1185 | ADH_N::ADH_zinc_N | 27-155::186-328 |
| 1186 | ADH_N::ADH_zinc_N | 36-165::196-338 |
| 1187 | ADH_N::ADH_zinc_N | 36-165::196-338 |
| 1188 | ADH_N::ADH_zinc_N | 35-163::197-343 |
| 1189 | ADH_N::ADH_zinc_N | 34-163::194-336 |
| 1190 | ADH_N::ADH_zinc_N | 34-163::194-336 |
| 1191 | TPT | 156-298 |
| 1192 | TPT | 154-296 |
| 1193 | TPT | 151-293 |
| 1194 | Sugar_tr | 91-552 |
| 1195 | Cyclin_N::Cyclin_C | 61-193::195-326 |
| 1196 | SAC3_GANP | 24-209 |
| 1197 | SAC3_GANP | 20-211 |
| 1198 | SAC3_GANP | 24-209 |
| 1199 | SAC3_GANP | 24-209 |
| 1200 | WD40::WD40 | 183-220::289-328 |
| 1201 | WD40::WD40 | 204-241::311-350 |
| 1202 | CHASE::HisKA::HATPase_c::Response_reg | 86-298::359-424::471-654::829-963 |
| 1203 | CHASE::HisKA::HATPase_c::Response_reg | 198-411::472-537::584-759::945-1068 |

TABLE 21-continued

| PEP SEQ ID | Pfam module | Position |
|---|---|---|
| 1204 | CHASE::HisKA::HATPase_c::Response_reg | 302-526::587-652::699-866::1035-1170 |
| 1205 | CHASE::HisKA::HATPase_c::Response_reg | 163-389::450-515::562-722::890-1025 |
| 1206 | MFS_1 | 66-429 |
| 1207 | MFS_1 | 69-432 |
| 1208 | MFS_1 | 51-415 |
| 1209 | CHASE::HisKA::HATPase_c::Response_reg | 110-321::382-447::494-682::869-1004 |
| 1210 | PTR2 | 113-517 |
| 1211 | PTR2 | 118-521 |
| 1212 | PTR2 | 97-499 |
| 1213 | PTR2 | 122-526 |
| 1214 | PTR2 | 98-500 |
| 1215 | AT_hook::DUF296 | 34-46::61-180 |
| 1220 | BIR::BIR | 20-117::153-241 |
| 1221 | AT_hook::DUF296 | 34-46::61-180 |
| 1224 | Bap31 | 1-188 |

TABLE 22

| PEP SEQ ID | Pfam domain | Start | End | score | E-value |
|---|---|---|---|---|---|
| 615 | CBFD_NFYB_HMF | 24 | 89 | 126.8 | 5.90E-35 |
| 616 | CBFD_NFYB_HMF | 26 | 91 | 130.9 | 3.50E-36 |
| 617 | CBFD_NFYB_HMF | 34 | 106 | 117.8 | 3.10E-32 |
| 618 | CBFD_NFYB_HMF | 22 | 87 | 131 | 3.40E-36 |
| 619 | Myb_DNA-binding | 24 | 69 | 54.5 | 3.50E-13 |
| 620 | Globin | 7 | 147 | 127.6 | 3.50E-35 |
| 621 | HEAT | 204 | 240 | 23.5 | 7.80E-04 |
| 621 | HEAT | 303 | 338 | 11.6 | 1.60E+00 |
| 621 | HEAT | 748 | 785 | 17.7 | 4.20E-02 |
| 621 | FAT | 1463 | 1829 | 498.6 | 7.00E-147 |
| 621 | Rapamycin_bind | 1934 | 2046 | 187.1 | 4.40E-53 |
| 621 | PI3_PI4_kinase | 2113 | 2363 | 365.6 | 7.80E-107 |
| 621 | FATC | 2472 | 2504 | 44.7 | 3.10E-10 |
| 622 | P-II | 4 | 105 | 244 | 3.10E-70 |
| 623 | AP2 | 143 | 208 | 145.4 | 1.50E-40 |
| 624 | zf-C3HC4 | 196 | 237 | 19.6 | 1.50E-03 |
| 625 | AUX_IAA | 21 | 196 | 2.8 | 1.20E-09 |
| 626 | SET | 772 | 900 | 157.6 | 3.20E-44 |
| 627 | SET | 739 | 867 | 157.6 | 3.20E-44 |
| 628 | Pkinase | 34 | 319 | 302.5 | 7.70E-88 |
| 629 | AdoHcyase | 12 | 484 | 826.2 | 1.70E-245 |
| 629 | 2-Hacid_dh_C | 219 | 399 | -77 | 1.30E-03 |
| 629 | AdoHcyase_NAD | 240 | 403 | 393.3 | 3.60E-115 |
| 630 | GAF | 159 | 308 | 98.7 | 1.70E-26 |
| 630 | HisKA | 344 | 409 | 87.6 | 3.80E-23 |
| 630 | HATPase_c | 456 | 587 | 131.8 | 2.00E-36 |
| 631 | RRM_1 | 10 | 81 | 108.2 | 4.20E-29 |
| 632 | DUF231 | 283 | 433 | 139.3 | 1.10E-38 |
| 633 | DUF231 | 210 | 384 | 210.9 | 2.90E-60 |
| 634 | DUF231 | 254 | 427 | 265.7 | 9.50E-77 |
| 635 | DUF231 | 232 | 404 | 99.1 | 1.30E-26 |
| 636 | AP2 | 88 | 152 | 147.9 | 2.70E-41 |
| 637 | AUX_IAA | 4 | 155 | 28.5 | 1.80E-11 |
| 638 | Myb_DNA-binding | 55 | 100 | 58 | 3.20E-14 |
| 639 | WRKY | 164 | 224 | 139.9 | 7.00E-39 |
| 640 | AP2 | 77 | 141 | 142.7 | 1.00E-39 |
| 641 | bZIP_2 | 199 | 253 | 29.9 | 8.90E-06 |
| 641 | bZIP_1 | 201 | 263 | 31.2 | 3.70E-06 |
| 642 | AP2 | 36 | 100 | 148 | 2.50E-41 |
| 643 | Myb_DNA-binding | 24 | 69 | 54.2 | 4.20E-13 |
| 644 | Ribosomal_L18p | 27 | 173 | 263.6 | 3.90E-76 |
| 645 | Cyclin_N | 4 | 144 | 47.9 | 3.50E-11 |
| 646 | PB1 | 54 | 147 | 103 | 9.00E-28 |
| 647 | PB1 | 46 | 136 | 91.6 | 2.50E-24 |
| 648 | PB1 | 55 | 146 | 90.6 | 4.90E-24 |
| 649 | PB1 | 58 | 148 | 92.7 | 1.10E-24 |
| 650 | Pescadillo_N | 8 | 286 | 523.1 | 3.10E-154 |
| 650 | BRCT | 352 | 429 | 47.9 | 3.50E-11 |
| 651 | Pescadillo_N | 4 | 285 | 667.1 | 1.40E-197 |
| 651 | BRCT | 355 | 436 | 48.4 | 2.50E-11 |
| 652 | 2OG-FeII_Oxy | 176 | 281 | 135 | 2.00E-37 |
| 653 | PI-PLC-X | 109 | 253 | 146.2 | 8.90E-41 |
| 653 | PI-PLC-Y | 320 | 438 | 84.2 | 4.10E-22 |
| 653 | C2 | 459 | 551 | 81.4 | 2.90E-21 |
| 654 | C1_1 | 139 | 200 | 38.3 | 2.60E-08 |
| 654 | DAGK_cat | 347 | 476 | 130.6 | 4.50E-36 |
| 654 | DAGK_acc | 493 | 650 | 144.9 | 2.20E-40 |
| 655 | Exo_endo_phos | 109 | 538 | 148 | 2.50E-40 |
| 656 | S6PP | 2 | 247 | 493.5 | 2.60E-145 |
| 656 | Hydrolase_3 | 6 | 242 | -20.7 | 5.50E-06 |
| 657 | S6PP | 8 | 261 | 556.5 | 2.60E-164 |
| 657 | Hydrolase_3 | 12 | 242 | -15.4 | 2.70E-06 |
| 657 | S6PP_C | 262 | 393 | 322.8 | 6.00E-94 |
| 658 | UDPGP | 29 | 441 | 981.2 | 3.70E-292 |
| 659 | U-box | 256 | 329 | 93 | 9.30E-25 |
| 659 | Arm | 383 | 423 | 48.9 | 1.80E-11 |
| 659 | Arm | 424 | 464 | 21.9 | 2.20E-03 |
| 659 | Arm | 465 | 505 | 40.9 | 4.30E-09 |
| 659 | Arm | 506 | 546 | 18.5 | 2.40E-02 |
| 659 | Arm | 547 | 587 | 34.2 | 4.50E-07 |
| 660 | U-box | 29 | 102 | 84.8 | 2.70E-22 |
| 661 | U-box | 270 | 342 | 81.2 | 3.30E-21 |
| 661 | Arm | 398 | 441 | 19.1 | 1.60E-02 |
| 661 | Arm | 442 | 483 | 17.5 | 4.90E-02 |
| 661 | Arm | 526 | 567 | 21.2 | 3.80E-03 |
| 662 | Prp19 | 64 | 133 | 161.6 | 2.10E-45 |
| 662 | WD40 | 253 | 291 | 47.2 | 5.40E-11 |
| 662 | WD40 | 298 | 336 | 33.4 | 8.10E-07 |
| 662 | WD40 | 384 | 421 | 32.2 | 1.80E-06 |
| 663 | U-box | 5 | 78 | 69.7 | 9.30E-18 |
| 664 | PfkB | 21 | 336 | 284.2 | 2.50E-82 |
| 665 | PfkB | 24 | 340 | 279.5 | 6.70E-81 |
| 666 | PfkB | 23 | 339 | 282.4 | 8.70E-82 |
| 667 | PfkB | 23 | 323 | 269 | 9.80E-78 |
| 668 | AdoHcyase | 12 | 484 | 828 | 4.90E-246 |
| 668 | 2-Hacid_dh_C | 219 | 399 | -77 | 1.30E-03 |
| 668 | AdoHcyase_NAD | 240 | 403 | 393.3 | 3.60E-115 |
| 669 | AdoHcyase | 6 | 448 | 744.6 | 6.30E-221 |
| 669 | AdoHcyase_NAD | 194 | 355 | 393.2 | 3.90E-115 |
| 670 | AdoHcyase | 8 | 424 | 133.5 | 5.90E-37 |
| 670 | 2-Hacid_dh_C | 171 | 341 | -56.8 | 4.40E-05 |
| 670 | AdoHcyase_NAD | 192 | 353 | 252.7 | 7.60E-73 |
| 670 | IlvN | 211 | 360 | -67.8 | 1.40E-03 |
| 671 | BRAP2 | 51 | 161 | 136.6 | 7.00E-38 |
| 671 | zf-C3HC4 | 168 | 207 | 40.1 | 7.40E-09 |
| 671 | zf-UBP | 219 | 290 | 119.4 | 1.00E-32 |
| 672 | Cu-oxidase_3 | 28 | 145 | 200.1 | 5.30E-57 |
| 672 | Cu-oxidase | 169 | 374 | 59.4 | 1.20E-14 |
| 672 | Cu-oxidase_2 | 469 | 606 | 39.1 | 1.50E-08 |
| 673 | Glycos_transf_1 | 241 | 428 | 78.2 | 2.60E-20 |
| 673 | S6PP | 466 | 713 | 451.8 | 9.10E-133 |
| 673 | Hydrolase_3 | 470 | 708 | -13.7 | 2.10E-06 |

TABLE 22-continued

| PEP SEQ ID | Pfam domain | Start | End | score | E-value |
|---|---|---|---|---|---|
| 674 | Flavoprotein | 264 | 428 | 204.8 | 2.00E−58 |
| 676 | Flavoprotein | 18 | 138 | 141.2 | 2.90E−39 |
| 677 | Flavoprotein | 18 | 163 | 105.7 | 1.30E−28 |
| 678 | IPP-2 | 7 | 148 | −29.9 | 1.50E−03 |
| 679 | IPP-2 | 2 | 137 | −23.9 | 4.70E−04 |
| 680 | Lactamase_B | 27 | 240 | 61.3 | 3.20E−15 |
| 681 | Lactamase_B | 45 | 264 | 78.5 | 2.10E−20 |
| 682 | Lactamase_B | 50 | 244 | 82.1 | 1.80E−21 |
| 683 | Histone | 25 | 94 | 67.1 | 5.70E−17 |
| 685 | zf-C3HC4 | 251 | 291 | 37.3 | 5.10E−08 |
| 686 | Pkinase | 40 | 327 | 322.6 | 6.90E−94 |
| 687 | Pkinase | 71 | 351 | 313.1 | 4.90E−91 |
| 688 | Pkinase | 32 | 319 | 321.7 | 1.30E−93 |
| 689 | Pkinase | 33 | 324 | 308.5 | 1.20E−89 |
| 690 | Pkinase | 13 | 304 | 296.9 | 3.80E−86 |
| 691 | Pkinase | 4 | 287 | 395.1 | 1.10E−115 |
| 692 | Pkinase | 39 | 325 | 314.1 | 2.40E−91 |
| 693 | Pkinase | 32 | 319 | 342.5 | 7.10E−100 |
| 694 | WRKY | 199 | 259 | 135.3 | 1.70E−37 |
| 695 | WRKY | 158 | 218 | 132.3 | 1.40E−36 |
| 696 | PPDK_N | 100 | 460 | 599 | 4.20E−177 |
| 696 | PEP-utilizers | 511 | 601 | 167.6 | 3.20E−47 |
| 696 | PEP-utilizers_C | 613 | 971 | 732.1 | 3.60E−217 |
| 697 | DUF580 | 187 | 539 | 516.7 | 2.50E−152 |
| 698 | AA_permease | 59 | 525 | −44.7 | 1.50E−04 |
| 699 | adh_short | 11 | 180 | 113.5 | 5.90E−31 |
| 699 | Epimerase | 13 | 244 | −42.3 | 2.10E−03 |
| 700 | adh_short | 15 | 187 | 111.5 | 2.50E−30 |
| 700 | KR | 15 | 204 | −29.4 | 1.20E−05 |
| 700 | NAD_binding_4 | 19 | 236 | −73.6 | 7.20E−04 |
| 701 | adh_short | 19 | 188 | 81.3 | 3.10E−21 |
| 701 | KR | 19 | 205 | −66.7 | 1.70E−03 |
| 702 | adh_short | 18 | 186 | 110.5 | 5.00E−30 |
| 702 | KR | 18 | 201 | −57.3 | 5.00E−04 |
| 703 | adh_short | 17 | 184 | 90.2 | 6.20E−24 |
| 707 | VDE | 163 | 360 | 553.4 | 2.40E−163 |
| 708 | SATase_N | 73 | 177 | 210 | 5.30E−60 |
| 708 | Hexapep | 231 | 248 | 18.5 | 2.40E−02 |
| 708 | Hexapep | 257 | 274 | 14.9 | 3.00E−01 |
| 708 | Hexapep | 275 | 292 | 9.7 | 9.60E+00 |
| 709 | SATase_N | 80 | 184 | 220 | 5.40E−63 |
| 709 | Hexapep | 238 | 255 | 12 | 2.20E+00 |
| 709 | Hexapep | 264 | 281 | 8.3 | 1.40E+01 |
| 709 | Hexapep | 282 | 299 | 2.9 | 6.40E+01 |
| 711 | NAS | 3 | 285 | 688 | 7.20E−204 |
| 712 | NAS | 39 | 319 | 615.6 | 4.30E−182 |
| 713 | OPT | 43 | 656 | 560.7 | 1.40E−165 |
| 714 | Pyridoxal_deC | 33 | 381 | 538.4 | 7.80E−159 |
| 715 | 2OG-FeII_Oxy | 190 | 321 | 91.1 | 3.40E−24 |
| 716 | Mlo | 4 | 501 | 735 | 4.80E−218 |
| 717 | G-alpha | 22 | 366 | 473.3 | 3.00E−139 |
| 718 | WD40 | 8 | 47 | 34.2 | 4.60E−07 |
| 718 | WD40 | 65 | 103 | 39.8 | 9.50E−09 |
| 718 | WD40 | 107 | 145 | 47.8 | 3.50E−11 |
| 718 | WD40 | 155 | 195 | 47.6 | 4.20E−11 |
| 718 | WD40 | 199 | 237 | 42.4 | 1.60E−09 |
| 718 | WD40 | 288 | 326 | 25.1 | 2.50E−04 |
| 720 | F-box | 53 | 108 | 29.4 | 1.30E−05 |
| 720 | Tub | 119 | 406 | 566.3 | 3.00E−167 |
| 721 | F-box | 34 | 90 | 17.8 | 3.80E−02 |
| 721 | Tub | 101 | 358 | 418.7 | 8.10E−123 |
| 722 | F-box | 51 | 106 | 31.6 | 2.70E−06 |
| 722 | Tub | 117 | 448 | 571.9 | 6.10E−169 |
| 723 | F-box | 45 | 100 | 28 | 3.40E−05 |
| 723 | Tub | 111 | 367 | 414.3 | 1.70E−121 |
| 724 | F-box | 73 | 128 | 23.1 | 9.90E−04 |
| 724 | Tub | 139 | 436 | 500.5 | 2.00E−147 |
| 725 | F-box | 48 | 103 | 15.6 | 1.80E−01 |
| 725 | Tub | 114 | 401 | 594.1 | 1.30E−175 |
| 726 | F-box | 58 | 113 | 26.9 | 7.20E−05 |
| 726 | Tub | 124 | 456 | 614.6 | 8.90E−182 |
| 727 | LRR_1 | 297 | 323 | 8 | 9.00E+00 |
| 727 | LRR_2 | 297 | 321 | 10.3 | 6.10E−01 |
| 728 | F-box | 15 | 63 | 21.2 | 3.70E−03 |
| 728 | LRR_1 | 168 | 190 | 12.6 | 1.30E+00 |
| 729 | WD40 | 168 | 205 | 26.6 | 8.80E−05 |
| 729 | WD40 | 257 | 296 | 35.5 | 1.90E−07 |
| 730 | Asp | 127 | 460 | −46.6 | 7.40E−11 |
| 731 | Asp | 130 | 466 | −79.2 | 6.20E−09 |
| 732 | AUX_IAA | 2 | 182 | 25.2 | 3.10E−11 |
| 733 | LEA_4 | 5 | 48 | 26.7 | 8.20E−05 |
| 736 | LEA_4 | 57 | 100 | 22.9 | 1.10E−03 |
| 737 | TLC | 65 | 563 | 994.5 | 3.70E−296 |
| 739 | Mito_carr | 22 | 119 | 127.2 | 4.60E−35 |
| 739 | Mito_carr | 126 | 222 | 112.8 | 1.00E−30 |
| 739 | Mito_carr | 226 | 316 | 102.5 | 1.30E−27 |
| 740 | PBP | 28 | 218 | 293.1 | 5.40E−85 |
| 741 | PBP | 22 | 191 | 121 | 3.40E−33 |
| 742 | Glycos_transf_1 | 452 | 635 | 61.5 | 2.80E−15 |
| 742 | S6PP | 676 | 930 | −86.2 | 1.10E−04 |
| 747 | SRF-TF | 9 | 59 | 114.1 | 4.10E−31 |
| 747 | K-box | 74 | 172 | 79.3 | 1.20E−20 |
| 748 | SRF-TF | 9 | 59 | 111.5 | 2.40E−30 |
| 748 | K-box | 73 | 173 | 58.3 | 2.60E−14 |
| 749 | SBP56 | 24 | 493 | 1290.6 | 0.00E+00 |
| 750 | GST_N | 4 | 79 | 91.5 | 2.60E−24 |
| 750 | GST_C | 108 | 203 | 80.1 | 6.80E−21 |
| 751 | Pkinase | 93 | 351 | 334 | 2.50E−97 |
| 751 | efhand | 398 | 426 | 37.3 | 5.20E−08 |
| 751 | efhand | 434 | 462 | 25.5 | 1.90E−04 |
| 751 | efhand | 470 | 498 | 34.2 | 4.50E−07 |
| 751 | efhand | 504 | 532 | 35.1 | 2.40E−07 |
| 752 | CK_II_beta | 87 | 260 | 445.5 | 7.10E−131 |
| 753 | Zein | 1 | 234 | 121.6 | 2.30E−33 |
| 754 | AP2 | 113 | 177 | 134.8 | 2.40E−37 |
| 755 | MFMR | 1 | 156 | 268.4 | 1.40E−77 |
| 755 | bZIP_2 | 244 | 298 | 37 | 6.30E−08 |
| 755 | bZIP_1 | 244 | 308 | 89.4 | 1.10E−23 |
| 756 | HMG_box | 41 | 110 | 115.2 | 1.80E−31 |
| 757 | RRM_1 | 10 | 81 | 108.2 | 2.40E−29 |
| 758 | Enolase_N | 4 | 140 | 244 | 3.20E−70 |
| 758 | Enolase_C | 148 | 443 | 729.3 | 2.50E−216 |
| 759 | zf-C3HC4 | 118 | 160 | 35.8 | 1.50E−07 |
| 760 | Ribosomal_L10 | 6 | 110 | 168.2 | 2.00E−47 |
| 760 | Ribosomal_60s | 227 | 317 | 70.2 | 6.60E−18 |
| 762 | SRF-TF | 9 | 59 | 78.3 | 2.40E−20 |
| 762 | K-box | 75 | 166 | 8.4 | 8.50E−05 |
| 763 | SRF-TF | 9 | 59 | 99.2 | 1.30E−26 |
| 763 | K-box | 75 | 172 | 92.4 | 1.30E−24 |
| 764 | SBP | 53 | 131 | 190.3 | 4.80E−54 |
| 765 | adh_short | 18 | 218 | 72.6 | 1.30E−18 |
| 766 | adh_short | 16 | 184 | 116.4 | 7.90E−32 |
| 766 | KR | 16 | 201 | −11 | 1.00E−06 |
| 767 | PBP | 18 | 163 | 220.5 | 3.70E−63 |
| 768 | PBP | 20 | 165 | 193.4 | 5.30E−55 |
| 769 | PBP | 17 | 162 | 162.2 | 1.30E−45 |
| 770 | FLO_LFY | 1 | 379 | 1005.9 | 1.40E−299 |
| 771 | zf-B_box | 14 | 60 | 47 | 6.30E−11 |
| 771 | CCT | 193 | 231 | 70.4 | 5.80E−18 |
| 772 | TLC | 91 | 587 | 1002.7 | 1.30E−298 |
| 773 | Ribosomal_L18p | 27 | 173 | 265.2 | 1.30E−76 |
| 774 | Ribosomal_L18p | 27 | 173 | 263.6 | 3.90E−76 |
| 775 | Ribosomal_L18p | 26 | 172 | 246.3 | 6.30E−71 |
| 776 | Orn_Arg_deC_N | 158 | 396 | 211.9 | 1.40E−60 |
| 776 | Orn_DAP_Arg_deC | 399 | 512 | 108.5 | 2.00E−29 |
| 778 | UPF0005 | 28 | 237 | 70.1 | 7.20E−18 |
| 780 | UPF0005 | 37 | 249 | 37.9 | 3.50E−08 |
| 781 | zf-LSD1 | 7 | 31 | 49.4 | 1.20E−11 |
| 781 | Peptidase_C14 | 64 | 347 | 225.1 | 1.50E−64 |
| 782 | Peptidase_C14 | 65 | 310 | 90 | 7.20E−24 |
| 783 | Peptidase_C14 | 73 | 352 | 132.8 | 9.70E−37 |
| 784 | Peptidase_C14 | 157 | 450 | 268.6 | 1.20E−77 |
| 785 | Rieske | 116 | 225 | 88.5 | 2.10E−23 |
| 785 | PaO | 325 | 432 | 171.8 | 1.80E−48 |
| 786 | Rieske | 33 | 139 | 109 | 1.40E−29 |
| 786 | PaO | 244 | 336 | 155.9 | 1.10E−43 |
| 787 | SRF-TF | 9 | 59 | 108.3 | 2.30E−29 |
| 787 | K-box | 69 | 169 | 112.1 | 1.60E−30 |
| 788 | DAD | 11 | 133 | 309.1 | 8.10E−90 |
| 789 | DAD | 3 | 114 | 219.5 | 7.70E−63 |
| 790 | Pirin | 91 | 188 | 131.1 | 3.00E−36 |
| 790 | Pirin_C | 244 | 356 | 113.3 | 6.90E−31 |
| 791 | Aldedh | 18 | 487 | 820.1 | 1.20E−243 |
| 792 | Aldedh | 18 | 488 | 829.6 | 1.70E−246 |

TABLE 22-continued

| PEP SEQ ID | Pfam domain | Start | End | score | E-value |
|---|---|---|---|---|---|
| 794 | PEMT | 10 | 205 | 548.9 | 5.10E−162 |
| 795 | Methyltransf_11 | 69 | 167 | 74 | 4.90E−19 |
| 795 | Methyltransf_12 | 69 | 165 | 51.3 | 3.20E−12 |
| 795 | CMAS | 240 | 501 | −149.9 | 5.50E−05 |
| 795 | Ubie_methyltran | 275 | 445 | −111.2 | 2.70E−04 |
| 795 | Methyltransf_12 | 298 | 392 | 70.4 | 5.90E−18 |
| 795 | Methyltransf_11 | 298 | 394 | 100.9 | 3.80E−27 |
| 796 | BCCT | 17 | 503 | 1106.5 | 0.00E+00 |
| 797 | BCCT | 19 | 505 | 970.6 | 6.00E−289 |
| 798 | Na_H_Exchanger | 22 | 444 | 185.2 | 1.60E−52 |
| 799 | Na_H_Exchanger | 24 | 443 | 183.2 | 6.30E−52 |
| 800 | H_PPase | 6 | 748 | 1649.7 | 0.00E+00 |
| 801 | H_PPase | 9 | 752 | 1606.8 | 0.00E+00 |
| 802 | H_PPase | 6 | 751 | 1479.9 | 0.00E+00 |
| 803 | HD-ZIP_N | 1 | 96 | 151.2 | 2.80E−42 |
| 803 | Homeobox | 123 | 177 | 65.2 | 2.10E−16 |
| 803 | HALZ | 178 | 222 | 86.1 | 1.10E−22 |
| 805 | bZIP_1 | 244 | 308 | 58.5 | 2.30E−14 |
| 805 | bZIP_2 | 244 | 298 | 51.7 | 2.50E−12 |
| 806 | zf-B_box | 1 | 47 | 39 | 1.70E−08 |
| 806 | zf-B_box | 51 | 96 | 47.1 | 5.90E−11 |
| 807 | AP2 | 62 | 126 | 129.6 | 8.70E−36 |
| 808 | Response_reg | 26 | 142 | 96.2 | 9.90E−26 |
| 808 | CCT | 628 | 666 | 73.6 | 6.40E−19 |
| 809 | zf-B_box | 17 | 64 | 42.1 | 1.80E−09 |
| 809 | zf-B_box | 65 | 107 | 48.3 | 2.60E−11 |
| 809 | CCT | 308 | 346 | 78.8 | 1.70E−20 |
| 810 | BTB | 20 | 119 | 11 | 4.10E−04 |
| 810 | NPH3 | 181 | 443 | 372 | 9.20E−109 |
| 811 | Myb_DNA-binding | 14 | 61 | 51.9 | 2.20E−12 |
| 811 | Myb_DNA-binding | 67 | 112 | 50.8 | 4.50E−12 |
| 812 | zf-B_box | 1 | 47 | 36.8 | 7.50E−08 |
| 812 | zf-B_box | 52 | 99 | 46.1 | 1.20E−10 |
| 813 | AP2 | 159 | 222 | 102.9 | 9.80E−28 |
| 813 | AP2 | 251 | 315 | 80.9 | 4.10E−21 |
| 814 | Myb_DNA-binding | 24 | 69 | 57.9 | 3.40E−14 |
| 815 | zf-CCCH | 39 | 65 | 44.1 | 4.70E−10 |
| 815 | zf-CCCH | 84 | 110 | 43.8 | 6.00E−10 |
| 815 | zf-CCCH | 130 | 156 | 44.5 | 3.70E−10 |
| 815 | zf-CCCH | 287 | 313 | 43.6 | 6.60E−10 |
| 815 | zf-CCCH | 333 | 359 | 46.2 | 1.10E−10 |
| 816 | Pkinase | 7 | 262 | 206.1 | 8.10E−59 |
| 817 | GH3 | 15 | 570 | 1262.5 | 0.00E+00 |
| 818 | PMEI | 33 | 207 | 144.5 | 2.90E−40 |
| 819 | DPBB_1 | 117 | 199 | 120.1 | 6.30E−33 |
| 819 | Pollen_allerg_1 | 211 | 292 | 120 | 6.90E−33 |
| 820 | DUF1313 | 23 | 112 | 213.3 | 5.50E−61 |
| 821 | Cu_bind_like | 35 | 120 | 100.2 | 6.10E−27 |
| 822 | UPF0041 | 1 | 109 | 135.3 | 1.70E−37 |
| 823 | MatE | 15 | 172 | 121.1 | 3.10E−33 |
| 823 | MatE | 233 | 396 | 164.2 | 3.40E−46 |
| 825 | DUF221 | 303 | 726 | 617.9 | 9.10E−183 |
| 826 | Rieske | 219 | 316 | 98.7 | 1.80E−26 |
| 826 | PaO | 407 | 501 | 170.6 | 3.80E−48 |
| 827 | zf-LSD1 | 18 | 42 | 53.5 | 7.00E−13 |
| 827 | Peptidase_C14 | 80 | 363 | 234.7 | 2.00E−67 |
| 828 | Myb_DNA-binding | 143 | 193 | 43.7 | 6.10E−10 |
| 829 | Myb_DNA-binding | 138 | 188 | 45.8 | 1.50E−10 |
| 830 | HLH | 192 | 242 | 27.9 | 3.60E−05 |
| 831 | Glycos_transf_1 | 481 | 664 | 67.9 | 3.30E−17 |
| 831 | S6PP | 773 | 1047 | −77.2 | 2.90E−05 |
| 832 | Glycos_transf_1 | 460 | 643 | 58.7 | 2.00E−14 |
| 832 | S6PP | 683 | 937 | −90.5 | 1.90E−04 |
| 833 | U-box | 29 | 103 | 97.9 | 3.10E−26 |
| 834 | U-box | 29 | 102 | 84.8 | 2.70E−22 |
| 835 | Globin | 6 | 131 | 103.1 | 8.10E−28 |
| 835 | FAD_binding_6 | 154 | 253 | 42.5 | 1.40E−09 |
| 835 | NAD_binding_1 | 263 | 373 | 87.5 | 4.20E−23 |
| 836 | P-II | 4 | 105 | 232.8 | 7.50E−67 |
| 837 | P-II | 78 | 180 | 180 | 6.00E−51 |
| 838 | DUF231 | 310 | 483 | 233.6 | 4.40E−67 |
| 839 | DXP_reductoisom | 81 | 209 | 238.7 | 1.20E−68 |
| 839 | DXP_redisom_C | 223 | 306 | 210.4 | 4.10E−60 |
| 840 | DXP_reductoisom | 5 | 134 | 247.6 | 2.60E−71 |
| 840 | DXP_redisom_C | 148 | 231 | 216.8 | 5.00E−62 |
| 841 | DXP_reductoisom | 11 | 138 | 212.2 | 1.20E−60 |
| 841 | DXP_redisom_C | 152 | 235 | 206.2 | 7.60E−59 |
| 842 | Transket_pyr | 392 | 559 | 233.7 | 4.00E−67 |
| 842 | Transketolase_C | 573 | 696 | 154.1 | 3.60E−43 |
| 843 | Transket_pyr | 318 | 485 | 187.1 | 4.20E−53 |
| 843 | Transketolase_C | 497 | 620 | 135.5 | 1.40E−37 |
| 844 | Transket_pyr | 354 | 520 | 185 | 1.90E−52 |
| 844 | Transketolase_C | 532 | 648 | 111.7 | 2.10E−30 |
| 845 | S-methyl_trans | 14 | 319 | 324.6 | 1.70E−94 |
| 846 | S-methyl_trans | 24 | 328 | 373.5 | 3.40E−109 |
| 847 | S-methyl_trans | 16 | 310 | 485.1 | 8.60E−143 |
| 848 | S-methyl_trans | 17 | 322 | 485.3 | 7.50E−143 |
| 849 | Histone | 33 | 107 | 93.5 | 6.40E−25 |
| 850 | Histone | 19 | 92 | 111.6 | 2.30E−30 |
| 850 | CBFD_NFYB_HMF | 25 | 89 | 20.5 | 2.00E−03 |
| 851 | Histone | 29 | 102 | 100.4 | 5.30E−27 |
| 852 | Histone | 28 | 101 | 98.7 | 1.80E−26 |
| 853 | DUF231 | 364 | 540 | 212.6 | 8.70E−61 |
| 854 | Flavodoxin_2 | 5 | 218 | 190.1 | 5.50E−54 |
| 855 | MIF4G | 9 | 228 | 74.8 | 2.80E−19 |
| 855 | MIF4G_like | 304 | 467 | 158 | 2.50E−44 |
| 855 | MIF4G_like_2 | 483 | 770 | 349.5 | 5.70E−102 |
| 856 | MIF4G | 33 | 261 | 120.5 | 4.80E−33 |
| 856 | MIF4G_like | 343 | 539 | 246.8 | 4.50E−71 |
| 856 | MIF4G_like_2 | 580 | 820 | 322.9 | 5.80E−94 |
| 857 | RRM_1 | 36 | 107 | 59.5 | 1.10E−14 |
| 858 | RRM_1 | 48 | 119 | 59.7 | 9.90E−15 |
| 859 | Pyridoxal_deC | 87 | 361 | 26.2 | 5.40E−16 |
| 860 | Pyridoxal_deC | 80 | 381 | 66.1 | 1.30E−18 |
| 861 | Pyridoxal_deC | 110 | 412 | 58.5 | 4.20E−18 |
| 862 | Pkinase | 177 | 477 | 204.5 | 2.50E−58 |
| 862 | Pkinase_C | 495 | 549 | 33.7 | 6.20E−07 |
| 863 | Pkinase | 169 | 469 | 206.1 | 8.00E−59 |
| 863 | Pkinase_C | 487 | 541 | 32.8 | 1.20E−06 |
| 864 | SRF-TF | 9 | 59 | 119.2 | 1.20E−32 |
| 864 | K-box | 75 | 174 | 158.4 | 1.80E−44 |
| 865 | SRF-TF | 9 | 59 | 120.7 | 4.20E−33 |
| 865 | K-box | 76 | 173 | 128.5 | 1.80E−35 |
| 866 | Myb_DNA-binding | 233 | 284 | 47.9 | 3.30E−11 |
| 867 | Myb_DNA-binding | 244 | 294 | 41.1 | 3.70E−09 |
| 868 | FBPase | 5 | 334 | 567 | 1.90E−167 |
| 869 | RPE65 | 131 | 630 | 696.9 | 1.50E−206 |
| 870 | RPE65 | 68 | 569 | 598.4 | 6.70E−177 |
| 871 | AP2 | 289 | 362 | 138.7 | 1.60E−38 |
| 871 | AP2 | 391 | 456 | 126 | 1.00E−34 |
| 872 | FBPase_glpX | 2 | 334 | 754.2 | 8.00E−224 |
| 873 | FBPase_glpX | 2 | 334 | 730.6 | 1.00E−216 |
| 874 | Glycos_transf_1 | 211 | 388 | 177.1 | 4.50E−50 |
| 875 | Glyco_transf_20 | 7 | 407 | −235.8 | 3.80E−03 |
| 875 | Glycos_transf_1 | 211 | 388 | 175.7 | 1.20E−49 |
| 876 | bZIP_1 | 87 | 151 | 55.7 | 1.60E−13 |
| 876 | bZIP_2 | 87 | 141 | 44.4 | 3.80E−10 |
| 877 | WRKY | 239 | 299 | 143.1 | 7.20E−40 |
| 878 | zf-Dof | 53 | 115 | 135.9 | 1.10E−37 |
| 879 | Myb_DNA-binding | 15 | 62 | 49 | 1.60E−11 |
| 879 | Myb_DNA-binding | 68 | 113 | 49.7 | 9.60E−12 |
| 880 | Myb_DNA-binding | 15 | 62 | 51.3 | 3.20E−12 |
| 880 | Myb_DNA-binding | 68 | 113 | 57.7 | 3.90E−14 |
| 881 | AP2 | 140 | 204 | 153.6 | 5.00E−43 |
| 882 | HLH | 121 | 168 | 24.3 | 3.70E−04 |
| 883 | AP2 | 12 | 77 | 155 | 1.90E−43 |
| 884 | AP2 | 5 | 69 | 119.2 | 1.20E−32 |
| 885 | bZIP_1 | 213 | 276 | 52.3 | 1.60E−12 |
| 885 | bZIP_2 | 213 | 267 | 53.6 | 6.40E−13 |
| 886 | Myb_DNA-binding | 36 | 81 | 56.5 | 8.60E−14 |
| 887 | bZIP_1 | 368 | 432 | 38 | 3.20E−08 |
| 887 | bZIP_2 | 368 | 422 | 33.4 | 8.10E−07 |
| 888 | G-alpha | 103 | 447 | 509.4 | 4.00E−150 |
| 889 | PSK | 13 | 83 | 94.2 | 3.90E−25 |
| 890 | PSK | 20 | 118 | 149.2 | 1.10E−41 |
| 892 | PSK | 20 | 101 | 143.5 | 5.60E−40 |
| 893 | Sugar_tr | 33 | 473 | −38.5 | 1.10E−05 |
| 894 | MFS_1 | 63 | 548 | 57.3 | 5.00E−14 |
| 895 | MFS_1 | 46 | 466 | 28.6 | 1.60E−05 |
| 898 | Phytochrome | 48 | 227 | 27.2 | 3.20E−06 |
| 898 | HisKA | 237 | 302 | 59.6 | 1.00E−14 |
| 898 | HATPase_c | 349 | 486 | 79.2 | 1.30E−20 |
| 899 | Hpt | 44 | 129 | 42.6 | 1.40E−09 |
| 901 | Hpt | 44 | 122 | 55.1 | 2.30E−13 |

TABLE 22-continued

| PEP SEQ ID | Pfam domain | Start | End | score | E-value |
|---|---|---|---|---|---|
| 902 | Hpt | 30 | 112 | 55 | 2.60E-13 |
| 903 | GAF | 158 | 307 | 88.1 | 2.70E-23 |
| 903 | HisKA | 343 | 408 | 87.5 | 4.10E-23 |
| 903 | HATPase_c | 455 | 586 | 134.1 | 3.90E-37 |
| 904 | GAF | 159 | 308 | 75.9 | 1.20E-19 |
| 904 | HisKA | 344 | 409 | 77.9 | 3.20E-20 |
| 904 | HATPase_c | 456 | 586 | 109 | 1.40E-29 |
| 905 | p450 | 45 | 523 | 187.4 | 3.50E-53 |
| 906 | Sugar_tr | 32 | 472 | -71.7 | 1.30E-04 |
| 907 | AP2 | 131 | 196 | 139.5 | 9.10E-39 |
| 908 | AP2 | 17 | 81 | 121.1 | 3.10E-33 |
| 909 | AP2 | 17 | 82 | 142.5 | 1.10E-39 |
| 910 | DUF6 | 115 | 233 | 36.3 | 1.10E-07 |
| 910 | DUF6 | 253 | 394 | 33.4 | 7.90E-07 |
| 911 | TPT | 183 | 335 | 126.5 | 7.30E-35 |
| 912 | UAA | 81 | 385 | -117.9 | 1.60E-04 |
| 912 | TPT | 231 | 379 | 169 | 1.20E-47 |
| 913 | DUF6 | 24 | 157 | 53.3 | 8.30E-13 |
| 913 | DUF6 | 204 | 333 | 26.2 | 1.10E-04 |
| 914 | UAA | 9 | 330 | -142.8 | 2.80E-03 |
| 914 | DUF6 | 19 | 146 | 35.2 | 2.30E-07 |
| 914 | TPT | 189 | 326 | -10.4 | 2.30E-03 |
| 914 | DUF6 | 198 | 326 | 57 | 6.40E-14 |
| 915 | DUF6 | 21 | 154 | 55.4 | 1.80E-13 |
| 915 | DUF6 | 198 | 328 | 30.4 | 6.20E-06 |
| 916 | DUF6 | 26 | 160 | 21.9 | 2.30E-03 |
| 916 | TPT | 193 | 333 | -5.8 | 1.20E-03 |
| 916 | DUF6 | 202 | 333 | 26.8 | 7.50E-05 |
| 917 | DUF6 | 28 | 161 | 39.1 | 1.50E-08 |
| 917 | DUF6 | 202 | 331 | 64.4 | 3.80E-16 |
| 919 | TPT | 156 | 298 | 142.9 | 8.40E-40 |
| 920 | DUF6 | 22 | 155 | 61.9 | 2.00E-15 |
| 920 | DUF6 | 201 | 330 | 45.7 | 1.60E-10 |
| 921 | DUF6 | 26 | 159 | 62.5 | 1.30E-15 |
| 921 | DUF6 | 205 | 334 | 51.9 | 2.20E-12 |
| 922 | DUF914 | 1 | 328 | 373.7 | 2.80E-109 |
| 922 | UAA | 18 | 304 | -142.8 | 2.80E-03 |
| 922 | DUF6 | 22 | 144 | 21.3 | 3.40E-03 |
| 923 | HEAT | 22 | 57 | 12.7 | 1.20E+00 |
| 923 | HEAT | 97 | 133 | 19.8 | 9.90E-03 |
| 923 | HEAT | 181 | 217 | 27.9 | 3.60E-05 |
| 923 | HEAT | 218 | 253 | 13.5 | 8.00E-01 |
| 923 | HEAT | 259 | 295 | 11.7 | 1.60E+00 |
| 923 | HEAT | 341 | 376 | 11.5 | 1.70E+00 |
| 923 | HEAT | 381 | 416 | 18.9 | 1.80E-02 |
| 925 | DUF6 | 22 | 154 | 39.4 | 1.20E-08 |
| 926 | UAA | 27 | 313 | -136.4 | 1.30E-03 |
| 926 | TPT | 167 | 307 | 171.9 | 1.60E-48 |
| 927 | DUF6 | 15 | 148 | 39 | 1.70E-08 |
| 928 | DUF6 | 27 | 160 | 54.3 | 4.10E-13 |
| 928 | DUF6 | 201 | 330 | 29.8 | 9.80E-06 |
| 929 | DUF6 | 128 | 252 | 84.7 | 2.80E-22 |
| 929 | DUF6 | 277 | 407 | 104.4 | 3.40E-28 |
| 930 | TPT | 156 | 299 | 163.8 | 4.30E-46 |
| 931 | DUF914 | 2 | 327 | 672 | 4.60E-199 |
| 933 | DUF6 | 31 | 164 | 53.1 | 9.30E-13 |
| 933 | DUF6 | 215 | 344 | 58.8 | 1.80E-14 |
| 934 | UAA | 6 | 306 | -56.5 | 1.40E-07 |
| 934 | TPT | 156 | 300 | 171.2 | 2.60E-48 |
| 935 | DUF6 | 16 | 149 | 73.5 | 6.70E-19 |
| 935 | DUF6 | 193 | 322 | 76 | 1.20E-19 |
| 936 | TPT | 163 | 303 | 167.7 | 2.90E-47 |
| 937 | UAA | 50 | 350 | -68.7 | 5.60E-07 |
| 937 | TPT | 200 | 344 | 162 | 1.50E-45 |
| 938 | Pkinase | 504 | 777 | 139.8 | 7.20E-39 |
| 938 | Pkinase_Tyr | 504 | 777 | 122.7 | 1.00E-33 |
| 939 | B_lectin | 81 | 189 | 44.9 | 2.70E-10 |
| 939 | PAN_2 | 322 | 387 | 49.4 | 1.20E-11 |
| 939 | PAN_1 | 322 | 404 | 4.4 | 5.80E-02 |
| 939 | Pkinase_Tyr | 470 | 736 | 115.7 | 1.30E-31 |
| 939 | Pkinase | 470 | 736 | 172.3 | 1.20E-48 |
| 940 | B_lectin | 80 | 187 | 49.4 | 1.20E-11 |
| 940 | PAN_2 | 326 | 391 | 74.4 | 3.70E-19 |
| 940 | Pkinase | 473 | 742 | 194.7 | 2.10E-55 |
| 940 | Pkinase_Tyr | 474 | 742 | 106.2 | 9.80E-29 |
| 941 | B_lectin | 110 | 225 | 48.7 | 2.00E-11 |
| 941 | PAN_2 | 360 | 425 | 70.8 | 4.30E-18 |
| 941 | Pkinase | 507 | 776 | 188.2 | 2.00E-53 |
| 941 | Pkinase_Tyr | 508 | 776 | 100.9 | 3.80E-27 |
| 942 | B_lectin | 67 | 176 | 77.3 | 4.90E-20 |
| 942 | PAN_2 | 311 | 373 | 67.5 | 4.30E-17 |
| 942 | Pkinase | 450 | 718 | 195.6 | 1.20E-55 |
| 942 | Pkinase_Tyr | 451 | 718 | 121.9 | 1.80E-33 |
| 943 | B_lectin | 74 | 188 | 122.8 | 9.50E-34 |
| 943 | S_locus_glycop | 202 | 333 | 111.6 | 2.20E-30 |
| 943 | PAN_2 | 350 | 415 | 113.1 | 8.10E-31 |
| 943 | PAN_1 | 362 | 433 | 14.4 | 5.90E-03 |
| 943 | Pkinase | 499 | 784 | 161.9 | 1.70E-45 |
| 943 | Pkinase_Tyr | 500 | 784 | 113.8 | 5.10E-31 |
| 944 | B_lectin | 75 | 199 | 126.2 | 9.10E-35 |
| 944 | S_locus_glycop | 212 | 340 | 129.9 | 7.00E-36 |
| 944 | PAN_2 | 357 | 425 | 108.7 | 1.70E-29 |
| 944 | PAN_1 | 362 | 443 | 13.2 | 7.70E-03 |
| 944 | Pkinase | 506 | 790 | 191.2 | 2.50E-54 |
| 944 | Pkinase_Tyr | 507 | 790 | 106.2 | 9.30E-29 |
| 945 | PAN_1 | 336 | 417 | 3.4 | 7.30E-02 |
| 945 | Pkinase | 500 | 770 | 188 | 2.20E-53 |
| 945 | Pkinase_Tyr | 500 | 770 | 111.2 | 3.00E-30 |
| 946 | 14-3-3 | 6 | 243 | 509.5 | 3.80E-150 |
| 947 | 14-3-3 | 6 | 117 | 28.5 | 1.00E-05 |
| 948 | 14-3-3 | 8 | 120 | 34.7 | 3.20E-07 |
| 949 | 14-3-3 | 3 | 240 | 507.1 | 2.00E-149 |
| 950 | 14-3-3 | 3 | 115 | 27.9 | 1.10E-05 |
| 951 | 14-3-3 | 9 | 246 | 512.4 | 5.10E-151 |
| 952 | 14-3-3 | 9 | 120 | 30.8 | 4.70E-06 |
| 953 | 14-3-3 | 5 | 240 | 492.1 | 6.50E-145 |
| 954 | 14-3-3 | 5 | 116 | 31.7 | 2.50E-06 |
| 955 | 14-3-3 | 7 | 116 | 30.8 | 4.70E-06 |
| 956 | 14-3-3 | 4 | 239 | 430.4 | 2.40E-126 |
| 958 | 14-3-3 | 8 | 245 | 517.1 | 2.00E-152 |
| 959 | 14-3-3 | 8 | 120 | 32 | 2.10E-06 |
| 960 | 14-3-3 | 8 | 245 | 485.1 | 8.30E-143 |
| 962 | 14-3-3 | 8 | 249 | 505.4 | 6.60E-149 |
| 963 | 14-3-3 | 8 | 125 | 31.3 | 3.50E-06 |
| 964 | G-alpha | 431 | 841 | 14.7 | 2.20E-18 |
| 965 | Pkinase | 40 | 363 | 240.5 | 3.60E-69 |
| 966 | Pkinase | 117 | 402 | 287.2 | 3.00E-83 |
| 967 | Pkinase | 34 | 319 | 298.5 | 1.30E-86 |
| 968 | CK_II_beta | 93 | 267 | 451.2 | 1.30E-132 |
| 969 | CK_II_beta | 26 | 233 | 575.7 | 4.40E-170 |
| 970 | CK_II_beta | 89 | 263 | 440.5 | 2.20E-129 |
| 971 | CK_II_beta | 87 | 260 | 445.5 | 7.10E-131 |
| 972 | RRM_1 | 10 | 81 | 104.5 | 3.10E-28 |
| 973 | RRM_1 | 9 | 80 | 108.7 | 1.70E-29 |
| 973 | zf-CCHC | 128 | 145 | 37.8 | 3.90E-08 |
| 974 | RRM_1 | 39 | 110 | 112.7 | 1.00E-30 |
| 975 | RRM_1 | 33 | 104 | 111.1 | 3.10E-30 |
| 976 | Methyltransf_11 | 63 | 162 | 21.8 | 3.90E-04 |
| 976 | Methyltransf_12 | 63 | 161 | 23.9 | 5.80E-06 |
| 977 | Methyltransf_11 | 85 | 184 | 32 | 2.10E-06 |
| 977 | Methyltransf_12 | 85 | 182 | 29.8 | 9.60E-06 |
| 978 | Methyltransf_11 | 70 | 169 | 31.3 | 3.40E-06 |
| 979 | RRM_1 | 10 | 81 | 108.2 | 2.40E-29 |
| 980 | zf-C3HC4 | 253 | 293 | 40.2 | 6.90E-09 |
| 981 | zf-C3HC4 | 190 | 230 | 41.3 | 3.20E-09 |
| 982 | zf-C3HC4 | 234 | 274 | 35.4 | 1.90E-07 |
| 983 | zf-C3HC4 | 221 | 261 | 48.4 | 2.30E-11 |
| 984 | zf-C3HC4 | 156 | 196 | 28.6 | 2.10E-05 |
| 985 | zf-C3HC4 | 218 | 258 | 37.9 | 3.60E-08 |
| 986 | zf-C3HC4 | 94 | 135 | 41.9 | 2.10E-09 |
| 987 | zf-C3HC4 | 204 | 245 | 17.9 | 2.20E-03 |
| 988 | zf-C3HC4 | 126 | 169 | 40.1 | 7.50E-09 |
| 989 | PA | 51 | 149 | 62.7 | 1.20E-15 |
| 989 | zf-C3HC4 | 237 | 278 | 41.3 | 3.30E-09 |
| 990 | zf-C3HC4 | 87 | 128 | 46.1 | 1.20E-10 |
| 991 | zf-C3HC4 | 607 | 647 | 39.8 | 9.50E-09 |
| 992 | zf-C3HC4 | 467 | 507 | 27.5 | 4.70E-05 |
| 993 | zf-C3HC4 | 155 | 195 | 38.7 | 2.00E-08 |
| 994 | zf-C3HC4 | 127 | 167 | 27.6 | 4.60E-05 |
| 995 | zf-C3HC4 | 33 | 73 | 34.2 | 4.60E-07 |
| 996 | Skp1_POZ | 5 | 65 | 99.6 | 9.60E-27 |
| 996 | Skp1 | 91 | 168 | 186.3 | 7.40E-53 |
| 997 | Skp1 | 90 | 164 | 53.7 | 6.00E-13 |
| 998 | Skp1_POZ | 8 | 68 | 123.8 | 4.80E-34 |

TABLE 22-continued

| PEP SEQ ID | Pfam domain | Start | End | score | E-value |
|---|---|---|---|---|---|
| 998 | Skp1 | 99 | 176 | 192.8 | 8.40E−55 |
| 999 | LRR_2 | 174 | 201 | 6.7 | 1.90E+00 |
| 999 | LRR_2 | 301 | 325 | 7.2 | 1.60E+00 |
| 1000 | F-box | 15 | 63 | 21.2 | 3.70E−03 |
| 1000 | LRR_1 | 168 | 190 | 12.6 | 1.30E+00 |
| 1002 | F-box | 17 | 64 | 17.6 | 4.70E−02 |
| 1002 | LRR_1 | 299 | 325 | 8.6 | 7.10E+00 |
| 1002 | LRR_2 | 299 | 323 | 14.3 | 1.80E−01 |
| 1003 | Response_reg | 42 | 177 | 69.4 | 1.20E−17 |
| 1004 | zf-CHY | 35 | 113 | 119.1 | 1.30E−32 |
| 1004 | zf-C3HC4 | 166 | 208 | 33.3 | 8.40E−07 |
| 1005 | zf-CHY | 59 | 142 | 141.2 | 2.80E−39 |
| 1005 | zf-C3HC4 | 195 | 237 | 32.4 | 1.60E−06 |
| 1006 | MtN3_slv | 9 | 98 | 86.2 | 1.00E−22 |
| 1006 | MtN3_slv | 132 | 218 | 124.5 | 2.90E−34 |
| 1007 | zf-C3HC4 | 215 | 256 | 16.1 | 3.40E−03 |
| 1008 | PHD | 198 | 248 | 56.1 | 1.10E−13 |
| 1009 | F-box | 17 | 64 | 35.9 | 1.40E−07 |
| 1010 | F-box | 22 | 69 | 26.7 | 8.20E−05 |
| 1011 | F-box | 9 | 56 | 34.8 | 3.00E−07 |
| 1011 | Kelch_1 | 97 | 153 | 36.7 | 8.30E−08 |
| 1011 | Kelch_2 | 97 | 153 | 21.8 | 2.50E−03 |
| 1011 | Kelch_2 | 155 | 201 | 30.3 | 6.70E−06 |
| 1011 | Kelch_1 | 155 | 201 | 54.1 | 4.50E−13 |
| 1011 | Kelch_1 | 285 | 339 | 30.1 | 8.00E−06 |
| 1012 | F-box | 76 | 123 | 33.2 | 9.30E−07 |
| 1012 | Kelch_1 | 167 | 213 | 33.5 | 7.40E−07 |
| 1012 | Kelch_1 | 215 | 262 | 52.1 | 1.80E−12 |
| 1012 | Kelch_2 | 215 | 262 | 15.7 | 1.70E−01 |
| 1013 | F-box | 26 | 73 | 33.6 | 6.90E−07 |
| 1013 | Kelch_2 | 116 | 162 | 19.9 | 8.90E−03 |
| 1013 | Kelch_1 | 116 | 162 | 42.2 | 1.70E−09 |
| 1013 | Kelch_2 | 164 | 210 | 18.4 | 2.70E−02 |
| 1013 | Kelch_1 | 164 | 210 | 21.6 | 2.90E−03 |
| 1014 | zf-C3HC4 | 49 | 91 | 40.7 | 5.00E−09 |
| 1017 | Prp19 | 64 | 133 | 161.6 | 2.10E−45 |
| 1017 | WD40 | 253 | 291 | 47.2 | 5.40E−11 |
| 1017 | WD40 | 298 | 336 | 33.4 | 8.10E−07 |
| 1017 | WD40 | 384 | 421 | 32.2 | 1.80E−06 |
| 1018 | zf-C3HC4 | 36 | 81 | 26.6 | 8.90E−05 |
| 1019 | zf-C3HC4 | 58 | 103 | 34.3 | 4.30E−07 |
| 1020 | TPR_1 | 14 | 47 | 22.2 | 1.80E−03 |
| 1020 | TPR_2 | 14 | 47 | 20.6 | 5.70E−03 |
| 1020 | TPR_2 | 48 | 81 | 23.5 | 7.80E−04 |
| 1020 | TPR_1 | 48 | 81 | 33.1 | 9.60E−07 |
| 1020 | TPR_1 | 82 | 115 | 12.8 | 1.60E−01 |
| 1020 | TPR_2 | 82 | 115 | 21.1 | 4.10E−03 |
| 1020 | U-box | 195 | 269 | 132.5 | 1.20E−36 |
| 1021 | zf-C3HC4 | 24 | 64 | 27.8 | 3.90E−05 |
| 1022 | F-box | 195 | 243 | 23.8 | 5.90E−04 |
| 1022 | Kelch_1 | 292 | 340 | 17.6 | 3.90E−02 |
| 1022 | Kelch_2 | 292 | 340 | 15.9 | 1.50E−01 |
| 1022 | Kelch_2 | 345 | 392 | 33.6 | 7.10E−07 |
| 1022 | Kelch_1 | 345 | 392 | 17.2 | 4.40E−02 |
| 1022 | Kelch_1 | 397 | 445 | 13.4 | 1.20E−01 |
| 1022 | Kelch_2 | 449 | 501 | 27.6 | 4.40E−05 |
| 1022 | Kelch_2 | 516 | 564 | 26.4 | 9.90E−05 |
| 1023 | F-box | 205 | 253 | 28.5 | 2.40E−05 |
| 1023 | Kelch_1 | 300 | 348 | 17.8 | 3.70E−02 |
| 1023 | Kelch_2 | 300 | 348 | 17.8 | 3.90E−02 |
| 1023 | Kelch_2 | 353 | 400 | 24.4 | 4.10E−04 |
| 1023 | Kelch_1 | 405 | 453 | 12.7 | 1.40E−01 |
| 1023 | Kelch_2 | 458 | 509 | 18.3 | 2.80E−02 |
| 1023 | Kelch_2 | 518 | 566 | 32.8 | 1.20E−06 |
| 1024 | Cellulose_synt | 167 | 977 | 2072.7 | 0.00E+00 |
| 1025 | Cellulose_synt | 254 | 1069 | 2130.3 | 0.00E+00 |
| 1028 | zf-C3HC4 | 22 | 64 | 22 | 8.20E−04 |
| 1029 | F-box | 32 | 79 | 35.9 | 1.40E−07 |
| 1029 | LysM | 109 | 152 | 29.7 | 1.00E−05 |
| 1030 | Sina | 121 | 320 | 442.6 | 5.20E−130 |
| 1031 | F-box | 18 | 65 | 37.6 | 4.20E−08 |
| 1034 | F-box | 18 | 66 | 31 | 4.10E−06 |
| 1035 | SPX | 1 | 167 | 88.9 | 1.50E−23 |
| 1035 | zf-C3HC4 | 238 | 286 | 16.9 | 2.80E−03 |
| 1037 | Cullin | 15 | 237 | 52.9 | 4.60E−14 |
| 1038 | zf-C3HC4 | 227 | 270 | 35.6 | 1.70E−07 |
| 1039 | zf-C3HC4 | 361 | 398 | 39.6 | 1.10E−08 |
| 1040 | Melibiase | 34 | 362 | −25.7 | 2.30E−14 |
| 1041 | Copine | 80 | 227 | 281 | 2.30E−81 |
| 1042 | F-box | 36 | 83 | 31.8 | 2.40E−06 |
| 1046 | F-box | 1 | 47 | 20.9 | 4.70E−03 |
| 1046 | LRR_2 | 150 | 174 | 14.4 | 1.70E−01 |
| 1047 | F-box | 11 | 59 | 25.9 | 1.40E−04 |
| 1048 | U-box | 5 | 78 | 69.7 | 9.30E−18 |
| 1049 | Glycos_transf_1 | 465 | 648 | 59.4 | 1.20E−14 |
| 1049 | S6PP | 701 | 942 | −88.5 | 1.40E−04 |
| 1050 | Pkinase | 491 | 759 | 187.9 | 2.50E−53 |
| 1050 | Ribonuc_2-5A | 764 | 890 | 261.8 | 1.40E−75 |
| 1052 | Pkinase | 77 | 345 | 187.9 | 2.50E−53 |
| 1052 | Ribonuc_2-5A | 350 | 476 | 261.8 | 1.40E−75 |
| 1053 | Pkinase | 674 | 980 | 198.2 | 1.90E−56 |
| 1053 | Ribonuc_2-5A | 985 | 1115 | 256.7 | 4.80E−74 |
| 1055 | Pkinase | 101 | 407 | 198.2 | 1.90E−56 |
| 1055 | Ribonuc_2-5A | 412 | 542 | 256.7 | 4.80E−74 |
| 1056 | dCMP_cyt_deam_1 | 218 | 319 | 145.6 | 1.30E−40 |
| 1057 | Aldo_ket_red | 7 | 285 | 442 | 8.10E−130 |
| 1058 | Aldo_ket_red | 5 | 292 | 465.6 | 6.20E−137 |
| 1060 | SOH1 | 18 | 112 | 205.8 | 9.90E−59 |
| 1061 | dCMP_cyt_deam_1 | 1 | 107 | 117.9 | 2.80E−32 |
| 1062 | Put_Phosphatase | 4 | 229 | −87.8 | 7.10E−04 |
| 1063 | NAF1 | 104 | 273 | 372.4 | 7.00E−109 |
| 1064 | Aldo_ket_red | 10 | 289 | 204.4 | 2.70E−58 |
| 1065 | Glutaredoxin | 19 | 85 | 72.9 | 1.10E−18 |
| 1066 | TPT | 156 | 299 | 163.8 | 4.30E−46 |
| 1067 | DUF850 | 2 | 230 | 517.4 | 1.60E−152 |
| 1068 | LEA_2 | 17 | 166 | 309.5 | 6.20E−90 |
| 1069 | ABA_WDS | 43 | 96 | 102.9 | 9.40E−28 |
| 1070 | ABA_WDS | 51 | 104 | 105.7 | 1.40E−28 |
| 1071 | LEA_2 | 30 | 179 | 280.9 | 2.40E−81 |
| 1072 | LEA_2 | 30 | 179 | 300.6 | 2.90E−87 |
| 1073 | ABA_WDS | 54 | 107 | 105.1 | 2.10E−28 |
| 1074 | Sigma70_r2 | 260 | 330 | 69.1 | 1.50E−17 |
| 1074 | Sigma70_r3 | 334 | 414 | 67.5 | 4.20E−17 |
| 1074 | Sigma70_r4 | 433 | 485 | 38.5 | 2.30E−08 |
| 1075 | Sigma70_r2 | 314 | 384 | 83.9 | 4.80E−22 |
| 1075 | Sigma70_r3 | 388 | 469 | 76.3 | 9.60E−20 |
| 1075 | Sigma70_r4 | 482 | 535 | 73.1 | 8.80E−19 |
| 1076 | Sigma70_r2 | 302 | 372 | 70.7 | 4.80E−18 |
| 1076 | Sigma70_r3 | 376 | 457 | 95.4 | 1.70E−25 |
| 1076 | Sigma70_r4 | 469 | 522 | 98.3 | 2.30E−26 |
| 1077 | Bromodomain | 61 | 150 | 114.6 | 2.80E−31 |
| 1078 | Homeobox | 70 | 124 | 73.7 | 5.70E−19 |
| 1078 | HALZ | 125 | 169 | 43.9 | 5.50E−10 |
| 1079 | bZIP_1 | 118 | 179 | 60.2 | 6.60E−15 |
| 1079 | bZIP_2 | 118 | 172 | 40.5 | 5.90E−09 |
| 1080 | MFMR | 1 | 156 | 268.9 | 1.00E−77 |
| 1080 | bZIP_2 | 244 | 298 | 40 | 8.10E−09 |
| 1080 | bZIP_1 | 244 | 308 | 89.8 | 8.30E−24 |
| 1081 | Remorin_C | 402 | 512 | 145 | 2.00E−40 |
| 1082 | Remorin_N | 23 | 83 | 48 | 3.20E−11 |
| 1082 | Remorin_C | 85 | 194 | 165.5 | 1.40E−46 |
| 1083 | Myb_DNA-binding | 39 | 90 | 48.5 | 2.30E−11 |
| 1084 | Homeobox | 77 | 131 | 77.3 | 4.70E−20 |
| 1084 | HALZ | 132 | 176 | 65.4 | 1.80E−16 |
| 1085 | Homeobox | 77 | 131 | 77.3 | 4.70E−20 |
| 1085 | HALZ | 132 | 176 | 70.2 | 6.40E−18 |
| 1086 | HSF_DNA-bind | 11 | 170 | 148.9 | 1.30E−41 |
| 1088 | HSF_DNA-bind | 13 | 167 | 170.8 | 3.60E−48 |
| 1089 | HSF_DNA-bind | 15 | 219 | 144 | 4.10E−40 |
| 1090 | AUX_IAA | 18 | 218 | 231.9 | 1.40E−66 |
| 1091 | AUX_IAA | 19 | 219 | 97.9 | 3.00E−26 |
| 1092 | SRF-TF | 9 | 59 | 111.1 | 3.30E−30 |
| 1092 | K-box | 48 | 144 | 138 | 2.60E−38 |
| 1093 | SRF-TF | 9 | 59 | 120.8 | 3.90E−33 |
| 1093 | K-box | 75 | 174 | 154.8 | 2.20E−43 |
| 1094 | SRF-TF | 9 | 59 | 111.5 | 2.40E−30 |
| 1094 | K-box | 73 | 173 | 55.8 | 1.50E−13 |
| 1095 | SRF-TF | 9 | 59 | 109.7 | 8.30E−30 |
| 1095 | K-box | 71 | 170 | 112.4 | 1.30E−30 |
| 1096 | SRF-TF | 9 | 59 | 120.7 | 4.20E−33 |
| 1096 | K-box | 76 | 173 | 128.5 | 1.80E−35 |
| 1097 | SRF-TF | 9 | 59 | 113.1 | 8.30E−31 |
| 1097 | K-box | 71 | 170 | 105.8 | 1.30E−28 |
| 1098 | SRF-TF | 9 | 59 | 120.8 | 3.90E−33 |

TABLE 22-continued

| PEP SEQ ID | Pfam domain | Start | End | score | E-value |
|---|---|---|---|---|---|
| 1098 | K-box | 75 | 174 | 154.8 | 2.20E−43 |
| 1099 | zf-C2H2 | 35 | 58 | 19.5 | 1.20E−02 |
| 1100 | LIM | 10 | 67 | 55.9 | 1.30E−13 |
| 1100 | LIM | 105 | 162 | 67.2 | 5.10E−17 |
| 1101 | Myb_DNA-binding | 5 | 57 | 34.1 | 5.00E−07 |
| 1101 | Linker_histone | 122 | 190 | 14.4 | 2.80E−04 |
| 1102 | Myb_DNA-binding | 14 | 61 | 44.9 | 2.70E−10 |
| 1102 | Myb_DNA-binding | 67 | 112 | 46 | 1.30E−10 |
| 1103 | Myb_DNA-binding | 11 | 57 | 59.3 | 1.30E−14 |
| 1103 | Myb_DNA-binding | 63 | 108 | 48.9 | 1.70E−11 |
| 1104 | Myb_DNA-binding | 14 | 61 | 51.9 | 2.20E−12 |
| 1104 | Myb_DNA-binding | 67 | 112 | 50.8 | 4.50E−12 |
| 1105 | NAM | 23 | 158 | 278.5 | 1.30E−80 |
| 1106 | MED7 | 4 | 169 | 270.1 | 4.40E−78 |
| 1107 | zf-LSD1 | 27 | 51 | 43.6 | 6.70E−10 |
| 1107 | zf-LSD1 | 66 | 90 | 54.8 | 2.80E−13 |
| 1107 | zf-LSD1 | 104 | 128 | 55.2 | 2.20E−13 |
| 1108 | Hydrolase | 18 | 209 | 95.4 | 1.70E−25 |
| 1109 | zf-C3HC4 | 349 | 389 | 38.5 | 2.30E−08 |
| 1110 | zf-C3HC4 | 244 | 284 | 41.2 | 3.40E−09 |
| 1111 | zf-CHY | 35 | 113 | 119.1 | 1.30E−32 |
| 1111 | zf-C3HC4 | 166 | 208 | 33.3 | 8.40E−07 |
| 1112 | Ank | 50 | 82 | 34.2 | 4.60E−07 |
| 1112 | Ank | 83 | 115 | 32.9 | 1.20E−06 |
| 1112 | Ank | 117 | 148 | 12.8 | 4.40E−01 |
| 1112 | Ank | 180 | 212 | 40.8 | 4.80E−09 |
| 1112 | Ank | 223 | 255 | 37.4 | 5.00E−08 |
| 1112 | zf-C3HC4 | 321 | 370 | 23.9 | 5.30E−04 |
| 1113 | zf-B_box | 1 | 47 | 42.6 | 1.30E−09 |
| 1113 | zf-B_box | 48 | 90 | 24.8 | 3.00E−04 |
| 1113 | CCT | 356 | 394 | 69.7 | 9.50E−18 |
| 1114 | GRAS | 154 | 464 | 462.7 | 4.60E−136 |
| 1115 | TFIIS | 1 | 93 | 31.9 | 2.20E−06 |
| 1115 | TFIIS_M | 189 | 317 | 173.9 | 4.10E−49 |
| 1115 | TFIIS_C | 328 | 366 | 86.5 | 8.20E−23 |
| 1116 | zf-B_box | 1 | 47 | 38.8 | 1.80E−08 |
| 1116 | zf-B_box | 55 | 102 | 38.5 | 2.30E−08 |
| 1117 | Copine | 111 | 259 | 298.9 | 9.70E−87 |
| 1118 | Copine | 111 | 259 | 298.3 | 1.40E−86 |
| 1120 | zf-CCCH | 35 | 61 | 16.6 | 8.40E−03 |
| 1120 | zf-CCCH | 95 | 121 | 30.7 | 5.20E−06 |
| 1120 | KH_1 | 246 | 310 | 63.8 | 5.70E−16 |
| 1120 | zf-CCCH | 324 | 349 | 38.8 | 1.90E−08 |
| 1121 | AUX_IAA | 7 | 222 | 240.4 | 3.90E−69 |
| 1122 | zf-B_box | 1 | 47 | 39 | 1.70E−08 |
| 1122 | zf-B_box | 51 | 96 | 46.8 | 7.50E−11 |
| 1124 | SRF-TF | 9 | 59 | 118.2 | 2.30E−32 |
| 1124 | K-box | 75 | 174 | 158.7 | 1.50E−44 |
| 1125 | SRF-TF | 9 | 59 | 110.5 | 4.80E−30 |
| 1125 | K-box | 75 | 174 | 141.1 | 2.90E−39 |
| 1126 | SRF-TF | 9 | 59 | 120.8 | 3.90E−33 |
| 1126 | K-box | 75 | 174 | 162.3 | 1.20E−45 |
| 1127 | SRF-TF | 9 | 59 | 124.4 | 3.10E−34 |
| 1127 | K-box | 75 | 174 | 167.9 | 2.60E−47 |
| 1128 | SRF-TF | 9 | 59 | 124.4 | 3.10E−34 |
| 1128 | K-box | 75 | 174 | 167.9 | 2.60E−47 |
| 1129 | FLO_LFY | 1 | 395 | 1029.1 | 0.00E+00 |
| 1130 | Hydrolase | 114 | 295 | 47.5 | 4.50E−11 |
| 1131 | Hydrolase | 130 | 317 | 50 | 8.20E−12 |
| 1132 | Hydrolase | 110 | 298 | 45.1 | 2.30E−10 |
| 1133 | AP2 | 15 | 80 | 145.7 | 1.20E−40 |
| 1140 | Pkinase | 20 | 275 | 350.4 | 3.00E−102 |
| 1140 | NAF | 314 | 374 | 120 | 6.50E−33 |
| 1141 | WD40 | 560 | 599 | 34.5 | 3.70E−07 |
| 1141 | WD40 | 646 | 683 | 30.4 | 6.10E−06 |
| 1142 | Pkinase | 139 | 401 | 317.6 | 2.30E−92 |
| 1143 | EMP24_GP25L | 76 | 137 | 56.3 | 1.00E−13 |
| 1144 | RRM_1 | 4 | 70 | 55.9 | 1.40E−13 |
| 1144 | zf-CCHC | 86 | 103 | 32.5 | 1.40E−06 |
| 1145 | Frigida | 112 | 414 | 431.3 | 1.30E−126 |
| 1146 | DUF810 | 175 | 1046 | 1901.1 | 0.00E+00 |
| 1147 | Dor1 | 21 | 369 | 478.8 | 6.60E−141 |
| 1148 | Alpha-amylase | 26 | 356 | 188.4 | 1.70E−53 |
| 1148 | Alpha-amyl_C2 | 357 | 415 | 103.2 | 7.90E−28 |
| 1149 | AT_hook | 99 | 111 | 7.4 | 1.20E+00 |
| 1149 | DUF296 | 126 | 246 | 177.4 | 3.60E−50 |
| 1150 | IMPDH | 23 | 491 | 672.5 | 3.20E−199 |
| 1150 | CBS | 53 | 218 | 21.4 | 8.00E−04 |
| 1151 | IMPDH | 35 | 512 | 774.3 | 7.60E−230 |
| 1151 | CBS | 119 | 235 | 89.6 | 9.60E−24 |
| 1152 | IMPDH | 7 | 473 | 831.3 | 5.20E−247 |
| 1152 | CBS | 91 | 206 | 91.4 | 2.80E−24 |
| 1153 | IMPDH | 12 | 486 | 777.4 | 8.30E−231 |
| 1153 | CBS | 96 | 218 | 104.2 | 3.70E−28 |
| 1154 | zf-CCCH | 38 | 64 | 22.1 | 1.60E−03 |
| 1154 | zf-CCCH | 105 | 131 | 33.5 | 7.60E−07 |
| 1154 | KH_1 | 174 | 236 | 56.7 | 7.50E−14 |
| 1154 | zf-CCCH | 274 | 299 | 46.2 | 1.10E−10 |
| 1155 | Response_reg | 21 | 134 | 102.7 | 1.10E−27 |
| 1155 | Myb_DNA-binding | 214 | 264 | 50.1 | 7.50E−12 |
| 1156 | zf-C3HC4 | 251 | 291 | 37.3 | 5.10E−08 |
| 1157 | MFS_1 | 129 | 549 | 28.1 | 1.60E−05 |
| 1158 | Sugar_tr | 34 | 472 | −51.8 | 3.00E−05 |
| 1159 | AP2 | 15 | 80 | 145.2 | 1.70E−40 |
| 1160 | AP2 | 7 | 72 | 145.6 | 1.30E−40 |
| 1161 | Pyridoxal_deC | 35 | 383 | 513.3 | 2.70E−151 |
| 1162 | AUX_IAA | 7 | 263 | 378.3 | 1.20E−110 |
| 1163 | Cyclin_N | 92 | 207 | 148.4 | 1.90E−41 |
| 1163 | Cyclin_C | 209 | 336 | 128.3 | 2.20E−35 |
| 1164 | Cyclin_N | 183 | 321 | 109.6 | 9.10E−30 |
| 1166 | zf-Dof | 105 | 167 | 142.4 | 1.20E−39 |
| 1167 | NAM | 52 | 179 | 232 | 1.30E−66 |
| 1168 | NAM | 18 | 145 | 252.2 | 1.10E−72 |
| 1169 | p450 | 41 | 477 | 129.4 | 9.70E−36 |
| 1170 | LRRNT_2 | 23 | 63 | 40.6 | 5.40E−09 |
| 1170 | LRR_1 | 90 | 112 | 14 | 5.60E−01 |
| 1170 | LRR_1 | 114 | 136 | 22.7 | 1.30E−03 |
| 1170 | LRR_1 | 162 | 184 | 13.2 | 9.40E−01 |
| 1170 | LRR_1 | 186 | 208 | 9.7 | 4.40E+00 |
| 1170 | LRR_1 | 234 | 256 | 16 | 1.30E−01 |
| 1170 | LRR_1 | 258 | 280 | 12.4 | 1.40E+00 |
| 1170 | LRR_1 | 282 | 304 | 12.3 | 1.40E+00 |
| 1170 | LRR_1 | 306 | 328 | 13.3 | 8.70E−01 |
| 1170 | LRR_1 | 354 | 376 | 13.9 | 5.90E−01 |
| 1170 | LRR_1 | 402 | 425 | 11.7 | 1.80E+00 |
| 1170 | LRR_1 | 448 | 470 | 13.8 | 6.10E−01 |
| 1170 | LRR_1 | 472 | 494 | 9.8 | 4.20E+00 |
| 1170 | LRR_1 | 519 | 541 | 14.8 | 3.10E−01 |
| 1170 | LRR_1 | 543 | 565 | 9.6 | 4.50E+00 |
| 1170 | LRR_1 | 567 | 589 | 16.1 | 1.20E−01 |
| 1170 | LRR_1 | 591 | 613 | 18.7 | 2.20E−02 |
| 1170 | LRR_1 | 615 | 638 | 10.8 | 2.70E+00 |
| 1170 | LRR_1 | 748 | 771 | 13.4 | 8.20E−01 |
| 1170 | LRR_1 | 772 | 795 | 9.7 | 4.50E+00 |
| 1170 | LRR_1 | 824 | 846 | 16.4 | 1.00E−01 |
| 1170 | LRR_1 | 848 | 870 | 11.8 | 1.80E+00 |
| 1170 | Pkinase_Tyr | 1002 | 1275 | 118.5 | 1.80E−32 |
| 1170 | Pkinase | 1002 | 1275 | 145.9 | 1.10E−40 |
| 1171 | LRRNT_2 | 21 | 60 | 65.1 | 2.30E−16 |
| 1171 | LRR_1 | 139 | 158 | 8.6 | 7.00E+00 |
| 1171 | LRR_1 | 185 | 207 | 18.2 | 3.00E−02 |
| 1171 | LRR_1 | 209 | 231 | 12.5 | 1.30E+00 |
| 1171 | LRR_1 | 233 | 255 | 16.3 | 1.10E−01 |
| 1171 | LRR_1 | 259 | 281 | 17.6 | 4.40E−02 |
| 1171 | LRR_1 | 283 | 306 | 13.9 | 5.70E−01 |
| 1171 | LRR_1 | 308 | 330 | 11.5 | 2.00E+00 |
| 1171 | LRR_1 | 332 | 354 | 11.8 | 3.20E+00 |
| 1171 | LRR_1 | 357 | 379 | 12.1 | 1.50E+00 |
| 1171 | LRR_1 | 381 | 403 | 10 | 3.90E+00 |
| 1171 | LRR_1 | 429 | 451 | 14.3 | 4.30E−01 |
| 1171 | LRR_1 | 453 | 475 | 12.3 | 1.40E+00 |
| 1171 | LRR_1 | 477 | 499 | 12.9 | 1.10E+00 |
| 1171 | LRR_1 | 501 | 520 | 11.1 | 2.40E+00 |
| 1171 | LRR_1 | 593 | 615 | 15.6 | 1.80E−01 |
| 1171 | LRR_1 | 617 | 639 | 15.7 | 1.70E−01 |
| 1171 | LRR_1 | 641 | 663 | 12.1 | 1.50E+00 |
| 1171 | Pkinase | 824 | 1098 | 139.3 | 1.10E−38 |
| 1171 | Pkinase_Tyr | 824 | 1098 | 124 | 4.20E−34 |
| 1172 | LRR_1 | 199 | 219 | 8.6 | 7.20E+00 |
| 1172 | LRR_1 | 221 | 244 | 16.5 | 9.50E−02 |
| 1172 | LRR_1 | 246 | 268 | 14.3 | 4.40E−01 |
| 1172 | LRR_1 | 270 | 293 | 17.5 | 4.70E−02 |
| 1172 | LRR_1 | 295 | 317 | 11.9 | 1.70E+00 |
| 1172 | LRR_1 | 319 | 342 | 13.5 | 8.00E−01 |

TABLE 22-continued

| PEP SEQ ID | Pfam domain | Start | End | score | E-value |
|---|---|---|---|---|---|
| 1172 | LRR_1 | 345 | 367 | 13.3 | 9.00E-01 |
| 1172 | LRR_1 | 369 | 391 | 15.1 | 2.50E-01 |
| 1172 | LRR_1 | 393 | 415 | 10.3 | 3.40E+00 |
| 1172 | LRR_1 | 417 | 439 | 16.4 | 1.00E-01 |
| 1172 | LRR_1 | 441 | 463 | 13.5 | 7.80E-01 |
| 1172 | LRR_1 | 465 | 487 | 14.3 | 4.50E-01 |
| 1172 | LRR_1 | 489 | 511 | 13.8 | 6.20E-01 |
| 1172 | LRR_1 | 582 | 604 | 10.8 | 2.70E+00 |
| 1172 | LRR_1 | 630 | 652 | 19.3 | 1.40E-02 |
| 1172 | LRR_1 | 653 | 674 | 16.4 | 1.10E-01 |
| 1172 | Pkinase_Tyr | 807 | 1080 | 114.8 | 2.50E-31 |
| 1172 | Pkinase | 807 | 1080 | 161.6 | 2.00E-45 |
| 1173 | FAD_binding_4 | 55 | 200 | 30 | 8.20E-06 |
| 1174 | FAD_binding_4 | 55 | 200 | 29.3 | 1.40E-05 |
| 1175 | Sterol_desat | 35 | 210 | 87 | 5.70E-23 |
| 1176 | Sterol_desat | 35 | 246 | 180.6 | 3.90E-51 |
| 1177 | Sterol_desat | 37 | 248 | 184.2 | 3.20E-52 |
| 1178 | Sterol_desat | 43 | 254 | 215.6 | 1.10E-61 |
| 1179 | Peptidase_S10 | 41 | 465 | 669.2 | 3.10E-198 |
| 1180 | Peptidase_S10 | 56 | 474 | 711.4 | 6.30E-211 |
| 1181 | F-box | 205 | 253 | 30.2 | 7.10E-06 |
| 1181 | Kelch_1 | 300 | 348 | 18.6 | 2.20E-02 |
| 1181 | Kelch_2 | 300 | 348 | 23.7 | 6.70E-04 |
| 1181 | Kelch_1 | 352 | 400 | 8.4 | 4.30E-01 |
| 1181 | Kelch_2 | 353 | 400 | 26.4 | 1.00E-04 |
| 1181 | Kelch_1 | 405 | 453 | 15.4 | 7.00E-02 |
| 1181 | Kelch_2 | 524 | 572 | 34.3 | 4.20E-07 |
| 1182 | F-box | 272 | 320 | 28.5 | 2.40E-05 |
| 1182 | Kelch_1 | 367 | 415 | 21 | 4.10E-03 |
| 1182 | Kelch_2 | 367 | 415 | 20.6 | 5.50E-03 |
| 1182 | Kelch_2 | 420 | 467 | 24.4 | 4.10E-04 |
| 1182 | Kelch_2 | 471 | 520 | 15.1 | 2.50E-01 |
| 1182 | Kelch_1 | 472 | 520 | 12 | 1.70E-01 |
| 1182 | Kelch_1 | 525 | 576 | 8.7 | 4.00E-01 |
| 1182 | Kelch_2 | 525 | 576 | 20 | 8.40E-03 |
| 1182 | Kelch_2 | 586 | 634 | 29.8 | 9.70E-06 |
| 1183 | ADH_N | 36 | 165 | 116.7 | 6.40E-32 |
| 1183 | ADH_zinc_N | 196 | 342 | 117 | 5.40E-32 |
| 1184 | ADH_N | 27 | 155 | 135.6 | 1.30E-37 |
| 1184 | ADH_zinc_N | 186 | 332 | 115.4 | 1.70E-31 |
| 1185 | ADH_N | 27 | 155 | 118.3 | 2.10E-32 |
| 1185 | ADH_zinc_N | 186 | 328 | 139.2 | 1.10E-38 |
| 1186 | ADH_N | 36 | 165 | 130.6 | 4.50E-36 |
| 1186 | ADH_zinc_N | 196 | 338 | 129.9 | 6.80E-36 |
| 1187 | ADH_N | 36 | 165 | 135 | 2.00E-37 |
| 1187 | ADH_zinc_N | 196 | 338 | 124.6 | 2.70E-34 |
| 1188 | ADH_N | 35 | 163 | 116.1 | 1.00E-31 |
| 1188 | ADH_zinc_N | 197 | 343 | 119.6 | 9.10E-33 |
| 1189 | ADH_N | 34 | 163 | 119.4 | 1.00E-32 |
| 1189 | ADH_zinc_N | 194 | 336 | 145.3 | 1.60E-40 |
| 1190 | ADH_N | 34 | 163 | 121.3 | 2.70E-33 |
| 1190 | ADH_zinc_N | 194 | 336 | 126.3 | 8.30E-35 |
| 1191 | TPT | 156 | 298 | 165.2 | 1.70E-46 |
| 1192 | TPT | 154 | 296 | 177.3 | 3.90E-50 |
| 1193 | TPT | 151 | 293 | 150.6 | 4.10E-42 |
| 1194 | Sugar_tr | 91 | 552 | 421.2 | 1.50E-123 |
| 1194 | MFS_1 | 95 | 511 | 85.3 | 1.80E-22 |
| 1195 | Cyclin_N | 61 | 193 | 117.1 | 5.00E-32 |
| 1195 | Cyclin_C | 195 | 326 | 36.6 | 8.70E-08 |
| 1196 | SAC3_GANP | 24 | 209 | 90.8 | 4.10E-24 |
| 1197 | SAC3_GANP | 20 | 211 | 214.5 | 2.30E-61 |
| 1198 | SAC3_GANP | 24 | 209 | 106.9 | 5.90E-29 |
| 1199 | SAC3_GANP | 24 | 209 | 122.2 | 1.40E-33 |
| 1200 | WD40 | 183 | 220 | 26.2 | 1.20E-04 |
| 1200 | WD40 | 289 | 328 | 33.8 | 5.90E-07 |
| 1201 | WD40 | 204 | 241 | 26.2 | 1.20E-04 |
| 1201 | WD40 | 311 | 350 | 33.8 | 5.90E-07 |
| 1202 | CHASE | 86 | 298 | 339 | 8.00E-99 |
| 1202 | HisKA | 359 | 424 | 83.1 | 8.50E-22 |
| 1202 | HATPase_c | 471 | 654 | 130.1 | 6.30E-36 |
| 1202 | Response_reg | 829 | 963 | 111.6 | 2.20E-30 |
| 1203 | CHASE | 198 | 411 | 356.8 | 3.40E-104 |
| 1203 | HisKA | 472 | 537 | 93.4 | 6.90E-25 |
| 1203 | HATPase_c | 584 | 759 | 124.3 | 3.50E-34 |
| 1203 | Response_reg | 945 | 1068 | 106.2 | 9.70E-29 |
| 1204 | CHASE | 302 | 526 | 342.6 | 6.40E-100 |
| 1204 | HisKA | 587 | 652 | 90.2 | 6.20E-24 |
| 1204 | HATPase_c | 699 | 866 | 132.7 | 9.90E-37 |
| 1204 | Response_reg | 1035 | 1170 | 106.9 | 6.00E-29 |
| 1205 | CHASE | 163 | 389 | 347.6 | 2.10E-101 |
| 1205 | HisKA | 450 | 515 | 89.7 | 9.00E-24 |
| 1205 | HATPase_c | 562 | 722 | 128.9 | 1.40E-35 |
| 1205 | Response_reg | 890 | 1025 | 92.6 | 1.20E-24 |
| 1206 | MFS_1 | 66 | 429 | 63.7 | 5.90E-16 |
| 1207 | MFS_1 | 69 | 432 | 56.4 | 9.20E-14 |
| 1208 | MFS_1 | 51 | 415 | 50.8 | 4.50E-12 |
| 1209 | CHASE | 110 | 321 | 288.1 | 1.70E-83 |
| 1209 | HisKA | 382 | 447 | 88.4 | 2.20E-23 |
| 1209 | HATPase_c | 494 | 682 | 112.8 | 9.90E-31 |
| 1209 | Response_reg | 869 | 1004 | 105.6 | 1.50E-28 |
| 1210 | PTR2 | 113 | 517 | 661.3 | 7.40E-196 |
| 1211 | PTR2 | 118 | 521 | 399.1 | 6.60E-117 |
| 1212 | PTR2 | 97 | 499 | 482.9 | 3.80E-142 |
| 1213 | PTR2 | 122 | 526 | 531.9 | 6.60E-157 |
| 1214 | PTR2 | 98 | 500 | 500.5 | 1.90E-147 |
| 1215 | AT_hook | 34 | 46 | 7.5 | 1.20E+00 |
| 1215 | DUF296 | 61 | 180 | 198.4 | 1.70E-56 |
| 1220 | BIR | 20 | 117 | 62.6 | 1.30E-15 |
| 1220 | BIR | 153 | 241 | 96.5 | 7.70E-26 |
| 1221 | AT_hook | 34 | 46 | 7.5 | 1.20E+00 |
| 1221 | DUF296 | 61 | 180 | 198.4 | 1.70E-56 |
| 1224 | Bap31 | 1 | 188 | 39.2 | 4.60E-11 |

TABLE 23

| Pfam domain name | Accession # | Gathering cutoff | Domain description |
|---|---|---|---|
| 14-3-3 | PF00244.10 | 25.0 | 14-3-3 protein |
| 2-Hacid_dh_C | PF02826.9 | -82.2 | D-isomer specific 2-hydroxyacid dehydrogenase, NAD binding domain |
| 2OG-FeII_Oxy | PF03171.10 | 11.5 | 2OG-Fe(II) oxygenase superfamily |
| AA_permease | PF00324.11 | -120.8 | Amino acid permease |
| ABA_WDS | PF02496.6 | 25.0 | ABA/WDS induced protein |
| ADH_N | PF08240.2 | -14.5 | Alcohol dehydrogenase GroES-like domain |
| ADH_zinc_N | PF00107.16 | 23.8 | Zinc-binding dehydrogenase |
| AP2 | PF00847.10 | 0.0 | AP2 domain |
| AT_hook | PF02178.9 | 3.6 | AT hook motif |
| AUX_IAA | PF02309.7 | -83.0 | AUX/IAA family |
| AdoHcyase | PF05221.7 | -205.2 | S-adenosyl-L-homocysteine hydrolase |
| AdoHcyase_NAD | PF00670.12 | -23.6 | S-adenosyl-L-homocysteine hydrolase, NAD binding domain |
| Aldedh | PF00171.12 | -209.3 | Aldehyde dehydrogenase family |
| Aldo_ket_red | PF00248.11 | -97.0 | Aldo/keto reductase family |
| Alpha-amyl_C2 | PF07821.3 | 25.0 | Alpha-amylase C-terminal beta-sheet domain |
| Alpha-amylase | PF00128.14 | -92.6 | Alpha amylase, catalytic domain |

TABLE 23-continued

| Pfam domain name | Accession # | Gathering cutoff | Domain description |
|---|---|---|---|
| Ank | PF00023.20 | 0.0 | Ankyrin repeat |
| Arm | PF00514.13 | 17.0 | Armadillo/beta-catenin-like repeat |
| Asp | PF00026.14 | −153.8 | Eukaryotic aspartyl protease |
| BCCT | PF02028.8 | −17.0 | BCCT family transporter |
| BIR | PF00653.12 | 0.0 | Inhibitor of Apoptosis domain |
| BRAP2 | PF07576.2 | 0.7 | BRCA1-associated protein 2 |
| BRCT | PF00533.16 | 27.8 | BRCA1 C Terminus (BRCT) domain |
| BTB | PF00651.21 | 6.2 | BTB/POZ domain |
| B_lectin | PF01453.15 | 28.2 | D-mannose binding lectin |
| Bap31 | PF05529.2 | −39.4 | B-cell receptor-associated protein 31-like |
| Bromodomain | PF00439.15 | 8.9 | Bromodomain |
| C1_1 | PF00130.12 | 10.5 | Phorbol esters/diacylglycerol binding domain (C1 domain) |
| C2 | PF00168.20 | 3.7 | C2 domain |
| CBFD_NFYB_HMF | PF00808.13 | 18.4 | Histone-like transcription factor (CBF/NF-Y) and archaeal histone |
| CBS | PF00571.18 | 17.5 | CBS domain pair |
| CCT | PF06203.4 | 25.0 | CCT motif |
| CHASE | PF03924.4 | 25.0 | CHASE domain |
| CK_II_beta | PF01214.9 | −106.0 | Casein kinase II regulatory subunit |
| CMAS | PF02353.10 | −177.9 | Cyclopropane-fatty-acyl-phospholipid synthase |
| Cellulose_synt | PF03552.5 | −257.9 | Cellulose synthase |
| Copine | PF07002.6 | −36.5 | Copine |
| Cu-oxidase | PF00394.12 | −18.9 | Multicopper oxidase |
| Cu-oxidase_2 | PF07731.4 | −5.8 | Multicopper oxidase |
| Cu-oxidase_3 | PF07732.5 | 10.0 | Multicopper oxidase |
| Cu_bind_like | PF02298.8 | −16.4 | Plastocyanin-like domain |
| Cullin | PF00888.12 | −33.3 | Cullin family |
| Cyclin_C | PF02984.9 | −13.0 | Cyclin, C-terminal domain |
| Cyclin_N | PF00134.13 | −14.7 | Cyclin, N-terminal domain |
| DAD | PF02109.6 | 25.0 | DAD family |
| DAGK_acc | PF00609.10 | −50.0 | Diacylglycerol kinase accessory domain |
| DAGK_cat | PF00781.14 | −5.7 | Diacylglycerol kinase catalytic domain (presumed) |
| DPBB_1 | PF03330.8 | 5.3 | Rare lipoprotein A (RlpA)-like double-psi beta-barrel |
| DUF1313 | PF07011.2 | 25.0 | Protein of unknown function (DUF1313) |
| DUF221 | PF02714.6 | 25.0 | Domain of unknown function DUF221 |
| DUF231 | PF03005.6 | −58.0 | Arabidopsis proteins of unknown function |
| DUF296 | PF03479.5 | −11.0 | Domain of unknown function (DUF296) |
| DUF580 | PF04515.3 | 25.0 | Protein of unknown function, DUF580 |
| DUF6 | PF00892.11 | 20.8 | Integral membrane protein DUF6 |
| DUF810 | PF05664.2 | 25.0 | Protein of unknown function (DUF810) |
| DUF850 | PF05863.3 | 25.0 | Eukaryotic protein of unknown function (DUF850) |
| DUF914 | PF06027.3 | −193.0 | Eukaryotic protein of unknown function (DUF914) |
| DXP_redisom_C | PF08436.3 | 25.0 | 1-deoxy-D-xylulose 5-phosphate reductoisomerase C-terminal |
| DXP_reductoisom | PF02670.7 | −49.7 | 1-deoxy-D-xylulose 5-phosphate reductoisomerase |
| Dor1 | PF04124.3 | 25.0 | Dor1-like family |
| EMP24_GP25L | PF01105.14 | 10.0 | emp24/gp25L/p24 family/GOLD |
| Enolase_C | PF00113.12 | −71.2 | Enolase, C-terminal TIM barrel domain |
| Enolase_N | PF03952.6 | 11.3 | Enolase, N-terminal domain |
| Epimerase | PF01370.11 | −46.3 | NAD dependent epimerase/dehydratase family |
| Exo_endo_phos | PF03372.13 | 11.0 | Endonuclease/Exonuclease/phosphatase family |
| F-box | PF00646.23 | 13.9 | F-box domain |
| FAD_binding_4 | PF01565.13 | −8.1 | FAD binding domain |
| FAD_binding_6 | PF00970.14 | −11.4 | Oxidoreductase FAD-binding domain |
| FAT | PF02259.13 | 275.0 | FAT domain |
| FATC | PF02260.10 | 20.0 | FATC domain |
| FBPase | PF00316.10 | −170.3 | Fructose-1-6-bisphosphatase |
| FBPase_glpX | PF03320.4 | −198.1 | Bacterial fructose-1,6-bisphosphatase, glpX-encoded |
| FLO_LFY | PF01698.7 | −225.0 | Floricaula/Leafy protein |
| Flavodoxin_2 | PF02525.7 | −46.4 | Flavodoxin-like fold |
| Flavoprotein | PF02441.9 | 11.0 | Flavoprotein |
| Frigida | PF07899.2 | −62.5 | Frigida-like protein |
| G-alpha | PF00503.10 | −230.0 | G-protein alpha subunit |
| GAF | PF01590.16 | 23.0 | GAF domain |
| GH3 | PF03321.4 | −336.0 | GH3 auxin-responsive promoter |
| GRAS | PF03514.5 | −78.0 | GRAS family transcription factor |
| GST_C | PF00043.15 | 22.3 | Glutathione S-transferase, C-terminal domain |
| GST_N | PF02798.10 | 14.6 | Glutathione S-transferase, N-terminal domain |

TABLE 23-continued

| Pfam domain name | Accession # | Gathering cutoff | Domain description |
|---|---|---|---|
| Globin | PF00042.12 | −8.8 | Globin |
| Glutaredoxin | PF00462.14 | 17.2 | Glutaredoxin |
| Glyco_transf_20 | PF00982.11 | −243.6 | Glycosyltransferase family 20 |
| Glycos_transf_1 | PF00534.10 | −7.3 | Glycosyl transferases group 1 |
| HALZ | PF02183.8 | 17.0 | Homeobox associated leucine zipper |
| HATPase_c | PF02518.16 | 22.4 | Histidine kinase-, DNA gyrase B-, and HSP90-like ATPase |
| HD-ZIP_N | PF04618.3 | 25.0 | HD-ZIP protein N terminus |
| HEAT | PF02985.12 | 11.5 | HEAT repeat |
| HLH | PF00010.16 | 8.3 | Helix-loop-helix DNA-binding domain |
| HMG_box | PF00505.9 | 4.1 | HMG (high mobility group) box |
| HSF_DNA-bind | PF00447.8 | −70.0 | HSF-type DNA-binding |
| H_PPase | PF03030.7 | −377.0 | Inorganic H+ pyrophosphatase |
| Hexapep | PF00132.14 | 0.3 | Bacterial transferase hexapeptide (three repeats) |
| HisKA | PF00512.15 | 10.3 | His Kinase A (phosphoacceptor) domain |
| Histone | PF00125.14 | 17.4 | Core histone H2A/H2B/H3/H4 |
| Homeobox | PF00046.19 | −4.1 | Homeobox domain |
| Hpt | PF01627.13 | 25.0 | Hpt domain |
| Hydrolase | PF00702.16 | 13.6 | haloacid dehalogenase-like hydrolase |
| Hydrolase_3 | PF08282.2 | −64.8 | haloacid dehalogenase-like hydrolase |
| IMPDH | PF00478.15 | −190.6 | IMP dehydrogenase/GMP reductase domain |
| IPP-2 | PF04979.4 | −30.0 | Protein phosphatase inhibitor 2 (IPP-2) |
| IlvN | PF07991.2 | −75.8 | Acetohydroxy acid isomeroreductase, catalytic domain |
| K-box | PF01486.8 | 0.0 | K-box region |
| KH_1 | PF00013.19 | 10.5 | KH domain |
| KR | PF08659.1 | −74.3 | KR domain |
| Kelch_1 | PF01344.15 | 7.8 | Kelch motif |
| Kelch_2 | PF07646.5 | 14.0 | Kelch motif |
| LEA_2 | PF03168.4 | 25.0 | Late embryogenesis abundant protein |
| LEA_4 | PF02987.7 | 22.6 | Late embryogenesis abundant protein |
| LIM | PF00412.12 | 0.0 | LIM domain |
| LRRNT_2 | PF08263.3 | 18.6 | Leucine rich repeat N-terminal domain |
| LRR_1 | PF00560.23 | 7.7 | Leucine Rich Repeat |
| LRR_2 | PF07723.3 | 6.0 | Leucine Rich Repeat |
| Lactamase_B | PF00753.17 | 24.6 | Metallo-beta-lactamase superfamily |
| Linker_histone | PF00538.9 | −8.0 | linker histone H1 and H5 family |
| LysM | PF01476.10 | 20.0 | LysM domain |
| MED7 | PF05983.2 | −39.2 | MED7 protein |
| MFMR | PF07777.2 | −46.7 | G-box binding protein MFMR |
| MFS_1 | PF07690.6 | 23.5 | Major Facilitator Superfamily |
| MIF4G | PF02854.9 | −6.0 | MIF4G domain |
| MIF4G_like | PF09088.1 | 25.0 | MIF4G like |
| MIF4G_like_2 | PF09090.1 | −46.1 | MIF4G like |
| MatE | PF01554.9 | −4.8 | MatE |
| Melibiase | PF02065.9 | −228.6 | Melibiase |
| Methyltransf_11 | PF08241.2 | 20.9 | Methyltransferase domain |
| Methyltransf_12 | PF08242.2 | 23.0 | Methyltransferase domain |
| Mito_carr | PF00153.17 | 0.0 | Mitochondrial carrier protein |
| Mlo | PF03094.6 | −263.0 | Mlo family |
| MtN3_slv | PF03083.6 | 9.7 | MtN3/saliva family |
| Myb_DNA-binding | PF00249.21 | 14.0 | Myb-like DNA-binding domain |
| NAD_binding_1 | PF00175.11 | −3.9 | Oxidoreductase NAD-binding domain |
| NAD_binding_4 | PF07993.2 | −87.7 | Male sterility protein |
| NAF | PF03822.5 | 4.5 | NAF domain |
| NAF1 | PF05492.3 | −43.3 | NAF1 domain |
| NAM | PF02365.6 | −19.0 | No apical meristem (NAM) protein |
| NAS | PF03059.6 | −60.0 | Nicotianamine synthase protein |
| NPH3 | PF03000.5 | 25.0 | NPH3 family |
| Na_H_Exchanger | PF00999.11 | −67.9 | Sodium/hydrogen exchanger family |
| OPT | PF03169.6 | −238.6 | OPT oligopeptide transporter protein |
| Orn_Arg_deC_N | PF02784.7 | −76.0 | Pyridoxal-dependent decarboxylase, pyridoxal binding domain |
| Orn_DAP_Arg_deC | PF00278.12 | 6.7 | Pyridoxal-dependent decarboxylase, C-terminal sheet domain |
| P-II | PF00543.12 | −29.0 | Nitrogen regulatory protein P-II |
| PA | PF02225.12 | 13.0 | PA domain |
| PAN_1 | PF00024.16 | 1.4 | PAN domain |
| PAN_2 | PF08276.2 | −4.9 | PAN-like domain |
| PB1 | PF00564.15 | 12.3 | PB1 domain |
| PBP | PF01161.10 | −20.6 | Phosphatidylethanolamine-binding protein |
| PEMT | PF04191.3 | 25.0 | Phospholipid methyltransferase |
| PEP-utilizers | PF00391.13 | 0.6 | PEP-utilising enzyme, mobile domain |
| PEP-utilizers_C | PF02896.8 | −173.0 | PEP-utilising enzyme, TIM barrel domain |
| PHD | PF00628.19 | 25.9 | PHD-finger |

TABLE 23-continued

| Pfam domain name | Accession # | Gathering cutoff | Domain description |
|---|---|---|---|
| PI-PLC-X | PF00388.9 | 18.8 | Phosphatidylinositol-specific phospholipase C, X domain |
| PI-PLC-Y | PF00387.9 | −11.0 | Phosphatidylinositol-specific phospholipase C, Y domain |
| PI3_PI4_kinase | PF00454.17 | 14.8 | Phosphatidylinositol 3- and 4-kinase |
| PMEI | PF04043.6 | 25.0 | Plant invertase/pectin methylesterase inhibitor |
| PPDK_N | PF01326.9 | −150.2 | Pyruvate phosphate dikinase, PEP/pyruvate binding domain |
| PSK | PF06404.3 | 25.0 | Phytosulfokine precursor protein (PSK) |
| PTR2 | PF00854.12 | −50.0 | POT family |
| PaO | PF08417.2 | 25.0 | Pheophorbide a oxygenase |
| Peptidase_C14 | PF00656.12 | −22.5 | Caspase domain |
| Peptidase_S10 | PF00450.12 | −198.0 | Serine carboxypeptidase |
| Pescadillo_N | PF06732.2 | −167.1 | Pescadillo N-terminus |
| PfkB | PF00294.14 | −67.8 | pfkB family carbohydrate kinase |
| Phytochrome | PF00360.10 | 13.0 | Phytochrome region |
| Pirin | PF02678.6 | 25.0 | Pirin |
| Pirin_C | PF05726.3 | −8.8 | Pirin C-terminal cupin domain |
| Pkinase | PF00069.15 | −70.3 | Protein kinase domain |
| Pkinase_C | PF00433.14 | 14.0 | Protein kinase C terminal domain |
| Pkinase_Tyr | PF07714.7 | 65.0 | Protein tyrosine kinase |
| Pollen_allerg_1 | PF01357.11 | 17.2 | Pollen allergen |
| Prp19 | PF08606.2 | −1.5 | Prp19/Pso4-like |
| Put_Phosphatase | PF06888.3 | −100.0 | Putative Phosphatase |
| Pyridoxal_deC | PF00282.9 | −158.6 | Pyridoxal-dependent decarboxylase conserved domain |
| RPE65 | PF03055.6 | −156.5 | Retinal pigment epithelial membrane protein |
| RRM_1 | PF00076.12 | 17.7 | RNA recognition motif. (a.k.a. RRM, RBD, or RNP domain) |
| Rapamycin_bind | PF08771.1 | 25.0 | Rapamycin binding domain |
| Remorin_C | PF03763.4 | 25.0 | Remorin, C-terminal region |
| Remorin_N | PF03766.4 | 10.1 | Remorin, N-terminal region |
| Response_reg | PF00072.14 | 4.0 | Response regulator receiver domain |
| Ribonuc_2-5A | PF06479.2 | 25.0 | Ribonuclease 2-5A |
| Ribosomal_60s | PF00428.9 | 6.0 | 60s Acidic ribosomal protein |
| Ribosomal_L10 | PF00466.10 | −14.0 | Ribosomal protein L10 |
| Ribosomal_L18p | PF00861.12 | 25.0 | Ribosomal L18p/L5e family |
| Rieske | PF00355.16 | −7.0 | Rieske [2Fe—2S] domain |
| S-methyl_trans | PF02574.6 | −33.2 | Homocysteine S-methyltransferase |
| S6PP | PF05116.4 | −113.7 | Sucrose-6F-phosphate phosphohydrolase |
| S6PP_C | PF08472.1 | −34.2 | Sucrose-6-phosphate phosphohydrolase C-terminal |
| SAC3_GANP | PF03399.6 | −15.2 | SAC3/GANP/Nin1/mts3/eIF-3 p25 family |
| SATase_N | PF06426.4 | 25.0 | Serine acetyltransferase, N-terminal |
| SBP | PF03110.5 | 25.0 | SBP domain |
| SBP56 | PF05694.2 | 25.0 | 56 kDa selenium binding protein (SBP56) |
| SET | PF00856.18 | 23.5 | SET domain |
| SOH1 | PF05669.3 | 25.0 | SOH1 |
| SPX | PF03105.10 | −20.0 | SPX domain |
| SRF-TF | PF00319.9 | 11.0 | SRF-type transcription factor (DNA-binding and dimerisation domain) |
| S_locus_glycop | PF00954.11 | −12.7 | S-locus glycoprotein family |
| Sigma70_r2 | PF04542.4 | 18.6 | Sigma-70 region 2 |
| Sigma70_r3 | PF04539.6 | 10.0 | Sigma-70 region 3 |
| Sigma70_r4 | PF04545.6 | 21.6 | Sigma-70, region 4 |
| Sina | PF03145.7 | −48.4 | Seven in absentia protein family |
| Skp1 | PF01466.9 | −2.0 | Skp1 family, dimerisation domain |
| Skp1_POZ | PF03931.5 | 14.9 | Skp1 family, tetramerisation domain |
| Sterol_desat | PF01598.8 | −13.0 | Sterol desaturase |
| Sugar_tr | PF00083.14 | −85.0 | Sugar (and other) transporter |
| TFIIS | PF08711.1 | 3.0 | Transcription elongation factor S-II protein N terminal |
| TFIIS_C | PF01096.9 | 15.0 | Transcription factor S-II (TFIIS) |
| TFIIS_M | PF07500.4 | 7.4 | Transcription factor S-II (TFIIS), central domain |
| TLC | PF03219.5 | 25.0 | TLC ATP/ADP transporter |
| TPR_1 | PF00515.18 | 7.7 | Tetratricopeptide repeat |
| TPR_2 | PF07719.7 | 20.1 | Tetratricopeptide repeat |
| TPT | PF03151.7 | −15.3 | Triose-phosphate Transporter family |
| Transket_pyr | PF02779.14 | −49.0 | Transketolase, pyrimidine binding domain |
| Transketolase_C | PF02780.10 | −15.5 | Transketolase, C-terminal domain |
| Tub | PF01167.8 | −98.0 | Tub family |
| U-box | PF04564.6 | −7.6 | U-box domain |
| UAA | PF08449.2 | −146.2 | UAA transporter family |
| UDPGP | PF01704.8 | −265.2 | UTP--glucose-1-phosphate uridylyltransferase |
| UPF0005 | PF01027.11 | −6.7 | Uncharacterised protein family UPF0005 |

TABLE 23-continued

| Pfam domain name | Accession # | Gathering cutoff | Domain description |
|---|---|---|---|
| UPF0041 | PF03650.4 | −33.6 | Uncharacterised protein family (UPF0041) |
| Ubie_methyltran | PF01209.9 | −117.0 | ubiE/COQ5 methyltransferase family |
| VDE | PF07137.2 | −40.0 | Violaxanthin de-epoxidase (VDE) |
| WD40 | PF00400.22 | 21.5 | WD domain, G-beta repeat |
| WRKY | PF03106.6 | 25.0 | WRKY DNA-binding domain |
| Zein | PF01559.7 | −21.0 | Zein seed storage protein |
| adh_short | PF00106.15 | −40.2 | short chain dehydrogenase |
| bZIP_1 | PF00170.11 | 24.5 | bZIP transcription factor |
| bZIP_2 | PF07716.5 | 15.0 | Basic region leucine zipper |
| dCMP_cyt_deam_1 | PF00383.13 | −9.0 | Cytidine and deoxycytidylate deaminase zinc-binding region |
| efhand | PF00036.22 | 21.7 | EF hand |
| p450 | PF00067.12 | −105.0 | Cytochrome P450 |
| zf-B_box | PF00643.14 | 15.3 | B-box zinc finger |
| zf-C2H2 | PF00096.16 | 17.7 | Zinc finger, C2H2 type |
| zf-C3HC4 | PF00097.15 | 16.0 | Zinc finger, C3HC4 type (RING finger) |
| zf-CCCH | PF00642.15 | 0.0 | Zinc finger C-x8-C-x5-C-x3-H type (and similar) |
| zf-CCHC | PF00098.13 | 17.9 | Zinc knuckle |
| zf-CHY | PF05495.3 | 25.0 | CHY zinc finger |
| zf-Dof | PF02701.6 | 25.0 | Dof domain, zinc finger |
| zf-LSD1 | PF06943.3 | 25.0 | LSD1 zinc finger |
| zf-UBP | PF02148.9 | 25.0 | Zn-finger in ubiquitin-hydrolases and other protein |

Example 9

Selection of Transgenic Plants with Enhanced Agronomic Trait(s)

This example illustrates the preparation and identification by selection of transgenic seeds and plants derived from transgenic plant cells of this invention having recombinant DNA in a chromosome in the nucleus of such cells. The plants and seeds are identified by screening for a transgenic plant having an enhanced agronomic trait imparted by expression of a protein selected from the group including the homologous proteins identified in Example 6. Transgenic plant cells of corn, soybean, cotton, canola, wheat and rice are transformed with recombinant DNA for expressing each of the homologs identified in Example 6. Plants are regenerated from the transformed plant cells and used to produce progeny plants and seed that are screened for enhanced water use efficiency, enhanced cold tolerance, increased yield, enhanced nitrogen use efficiency, enhanced seed protein and enhanced seed oil. Plants are identified exhibiting enhanced traits imparted by expression of the homologous proteins.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09290773B2). An electronic copy of the "Sequence Listing" will also be available from the USPTO upon request and payment of the fee set forth in 37 CFR 1.19(b)(3).

What is claimed is:

1. A plant cell nucleus with stably integrated, recombinant DNA, wherein said recombinant DNA comprises a promoter that is functional in said plant cell nucleus and that is operably linked to a protein coding recombinant DNA encoding the protein consisting of SEQ ID NO: 1032 or a protein having an amino acid sequence with at least 95% but less than 100% amino acid sequence identity to SEQ ID NO: 1032; and wherein said plant cell nucleus is selected by screening a population of transgenic plants that have said recombinant DNA and an enhanced trait as compared to control plants that do not have said recombinant DNA in their nuclei; and wherein said enhanced trait is selected from the group of enhanced traits consisting of cold tolerance, yield, nitrogen use efficiency, and seed protein.

2. The plant cell nucleus of claim 1 wherein said protein coding DNA encodes the protein having the amino acid sequence of SEQ ID NO:1032.

3. The plant cell nucleus of claim 1 further comprising a DNA expressing a protein that provides tolerance from exposure to an herbicide applied at levels that are lethal to a wild type plant cell of the same species.

4. The plant cell nucleus of claim 3 wherein said herbicide is a glyphosate, dicamba, or glufosinate compound.

5. A transgenic plant comprising a plurality of plant cells with the plant cell nucleus of claim 1.

6. The transgenic plant of claim 5 which is homozygous for said recombinant DNA.

7. A transgenic seed comprising a plurality of plant cells with the plant cell nucleus of claim 1.

8. The transgenic seed of claim 7, wherein said transgenic seed is obtained from a corn, soybean, cotton, canola, alfalfa, wheat or rice transgenic plant comprising said plant cell nucleus.

9. A transgenic pollen grain comprising a haploid gamete of the plant cell nucleus of claim 1, wherein the gamete comprises said recombinant DNA.

10. A method for manufacturing non-natural, transgenic seed, said method comprising the steps of:
(a) providing a population of transgenic plants transformed with a recombinant DNA construct comprising a promoter that is functional in a plant cell and that is operably linked to a protein coding recombinant DNA encoding the protein consisting of SEQ ID NO: 1032 or a protein having an amino acid sequence with at least 95% but less than 100% amino acid sequence identity to SEQ ID NO: 1032, wherein said recombinant DNA construct is stably integrated into the genome of said transgenic plants;
(b) screening the population of transgenic plants provided in step (a) for an enhanced trait and said recombinant DNA, wherein said enhanced trait is selected from the group of enhanced traits consisting of water use efficiency, cold tolerance, heat tolerance, resistance to salt exposure, shade tolerance, yield, nitrogen use efficiency, seed protein and seed oil as compared to control plants of the same species lacking said DNA construct;
(c) selecting one or more transformed plants from said screening of step (b) which exhibit said enhanced trait as compared to said control plants lacking said DNA construct, wherein said enhanced trait is due to the expression of said protein in said selected transformed plants;
(d) verifying that said recombinant DNA is stably integrated in said selected transformed plants;
(e) analyzing tissue of said selected transformed plants to determine the expression of a gene that encodes a protein having the function of a protein having the amino acid sequence of SEQ ID NO:1032; and
(f) collecting seed from said selected transformed plants.

11. A method of producing hybrid corn seed comprising:
(a) acquiring hybrid corn seed from a herbicide tolerant corn plant which also has stably-integrated recombinant DNA construct comprising a promoter that is functional in plant cells and that is operably linked to a protein coding recombinant DNA encoding the protein consisting of SEQ ID NO: 1032 or a protein having an amino acid sequence with at least 95% but less than 100% amino acid sequence identity to SEQ ID NO: 1032, wherein said recombinant DNA construct is stably integrated into the genome of said hybrid corn seed;
(b) producing corn plants from said hybrid corn seed of step a), wherein a fraction of the plants produced from said hybrid corn seed is homozygous for said recombinant DNA, a fraction of the plants produced from said hybrid corn seed is hemizygous for said recombinant DNA, and a fraction of the plants produced from said hybrid corn seed has none of said recombinant DNA;
(c) selecting corn plants which are homozygous and hemizygous for said recombinant DNA by treating with an herbicide;
(d) collecting seed from herbicide-treated-surviving corn plants and planting said seed to produce further progeny corn plants;
(e) repeating steps (c) and (d) at least once to produce an inbred corn line; and
(f) crossing said inbred corn line with a second corn line to produce hybrid seed; and wherein said inbred corn line of step (e) and hybrid seed of step (f) comprise said recombinant DNA.

* * * * *